(12) United States Patent
Gazic Smilovic et al.

(10) Patent No.: US 9,315,525 B2
(45) Date of Patent: Apr. 19, 2016

(54) SYNTHETIC ROUTE FOR THE PREPARATION OF α-AMINO BORONIC ACID DERIVATIVES VIA SUBSTITUTED ALK-1-YNES

(75) Inventors: Ivana Gazic Smilovic, Ljubljana (SI); Zdenko Casar, Ljubljana (SI)

(73) Assignee: Lek Pharmaceuticals D.D., Ljubljana (SI)

( * ) Notice: Subject to any disclaimer, the term of this patent is extended or adjusted under 35 U.S.C. 154(b) by 715 days.

(21) Appl. No.: 13/379,181

(22) PCT Filed: Jun. 18, 2010

(86) PCT No.: PCT/EP2010/058666
§ 371 (c)(1),
(2), (4) Date: May 11, 2012

(87) PCT Pub. No.: WO2010/146172
PCT Pub. Date: Dec. 23, 2010

(65) Prior Publication Data
US 2012/0231993 A1    Sep. 13, 2012

(30) Foreign Application Priority Data

Jun. 19, 2009  (EP) ..................................... 09163227
Jul. 27, 2009  (EP) ..................................... 09166475
Dec. 21, 2009  (EP) ..................................... 09180099

(51) Int. Cl.
    *C07F 5/02*   (2006.01)
(52) U.S. Cl.
    CPC ..................................... *C07F 5/025* (2013.01)
(58) Field of Classification Search
    CPC ....................................................... C07F 5/025
    USPC ....................................................... 544/229
    See application file for complete search history.

(56) References Cited

U.S. PATENT DOCUMENTS

| | | |
|---|---|---|
| 5,637,782 A | 6/1997 | Kalnes |
| 2001/0012907 A1 | 8/2001 | Sato |
| 2003/0008828 A1 | 1/2003 | Priestley |

FOREIGN PATENT DOCUMENTS

| | | |
|---|---|---|
| EP | 0126501 A2 | 11/1984 |
| WO | WO 2005/097809 A2 | 10/2005 |
| WO | WO 2009/004350 A1 | 1/2009 |

OTHER PUBLICATIONS

Wang Z et al, "A New and Practical Synthesis of Vinyl Dichlorides via a non-Wittig-type approach",Tetrahedron Letters, vol. 41, No. 21, May 1, 2000, pp. 4007-4009.
Matteson D S et al, "(R)-1-Acetamido-2-phenylethaneboronic acid". A specific transition-state analog for chymotrypsin, Journal of the American Chemical Society, vol. 103, No. 17, Aug. 26, 1981, pp. 5241-5242.
Reppe W et al; "Vinylierung", Justus Liebigs Annalen Der Chemie, vol. 601, 1956, pp. 81-138.
Baganz H et al, "Über 1-Phenoxy-2-äthoxy-äthen =1-Phenoxy-2-ethoxyethene", Chemische Berichte. vol. 86, No. 10, Oct. 1953, pp. 1318-1322.
Shostakovskii M F et al, "Synthesis and Transformations of Organosilicon Vinyl Ethers", Journal of General Chemistry of the USSR, vol. 29, 1959, pp. 370-379.
Kalabina A V et al, "Synthesis and Derivatives of Vinyl Ethers of Chlorophenols", Izvestiya Sibirskogo Otdeleniya Akademii Nauk SSSR, 1958, pp. 9-16.
Reppe W et al, "Äthinylierung V. Reaktionen Hydrierter Äthinylierungsprodukte Dehydratisierung von y-Alkandiolen = Ethynylation. V. Reactions of Hydrated Ethynylation Products. Dehydration of y-alkanediols", Justus Liebigs Annalen Der Chemie, vol. 596, 1955, pp. 80-158.
Deloux L et al, "Stereospecific Synthesis of Temarotene, Its Structural Isomers, and Mixed Triaryl Alkenes from gem-Borazirconocene Alkenes" Journal of Organic Chemistry, vol. 60, No. 11,Jun. 2, 1995, pp. 3276-3277.
Desurmont G et al, "Zirconocene-Mediated Preparation of 1 , 3-, 1, 4-, and 2, 3-Dibora-1, 3-butadienes: Their Isolation and Characterization and Use in Suzuki-Miyaura Coupling" Organometallics, vol. 15, No. 15, Jul. 23, 1996, pp. 3323-3328.
Eddarir S et al, "Regiospecific Synthesis of Symmetrical (1 E,3E) 2,3-difluoro-1,4- diphenyl-buta-1 ,3-dienes via palladium-catalyzed cross-coupling of (Z) 2-bromo-2-fluoroethenylbenzenes in presence of bis(pinacolato)diboron" Journal of Fluorine Chemistry, vol. 125, No. 3, Mar. 1, 2004, pp. 377-380.
Bhat N G et al, "A Novel Synthesis of (E)-gem-Dimetalloalkenes Containing Boron and Silicon: An Easy Access to Alkyl Trimethylsilyl Ketones" SYNLETT, No. 2, 2004, pp. 297-298.
Bhat N G et al, "A Novel Synthesis of β-ketosilanes via Organoboranes" Tetrahedron Letters, vol. 41, No. 34, Aug. 19, 2000, pp. 6541-6544.
Batey R A et al, "Alkenyl and Aryl Boronates—Mild Nucleophiles for the Stereoselective Formation of Functionalized N-heterocycles"Journal of the American Chemical Society, vol. 121, No. 21, Jun. 2, 1999, pp. 5075-5076.
Lhermitte F et al, "Radical Reactions in Organoboron Chemistry. III—Addition Reactions to Alkynylboranes as Efficient Routes to New Regio- and Stereodefined Alkenyl Diamino- and Dialkoxyboranes" SYNLETT, No. 4, Apr. 1996, pp. 377-379.

(Continued)

*Primary Examiner* — Scarlett Goon
*Assistant Examiner* — Ana Z Muresan
(74) *Attorney, Agent, or Firm* — Arent Fox LLP

(57) ABSTRACT

A process for producing bortezomib N-(pyrazin-2-yl)carbonyl-L-phenylalanine-L-leucine boronic acid) comprising the step of deprotecting the compound of formula XII:

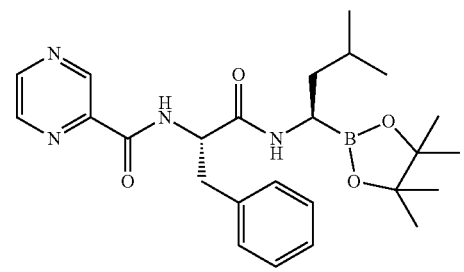

to yield bortezomib.

8 Claims, No Drawings

(56) References Cited

OTHER PUBLICATIONS

Trost B M et al, "Nickel Catalysed Coupling of Allylamines and Boronic Acids" Journal of the Chemical Society, Perkin Transactions 1, No. 17, 1995, pp. 2083-2096.

Brown H C et al, "A Convenient Synthesis of Alpha,Gamma-Unsaturated Ketones via Allylation of Z-1-Halo-1-Alkenyl-1,3,2-Dioxaborolane" Tetrahedron Letters, vol. 35, No. 38, Sep. 19, 1994, pp. 6963-6966.

Kamabuch I A et al, "Synthesis of Functionalized 1-alkenylboronates via hydroboration-dealkylation of alkynes with diisopinocampheylborane" Synthetic Communications, vol. 23, No. 20, 1993, pp. 2851-2859.

Waas J R et al, "Preparation and reaction of 1, 1-zinc, boron and 1, 1-copper, boron alkenyl bimetallics" Tetrahedron Letters, vol. 33, No. 26, Jun. 23, 1992, pp. 3717-3720.

Brown H C et al, "Vinylic Organoboranes. 7. Stereoselective Synthesis of (E)-(1 Substituted-1-alkenyl)boronic esters by the Nucleophilic Substitution of (2)-1-(Bromo-1-alkenyl)boronic esters with Organolithium or Grignard Reagents. Isolation and Oxidation to Ketones" Journal of Organic Chemistry, vol. 51, No. 26, Dec. 1986, pp. 5277-5282.

Brown H C et al, "Organoboranes. 37. Synthesis and Properties of (Z)-1-Alkenylboronic Esters" Organometallics, vol. 3, No. 9, Sep. 1984, pp. 1392-1395, DOI: 10.1021/om00087a013.

Brown H C et al, "Organoboranes. 30. Convenient Procedures for the Synthesis of Alkyl -and Alkenylboronic Acids and Esters" Organometallics, vol. 2, No. 10, Oct. 1983, pp. 1311-1316.

Schaumberg G D et al, "Dibutyl cis- and trans-1-butene-1-boronate" Journal of Organometallic Chemistry, vol. 20, No. 1, Nov. 1, 1969, pp. 261-263.

Matteson D S et al, "Dibutyl Acetyleneboronate: Preparation and Some Additions of Free Radicals" Journal of Organic Chemistry, vol. 28, Feb. 1963, pp. 369-371.

Matteson D S et al, "R-1-Acetamido-2-phenylethaneboronic acid. A specific transition-state analog for chymotrypsin" Journal of the American Chemical Society, vol. 103, No. 17, Aug. 1981, pp. 5241-5242.

Kettner C A et al, "Inhibition of the serine proteases leukocyte elastase, pancreatic elastase, cathepsin G, and chymotrypsin by peptide boronic acids" Journal of Biological Chemistry, vol. 259, No. 24, Dec. 25, 1984, pp. 15106-15114.

Satoh M et al, "Stereo- and regiospecific synthesis of trisubstituded alkenes via the palladium-catalyzed cross-coupling reaction of diisopropyl (E)-(1-alkyl-1-alkenyl) boronates with organic halides" Chemistry Letters, vol. 15, No. 8, Aug. 5, 1986, pp. 1329-1332.

Kim B J et al, "Conversion of alkyltrifluoroborates into alkyltrifluoroborates with tetrachlorosilane in coordinating solvents", Angewandte Chemie, International Edition, vol. 43, No. 23, Jun. 7, 2004, pp. 3056-3058.

Matteson D S, et al, "Cesium alkyltrifluoroborates from asymmetric boronic esters", SYNLETT, No. 20, Dec. 18, 2006, pp. 3501-3503.

SYNTHETIC ROUTE FOR THE PREPARATION OF α-AMINO BORONIC ACID DERIVATIVES VIA SUBSTITUTED ALK-1-YNES

CROSS-REFERENCE TO RELATED APPLICATION

This application is a National Stage entry of International Application No. PCT/EP2010/058666, filed Jun. 18, 2010, which claims priority to European Application Nos. 09163227.3, filed Jun. 19, 2009, Ser. No. 09/166,475.5, filed Jul. 27, 2009, Ser. No. 09/180,099.5, filed Dec. 21, 2009, the entire specifications, claims and drawings of which are incorporated herewith by reference.

FIELD OF THE INVENTION

The present invention relates in general to the field of organic chemistry and in particular to the preparation of α-amino boronic esters. These compounds can be used as intermediates in the synthesis of boronic acid and ester compounds such as N-terminal peptidyl boronic acid derivatives, for example N-(pyrazin-2-yl)carbonyl-L-phenylalanine-L-leucine boronic acid, i.e. bortezomib.

BACKGROUND OF THE INVENTION

Amino boronic acids—amino acids wherein terminal carboxylic groups are replaced by boronic $B(OH)_2$ groups—are important pharmacoisosters of amino acids in various therapeutically promising molecules, mainly for treatment of cancer. For instance, talabostat contains proline boronic acid, bortezomib contains leucine boronic acid. Bortezomib, chemically N-(pyrazin-2-yl)carbonyl-L-phenylalanine-L-leucine boronic acid, is an important proteasome inhibitor and has been clinically approved for use in treating mantle cell lymphoma and multiple myeloma. Recently, many novel molecules containing amino boronic acids, especially leucine boronic acid, have been prepared and biologically tested as described in WO2009/006473 A2.

The synthesis of bortezomib and other amino boronic acid and ester compounds is disclosed in EP0788360 B1, international patent application WO2005/097809 A2, international patent application WO2009/004350 A1, and international patent application WO2009/036281 A2.

EP0788360 B1 describes a general process for preparation of amino boronic acid and ester compounds using (1S,2S,3R,5S)-pinanediol leucine boronate and an amino acid or its derivative as starting materials. As coupling agents 1-ethyl-3-(3-dimethylamino-propyl)carbodiimide hydrochloride (EDC), benzotriazol-1-yloxytris (dimethylamino) phosphonium hexafluorophosphate (BOP reagent), or O-(1H-benzotriazol-1-yl)-N,N,N',N'-tetramethyluronium tetrafluoroborate (TBTU) were employed.

A synthetic process suitable for a large scale production of amino boronic acid and ester compounds is described in WO2005/097809 A2. The synthesis involves a boronate complex, which is contacted with a Lewis acid under conditions that afford the boronic ester compounds.

WO2009/004350 A1 discloses a high yield synthesis of bortezomib and intermediates for the synthesis thereof. The procedure includes the use of a very high percentage of tetrahydrofuran in the halogenation of the starting compound (S)-pinanediol 2-methylpropane-1-boronate.

WO2009/036281 A2 describes processes for the preparation of substantially pure bortezomib and intermediates thereof. Processes for the preparation of crystalline forms of bortezomib as well as a storage system for bortezomib are also disclosed in said patent application.

In international patent application WO2005/097809 A2, in *J. Biol. Chem.* 1984, 259, 15106-15114 and in *J. Am. Chem. Soc.* 1981, 103, 5241-5242 a route for the preparation of α-amino boronic esters, which is known to the person skilled in the art known as the Matteson's synthetic route, is described. Homologation of boronic esters with (dichloromethyl)lithium to form α-chloro boronic esters has been shown to be efficient and result in good chiral selectivity if pinanediol was used as the chiral directing group. The use of the Lewis acid ($ZnCl_2$) as a catalyst and chloride ion scavenger for the rearrangement of the borate intermediate improved the diastereomeric ratio in the α-chloro boronic ester product. α-Chloro boronic esters have been converted to silylated α-amino boronic esters by lithiumhexamethyldisilazane (LiHMDS), which have been desilylated and protonated in situ to the α-amino boronic esters.

An approach for the synthesis of diverse α-amino boronic esters by the highly diastereoselective copper-catalyzed addition of bis(pinacolato)diboron to N-tert-butane sulfinyl aldimines has been disclosed in the *J. Am. Chem. Soc.* 2008, 130, 6910-6911.

Transformation of 1,1-dihalogenoalkenes to corresponding alkynes and subsequent synthesis of 1-alkynylboranes have been described in *Tetrahedron Letters* 1972, 13, 3769-3772 and *Tetrahedron Letters* 1988, 29, 2631-2634.

*J. Am. Chem. Soc.* 1994, 116, 10302-10303 describes a process for preparing α-substituted 1-alkenyldioxaborolanes starting from 1-alkynyldioxaborolanes by hydrozirconation followed by substitution such as halogenation or carbonylation. The following α-substituted 1-alkenyldioxaborolanes are disclosed in this reference: (E)-2-(1-chloro-3,3-dimethylbut-1-enyl)-4,4,5,5-tetramethyl-1,3,2-dioxaborolane, (E)-2-(1-bromo-3,3-dimethylbut-1-enyl)-4,4,5,5-tetramethyl-1,3,2-dioxaborolane, (E)-2-(1-iodo-3,3-dimethylbut-1-enyl)-4,4,5,5-tetramethyl-1,3,2-dioxaborolane, (E)-2,2,6,6-tetramethyl-4-(4,4,5,5-tetramethyl-1,3,2-dioxaborolan-2-yl) hept-4-en-3-one, (E)-4,4-dimethyl-1-phenyl-2-(4,4,5,5-tetramethyl-1,3,2-dioxaborolan-2-yl)pent-2-en-1-one, (E)-2-(4,4-dimethylpent-2-en-2-yl)-4,4,5,5-tetramethyl-1,3,2-dioxaborolane zirconocene and (E)-2-(hept-2-en-2-yl)-4,4,5,5-tetramethyl-1,3,2-dioxaborolane zirconocene.

There is a need in the art for new intermediate compounds and efficient processes for the preparation of α-substituted boronic esters.

SUMMARY OF THE INVENTION

The present invention provides the following items including main aspects and preferred embodiments, which respectively alone and in combination particularly contribute to solving the above object and eventually provide additional advantages:

(1) A process for preparing a compound of formula VI

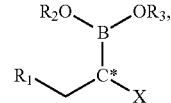

wherein:
R₁ is hydrogen, substituted or unsubstituted alkyl, substituted or unsubstituted aryl, or substituted or unsubstituted aralkyl;
R₂ and R₃ independently from each other represent substituted or unsubstituted alkyl, substituted or unsubstituted aryl, or substituted or unsubstituted aralkyl, or R₂ and R₃ cooperatively form a part of a 5- to 10-membered fused or unfused ring, optionally a chiral 5- to 10-membered fused or unfused ring; and
X is selected from the group consisting of Cl, Br, I, OCOR' and OSO₂R', wherein R' represents substituted or unsubstituted alkyl, substituted or unsubstituted aryl or substituted or unsubstituted aralkyl; and
* indicates a chiral center;
wherein said process comprises the steps of:
(i) providing a compound of formula V

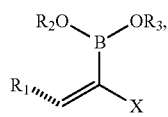

wherein R₁, R₂, R₃ and X are defined as above; and
(ii) converting said compound of formula V to compound of formula VI by hydrogenation.

The term "alkyl" as employed herein includes both straight and branched hydrocarbon chains of up to 12 carbons, preferably 1-8 carbons, such as methyl, ethyl, propyl, i-propyl, butyl, t-butyl, i-butyl, pentyl, hexyl, i-hexyl, heptyl, 4,4-dimethylpentyl, octyl, 2,2,4-trimethylpentyl, nonyl, decyl, undecyl and dodecyl, or cyclic hydrocarbons including saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl.

The term "aryl" as employed herein by itself or as part of another group refers to monocyclic or bicyclic aromatic groups containing from 6 to 12 carbons in the ring portion, preferably 6-10 carbons in the ring portion, such as phenyl or naphthyl.

The term "arylalkyl" as used herein means that the aforementioned aryl moieties are incorporated into the aforementioned straight or branched alkyl moieties either at one of the proximal or distal ends of the alkyl chain or between the aforementioned alkyl chains. For example, proximal end means for R₁ e.g. adjacent to the double bond of compound of formula V, and for R₂ and R₃ adjacent to the oxygen of compound of formula V and VI, while distal means the terminal end of the arylalkyl moiety.

The term "substituted" as employed herein includes alkyl, aryl or aralkyl groups as defined above that have one, two or three halogen substituents, or one $C_{1-6}$ alkyl($C_{6-10}$)aryl, halo ($C_{6-10}$)aryl, $C_{3-8}$ cycloalkyl, $C_{1-6}$ alkyl($C_{3-8}$)cycloalkyl, $C_{2-8}$ alkenyl, $C_{2-8}$ alkynyl, hydroxy and/or carboxy.

The term "fused" as used herein means at least two rings connected one to the other with at least one common bond.

The hatched line as shown in the structural formula of compound of formula V for
C—R₁ bonds means that the geometrical configuration is not defined, but compound of formula V may be in form of a mixture of both (E) and (Z) isomers or in form of pure (E) and (Z) isomer respectively.

The procedural concept according to this aspect of the invention involving conversion of compound of formula V to compound of formula VI provides for an industrially applicable and competitive process, since—in contrast to the Matteson's methodology, which is used in prior art to obtain α-substituted boronic esters—there is no difficulty to control rearrangement step. Furthermore, choosing compound of formula V as the starting material enables the use of inexpensive and readily available prior starting materials to obtain such a compound, while the use of toxic and/or hazardous reagents can be avoided.

R₂ and R₃ may be selected in view of subsequent procedural steps. For example, in case R₂ and R₃ are used as protecting group(s) only, achiral R₂ and R₃ may be used which can be introduced by readily available and/or inexpensive reagents. On the other hand, if R₂ and R₃ represent an integral part of the compound to be produced, or if R₂ and R₃ act as directing group(s), then suitable chiral group(s) may be selected for R₂ and R₃.

(2) The process according to item (1), wherein R₁ is selected from a group consisting of hydrogen, substituted or unsubstituted linear $C_1$-$C_5$-alkyl, substituted or unsubstituted branched $C_1$-$C_5$-alkyl and substituted or unsubstituted $C_3$-$C_8$-cycloalkyl, wherein R₂ and R₃ are selected from a group consisting of linear substituted or unsubstituted $C_1$-$C_5$-alkyl, substituted or unsubstituted branched $C_1$-$C_5$-alkyl, or R₂ and R₃ form a part of a 5- to 10-membered fused or unfused ring, optionally a chiral 5- to 10-membered fused or unfused ring; preferably R₁ is unsubstituted linear or branched $C_1$-$C_5$-alkyl, and/or R₂ and R₃ form a part of a 5-membered ring; more preferably, R₁ is isopropyl and/or R₂ and R₃ cooperatively form a part of a 5-membered ring representing 4,4,5,5-tetramethyl-[1,3,2]dioxaborolane.

(3) The process according to item (1) or (2), wherein X is a halogen selected from the group consisting of Cl, Br and I.

(4) The process according to any one of the preceding items, wherein said hydrogenation is conducted in the presence of a catalyst, preferably said catalyst is a catalyst for homogeneous catalysis.

(5) The process according to item (4), wherein the catalyst is selected from complexes comprising transition metal(s).

In a complex comprising transition metal(s), i.e. catalyst, the transition metal is preferably complexed with at least one ligand containing electron-rich species such as various double bonded compounds and/or free electron pair containing O, N, S, or P species. More preferably, the transition metal catalyst has chirality in the ligand and/or at the transition metal atom, or the transition metal complex having chirality is formed in situ by using an achiral procatalyst comprising the transition metal together with a cocatalyst having chirality, such as a chiral ligand. Even more preferably, the aforementioned components having chirality are in enantiontiopure or diastereomerically pure form. In particular, at least one of said ligands has chirality, wherein said ligand(s) is/are in enantiopure or diasteriomerically pure form. Such ligands for instance may include, but are not limited to, (S)-2-(1-(bis(2, 6-dimethylphenyl)phosphino)-2-methylpropan-2-yl)-4-tert-butyl-4,5-dihydrooxazole; (S)-4-tert-butyl-2-(2-(diphenylphosphino)phenyl)-4,5-dihydrooxazole; (4S,5S)-4-(2-(dicyclohexylphosphinooxy)-1,3-diphenylpropan-2-yl)-5-methyl-2-phenyl-4,5-dihydrooxazole; (R,R)—P,N-ferrocene oxazoline; (R,R)—P,N-ferrocene imidazoline; benzoyl-(R, R)—P,N-ferrocene imidazoline; (R)-(+)-2,2',6,6'-tetramethoxy-4,4'-bis(diphenylphosphino)-3,3'-bipyridine (i.e. (R)—P-Phos); (S)-2,2',6,6'-tetramethoxy-bis[di(3,5-dimethylphenyl)phosphino]-3,3'-bipyridine (i.e. (S)-Xyl-P-Phos);

(R)-4,12-bis(diphenylphosphino)-[2.2]-paracyclophane (i.e. (R)-phane-Phos); 1-(S)—N-methyl-N-(diphenyl-phosphino)-1-[(R)-(diphenylphosphino)-ferrocenyl]ethylamine (i.e. (S)-MeBoPhos); (R)-2-(1-naphthyl)-8-diphenylphosphino-1-(S)-3,5-dioxa-4-phosphacyclohepta[2,1-1;3,4-a']dinaphthalen-4-yl)-1,2-dihydroquinoline toluene aduct (i.e. (Sa,Rc)-(1-Nph)-Quinaphos); (S)-(+)-4,12-bis[di(3,5-dimethylphenyl)phosphino]-[2.2]paracyclophane (i.e. (S)-XylPhanePhos); (R)-2,2'-bis(diphenyl-phosphinoamino)-5,5',6,6',7,7',8,8'-octahydro-1,1'-binaphthyl (i.e. (R)—H8-Binam-P). Preferred chiral ligands are (S)-2-(1-(bis(2,6-dimethylphenyl)phosphino)-2-methylpropan-2-yl)-4-tert-butyl-4,5-dihydrooxazole; (S)-4-tert-butyl-2-(2-(diphenylphosphino)phenyl)-4,5-dihydrooxazole; (4S,5S)-4-(2-(dicyclohexyl-phosphinooxy)-1,3-diphenylpropan-2-yl)-5-methyl-2-phenyl-4,5-dihydrooxazole, (R,R)—P,N-ferrocene oxazoline, (R,R)—P,N-ferrocene imidazoline and benzoyl-(R,R)—P,N-ferrocene imidazoline. Preferably, the complex comprising transition metal(s) is used at a molar substrate to catalyst ratio in the range of 5:1 to 100:1, more preferably at a molar substrate to catalyst ratio in the range of 5:1 to 50:1.

(6) The process according to item (5), wherein the transition metal comprised in the complex is selected from the group consisting of Cu, Co, Ni, Rh, Ru, Pd and Ir, preferably Rh, Ru, Pd and Ir, more preferably Ru and Ir, and in particular Ir.

(7) The process according to item (5) or (6), wherein the catalyst is selected from the group consisting of (1,5-cyclooctadiene)(pyridine)(tricyclohexylphosphine)iridium (I)hexafluoro-phosphate, (1,5-cyclo-octadiene)indium(I) tetrakis[3,5-bis(trifluoromethyl)phenyl]borate (S)-2-(1-(bis(2,6-dimethylphenyl)phosphino)-2-methylpropan-2-yl)-4-tert-butyl-4,5-dihydrooxazole, (1,5-cyclooctadiene) iridium(I)tetrakis[3,5-bis(trifluoromethyl)phenyl]borate (S)-4-tert-butyl-2-(2-diphenyl phosphino)phenyl)-4,5-dihydrooxazole, (1,5-cyclooctadiene)iridium(I)tetrakis[3,5-bis(trifluoromethyl)phenyl]borate (4S,5S)-4-(2-(dicyclohexylphosphinooxy)-1,3-diphenylpropan-2-yl)-5-methyl-2-phenyl-4,5-dihydrooxazole, (1,5-cyclooctadiene) iridium(I)tetrakis[3,5-bis(trifluoromethyl)phenyl]borate (R,R)—P,N-ferrocene oxazoline, (1,5-cyclooctadiene)iridium(I)tetrakis[3,5-bis(trifluoromethyl)phenyl]borate (R,R)—P,N-ferrocene imidazoline, and (1,5-cyclooctadiene)indium(I)tetrakis[3,5-bis(trifluoromethyl)phenyl]borate benzoyl-(R,R)—P,N-ferrocene imidazoline, bis(1,5-cyclooctadiene)diiridium(I)dichloride (R)-(+)-2,2',6,6'-tetramethoxy-4,4'-bis(diphenylphosphino)-3,3'-bipyridine; bis(1,5-cyclooctadiene)diiridium(I)dichloride (S)-2,2',6,6'-tetramethoxy-bis[di(3,5-dimethylphenyl) phosphino]-3,3'-bipyridine; bis(1,5-cyclooctadiene) dirhodium(I)dichloride (S)-2,2',6,6'-tetramethoxy-bis[di (3,5-dimethylphenyl)phosphino]-3,3'-bipyridine; bis (cycloocta-1,5-diene)rhodium(I)tetrafluoroborate (R)-4,12-bis(diphenylphosphino)-[2.2]-paracyclophane; benzeneruthenium(II) dichloride dimer 1-(S)—N-methyl-N-(diphenylphosphino)-1-[(R)-(diphenylphosphino)-ferrocenyl]ethylamine and bis(2-methylallyl)(1,5-cyclooctadien)ruthenium(II) (S)-(+)-4,12-bis[di(3,5-dimethylphenyl)phosphino]-[2.2]paracyclophane.

(8) The process according to any one of the preceding items, wherein hydrogenation is carried out at a temperature from about 10° C. to 80° C., preferably at about 45° C. to 55° C., more preferably about 50° C.

The term "about" as used herein means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

(9) The process according to any one of the preceding items, wherein hydrogenation is carried out at a pressure of hydrogen of about 5 to 20 bar; and/or wherein the reaction time is about 1 to 20 days, preferably about 1 to 10 days.

(10) The process according to any one of items (3) to (9), wherein dehalogenation is essentially avoided during hydrogenation, preferably dehalogenation occurs in less than 10 molar %, more preferably in less than 5 molar %, most preferably in less than 3 molar %, in particular in less than molar 1% relative to the molar amount of compound of formula VI.

The term "dehalogenation" as used herein means a reaction wherein a halogen is removed from a compound and replaced by hydrogen.

During a hydrogenation process halogen attached to a double bond of alkenes is usually submitted to dehalogenation. According to this beneficial embodiment of the invention, it has been surprisingly found that substituted α-halogenovinyl boronic esters of formula V can be hydrogenated to arrive at α-halogeno boronic esters of formula VI without a substantial risk of dehalogenation. By further choosing a suitable catalyst which provides for mild reaction conditions, dehalogenation of compounds of formula V can be essentially avoided.

(11) The process according to any one of the preceding items, wherein enantiomerically pure compound of formula VI is obtained by enantiomeric resolution applied subsequent to step (ii).

"Enantiomeric resolution" as employed herein means separating enantiomers by means known in the art such as chiral column chromatography or by crystallization of diastereomeric salts.

(12) The process according to any one of items (1) to (11), wherein the compound of formula VI

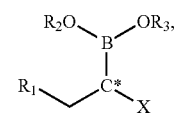

VI wherein $R_1$, $R_2$ and $R_3$ are defined as above, and X is selected from the group consisting of Cl, Br, I, OCOR' and OSO$_2$R' in which R' represents substituted or unsubstituted alkyl, substituted or unsubstituted aryl or substituted or unsubstituted aralkyl is further converted to a compound of formula VI'

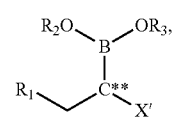

VI' wherein $R_1$, $R_2$ and $R_3$ are defined as above; and
X' is selected from the group consisting of Cl, Br, I, OCOR' and OSO$_2$R' in which R' represents substituted or unsubstituted alkyl, substituted or unsubstituted aryl or substituted or unsubstituted aralkyl, and X' is not the same as X, wherein a chiral center ** has the opposite stereochemical configuration of the chiral center*.

by applying nucleophilic substitution reaction of type $S_N2$.

According to this preferred embodiment of the invention, the stereochemical configuration of the chiral center of compound of formula VI can be converted into a chiral center having the opposite stereochemical configuration. This provides for conversion of an "undesired" stereoisomer into a "desired" stereoisomer. Therefore, products of hydrogenation reactions that are not completely steroselective can be subjected to chiral chromatography resolution of stereoisomers. The desired stereoisomer of VI can be collected, and undesired stereoisomer subjected to additional $S_N2$ reaction to provide additional amount of desired stereoisomer. By this process the highest possible amount of V can be converted to the desired stereoisomer. The term "desired stereoisomer" as used herein means a compound of formula VI having the desired an stereochemical configuration at the α-carbon atom for further synthesis such as production of a N-terminal peptidyl boronic acid derivative of formula X or a bortezomib derivative. The term "undesired" stereoisomer as used herein means a compound of formula VI having an stereochemical configuration at the α-carbon atom which is opposite to the configuration of the desired stereoisomer. For example, the (S)-enantiomer may represent the undesired stereoisomer and therefore be converted into the desired (R)-enantiomer respectively. "Undesired" stereoisomer may e.g. be obtained from enantiomeric resolution.

Furthermore, this embodiment provides for a flexible application of "desired" compound of formula VI in a multitude of different subsequent syntheses, since the stereochemical configuration at the chiral center can subsequently be suitably selected in case the pathway of synthesis or even the target product of, the synthetic pathway is changed.

(13) The process according to any one of the preceding items, wherein the compound of formula V

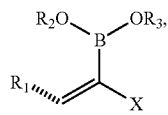

wherein $R_1$ is hydrogen, substituted or unsubstituted alkyl substituted or unsubstituted aryl, or substituted or unsubstituted aralkyl;

$R_2$ and $R_3$ independently from each other represent substituted or unsubstituted alkyl, substituted or unsubstituted aryl, or substituted or unsubstituted aralkyl, or $R_2$ and $R_3$ cooperatively form a part of a 5- to 10-membered fused or unfused ring, optionally a chiral 5- to 10-membered fused or unfused ring; and X is selected from the group consisting of Cl, Br, I, OCOR' and OSO$_2$R' in which R' represents substituted or unsubstituted alkyl, substituted or unsubstituted aryl or substituted or unsubstituted aralkyl, is prepared from a compound of formula III

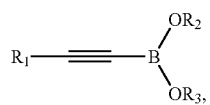

wherein $R_1$, $R_2$ and $R_3$ are defined as above,
by hydrozirconation converting compound of formula III into compound of formula IV

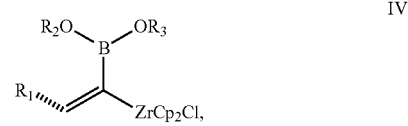

wherein the ZrCp$_2$Cl moiety of compound of formula IV is substituted by X as defined above.

The hatched line as shown in the structural formula of compound of formula IV for C—R$_1$ bonds means that the geometrical configuration is not defined, but compound of formula IV may be in form of a mixture of both (E) and (Z) isomers or in form of pure (E) and (Z) isomer respectively.

The term "hydrozirconation" as employed herein means a hydro-metallo-addition of alkenes and alkynes to give organometallic compounds, by using zirconium containing reagent, Cp$_2$ZrHCl, also known as the Schwartz's reagent.

For the terms "alkyl", "aryl", "aralkyl" and "substituted", reference is made to the corresponding definitions under item (1).

(14) The process according to item (13), wherein ZrCp$_2$Cl moiety of compound of formula IV is substituted by halogen selected from Cl, Br, I, preferably Cl, by means of halogenation, preferably by halogenation in situ.

The term "halogenation" as employed herein means a reaction of substitution in which organometallic compounds comprising Schwartz's intermediate react with halogens to give alkenyl or aryl halides.

(15) The process according to item (14), wherein halogenation is carried out by a reactant selected from the group consisting of Cl$_2$, Br$_2$, I$_2$, N-chlorosuccinimide, N-bromosuccinimide and N-iodosuccinimide, preferably N-chlorosuccinimide, N-bromosuccinimide and N-iodosuccinimide, more preferably N-chlorosuccinimide; and/or wherein the solvent is selected from the group consisting of THF, CH$_2$Cl$_2$, 1,2-dichloroethane (DCE), Et$_2$O, MTBE, i-Pr$_2$O, MeTHF and toluene, preferably CH$_2$Cl$_2$, DCE and THF, more preferably CH$_2$Cl$_2$ and THF.

(16) The process according to items (13) to (15), wherein the halogen is optionally further converted to a moiety selected from the group consisting of OCOR' and OSO$_2$R', wherein R' represents substituted or unsubstituted alkyl, substituted or unsubstituted aryl or substituted or unsubstituted aralkyl.

(17) A process for preparing a compound of formula III

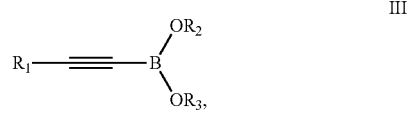

wherein $R_1$ is hydrogen, substituted or unsubstituted alkyl substituted or unsubstituted aryl, or substituted or unsubstituted aralkyl;

$R_2$ and $R_3$ independently from each other represent substituted or unsubstituted alkyl, substituted or unsubstituted aryl, or substituted or unsubstituted aralkyl, or $R_2$ and $R_3$ cooperatively form a part of a 5- to 10-membered fused or unfused ring, optionally a chiral 5- to 10-membered fused or unfused ring;

wherein said process comprises the steps of:
(i) providing a compound of formula I

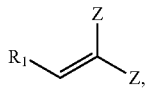
I wherein $R_1$ is hydrogen, substituted or unsubstituted alkyl substituted or unsubstituted aryl, or substituted or unsubstituted aralkyl;
Z is selected from the group consisting of Cl, Br and I, preferably Cl,
(ii) adding a strong organometallic base to a solution of a compound of formula I in order to convert compound of formula I to compound of formula II

II wherein $R_1$ is defined as above,
(iii) reacting the compound of formula II with a compound of formula IX

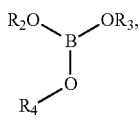
IX wherein $R_2$ and $R_3$ are defined as above,
and $R_4$ represents substituted or unsubstituted alkyl, substituted or unsubstituted aryl, or substituted or unsubstituted aralkyl, wherein $R_4$ is same or different group as $R_2$ and/or $R_3$,
in the presence of a solvent and followed by addition of an acid,
wherein steps (i), (ii) and (iii) are performed as a one pot reaction without isolation of compound of formula II or its respective acetylene derivative RiC≡CH.

For the terms "alkyl", "aryl", "aralkyl" and "substituted", reference is made to the corresponding definitions under item (1).

According to this aspect of the invention, a process for preparing 1-alkynylboronates from dihalogenoalkenes is provided, wherein an acetylide carbanion of formula II is formed by adding a strong organometallic base to a compound of formula I. The term "strong organometallic base" as employed herein means an organometallic base having a pKa value of at least 35. The acetylide carbanion of formula II is reacted with compound of formula IX without isolation of the respective acetylene derivative $R_1C$≡CH. Acetylene derivatives $R_1C$≡CH derived from compounds of formula I are normally very volatile, that is their boiling point is close to or within the range of ambient temperatures. Thus, this procedural concept provides for a save and improved operability of the process, since no isolation of said relatively volatile acetylene derivative is necessary. Furthermore, the combination of directly converting compound of formula I to compound of formula II and in situ reaction of said compound of formula II with compound of formula IX provides for an advantageous one pot reaction wherein yields are improved since there is no laborious isolation of intermediate products resulting in yield losses.

Furthermore, this aspect of the invention provides valuable starting materials for the preparation of compounds of formula VI by the process according to items (1) to (12), wherein compound of formula V is preferably obtained by the process according to items (13) to (16).

Preferably, $R_2$, $R_3$ and $R_4$ are the same or $R_2$, $R_3$ cooperatively form a part of a 5- to 10-membered fused or unfused ring, while $R_4$ represents a group different from $R_2$, $R_3$, more preferably $R_2$, $R_3$ and $R_4$ are the same representing substituted or unsubstituted alkyl group, or $R_2$, $R_3$ cooperatively form a part of a 5- to 8-membered fused or unfused ring while $R_4$ represents a substituted or unsubstituted alkyl group, in particular $R_2$, $R_3$ and $R_4$ are the same representing unsubstituted alkyl group, or $R_2$, $R_3$ cooperatively form a part of a 5- to 6-membered ring while $R_4$ represents an unsubstituted alkyl group

(18) The process according to any one of items (13) to (16), wherein the compound of formula III

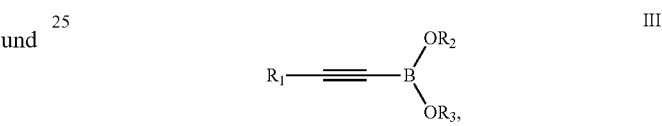
III wherein $R_1$ is hydrogen, substituted or unsubstituted alkyl substituted or unsubstituted aryl, or substituted or unsubstituted aralkyl;
$R_2$ and $R_3$ independently from each other represent substituted or unsubstituted alkyl, substituted or unsubstituted aryl, or substituted or unsubstituted aralkyl, or $R_2$ and $R_3$ cooperatively form a part of a 5- to 10-membered fused or unfused ring, optionally a chiral 5- to 10-membered fused or unfused ring;
is prepared from a compound of formula II

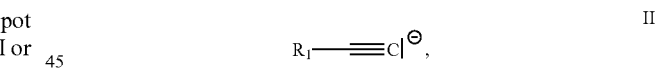
II wherein $R_1$, is as defined above,
by reacting the compound of formula II with a compound of formula IX

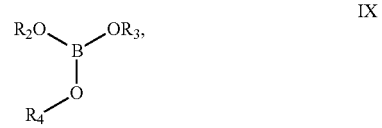
IX wherein $R_2$ and $R_3$ are defined as above,
and $R_4$ represents substituted or unsubstituted alkyl, substituted or unsubstituted aryl, or substituted or unsubstituted aralkyl, wherein $R_4$ is same or different group as $R_2$ and/or $R_3$,
in the presence of a solvent and followed by addition of an acid.

For the terms "alkyl", "aryl", "aralkyl" and "substituted", reference is made to the corresponding definitions under item (1). For the preferred groups represented by $R_2$, $R_3$, and $R_4$, reference is made to the corresponding definitions under item (17).

(19) The process according to item (17) or (18), wherein a solvent is used which is selected from the group consisting of diethylether, i-$Pr_2O$, MTBE, MeTHF and THF, preferably THF.

(20) The process according to any one of items (17) to (19), wherein reacting the compound of formula II with a compound of formula IX is followed by addition of an acid, preferably an inorganic acid, in particular HCl.

(21) The process according to any one of items (17) to (20), wherein the compound of formula II is prepared from a compound of formula I

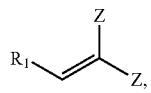

wherein $R_1$ is hydrogen, substituted or unsubstituted alkyl substituted or unsubstituted aryl, or substituted or unsubstituted aralkyl;

Z is selected from the group consisting of Cl, Br and I, preferably Cl; by adding a strong organometallic base, to a solution of a compound of formula I.

In this way, readily available and inexpensive starting materials having the formula I can be used for the synthesis of α-substituted boronic esters of formula VI. α-substituted boronic esters prepared by the Matteson's synthetic route used in prior art are prepared from alkyl or aryl boronic acids from which only few are commercially available, and the esterification reaction of the boronic acid with the respective alcohol needs an additional reaction step. In contrast to that, the present process starts from compounds of formula I, which are obtained from inexpensive and commercially available aldehydes of formula $R_1CHO$, as e.g. described in *Tetrahedron Letters* 2000, 41, 4007-4009.

(22) The process according to item (17) or (21), wherein the strong organometallic base is selected from the group consisting of metal amides and alkyl lithiums, preferably sodium amide, potassium amide, lithium amide, lithium diisopropylamide, methyllithium, butyllithium, hexyllithium and phenyllithium, more preferably butyllithium (n-BuLi) or methyllithium, even more preferably n-BuLi, in particular n-BuLi.

(23) The process according to any one of items (17) to (22), wherein $R_2$ and/or $R_3$ of compound of formula IX is/are chiral, preferably a borolane ring formed by $R_2$ and $R_3$ of compound of formula IX is chiral, more preferably said chiral compounds of formula IX are enantiomerically or diastereomerically pure.

According to this preferred embodiment, $R_2$ and $R_3$ is suitably selected in view of subsequent reaction steps, for example in cases wherein $R_2$ and $R_3$ represent an integral part of the final compound to be produced, or e.g. if $R_2$ and $R_3$ act as directing group(s) in subsequent reaction steps.

(24) The process according to any one of items (1) to (12), wherein the compound of formula VI

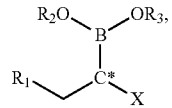

wherein $R_1$, $R_2$ and $R_3$ are defined as above, and X is selected from the group consisting of Cl, Br, I, OCOR' and $OSO_2R'$ in which R' represents substituted or unsubstituted alkyl, substituted or unsubstituted aryl or substituted or unsubstituted aralkyl, and * indicates a chiral center;

is further converted to a compound of formula VIII

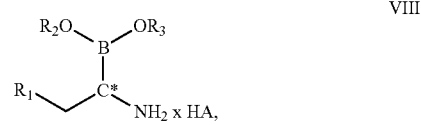

wherein $R_1$, $R_2$ and $R_3$ are defined as above; and

A is an anion selected from the group of anions consisting of $Cl^-$, $Br^-$, $HSO_4^-$, $CH_3COO^-$, $CF_3COO^-$ and $R'SO_3^-$ in which R' represents substituted or unsubstituted alkyl, substituted or unsubstituted aryl or substituted or unsubstituted aralkyl; and

* indicates a chiral center; or free amine thereof, by a process comprising the steps of:

(i) converting the compound of formula VI to compound of formula VII

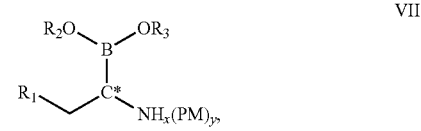

wherein $R_1$, $R_2$ and $R_3$ are defined as above, and

PM is an amino group protecting moiety, wherein PM is selected from the group consisting of tert-butanesulfinyl (SO-t-Bu), tosyl (Ts), p-nitrobenzenesulfonyl (Ns), carbobenzyloxy (Cbz), t-butyloxycarbonyl (Boc), benzyl (Bn), p-methoxybenzyl (MPM), dimethoxybenzyl (Dmb), p-hydroxybenzyl (HBn), 9-phenylfluoren-9-yl (PO, fluorenyl (Flu), diphenylmethyl (DPM), ferrocenylmethyl (Fcm) and 4-Methyltrityl (Mtt), and x=1 and y=1, or PM is $SiR''_3$, wherein R" represents alkyl and x=0 and y=2; and

* indicates a chiral center;

by substituting X of the compound of formula VI with a protected amino group, and (ii) subjecting the compound of formula VII to a cleavage of protecting groups to yield the compound of formula VIII, and (iii) optionally applying enantiomeric resolution in order to obtain enantiomerically pure compound of formula VIII.

According to this beneficial embodiment of the invention, α-substituted boronic esters of formula VI are used as intermediates in the synthesis of α-amino boronic esters having a protected amino group. A term "cleavage of protecting groups" as employed herein means a reaction in which an amino group protecting moiety is cleaved, e.g. hydrogenation or hydrolysis.

(25) The process according to item (24), wherein the amino group protecting moiety PM is selected from the group consisting of SO-t-Bu, $Si(CH_3)_3$ and $Si(CH_2CH_3)_3$.

(26) The process according to item (24) or (25), wherein amino group protecting moiety PM is introduced by using salts of silyl amides as reactant, preferably $((CH_3)_3Si)_2NNa$ (NaHMDS) and $((C_2H_5)_3Si)_2NLi$ (LiHMDS).

(27) The process according to item (24) or (25), wherein A is selected from the group consisting of $Cl^-$ and $CF_3COO^-$, preferably A is $Cl^-$; and/or X is Cl; and/or amino group protecting moiety PM is $Si(CH_3)_3$.

(28) The process according to items (24) to (27), wherein the compound of formula VIII in racemic mixture can be further separated to optically pure (R)-enantiomer or (S)-enantiomer by enantiomeric resolution by crystallization with chiral acids, or by chiral chromatography.

(29) A compound of formula IV

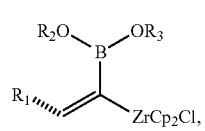

wherein $R_1$ is hydrogen, substituted or unsubstituted alkyl, substituted or unsubstituted aryl, or substituted or unsubstituted aralkyl;

$R_2$ and $R_3$ independently from each other represent substituted or unsubstituted alkyl, substituted or unsubstituted aryl, or substituted or unsubstituted aralkyl, or $R_2$ and $R_3$ cooperatively form a part of a 5- to 10-membered fused or unfused ring, optionally a chiral 5- to 10-membered fused or unfused ring;

with the proviso that $R_1$ does not denote t-Bu or n-Bu.

For the terms "alkyl", "aryl", "aralkyl" and "substituted", reference is made to the corresponding definitions under item (1).

(30) A compound of formula V

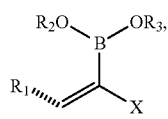

wherein $R_1$ is hydrogen, substituted or unsubstituted alkyl, substituted or unsubstituted aryl, or substituted or unsubstituted aralkyl;

$R_2$ and $R_3$ independently from each other represent substituted or unsubstituted alkyl, substituted or unsubstituted aryl, or substituted or unsubstituted aralkyl, or $R_2$ and $R_3$ cooperatively form a part of a 5- to 10-membered fused or unfused ring, optionally a chiral 5- to 10-membered fused or unfused ring;

and X is selected from the group consisting of Cl, Br, I, OCOR' and $OSO_2R'$ in which R' represents substituted or unsubstituted alkyl, substituted or unsubstituted aryl or substituted or unsubstituted aralkyl;

with the proviso that if X is Cl, Br, I, then $R_1$ does not denote t-Bu.

For the terms "alkyl", "aryl", "aralkyl" and "substituted", reference is made to the corresponding definitions under item (1).

(31) The compounds according to item (29) or (30), wherein $R_1$ is selected from a group consisting of hydrogen, substituted or unsubstituted linear $C_1$-$C_5$-alkyl, substituted or unsubstituted branched $C_1$-$C_5$-alkyl and substituted or unsubstituted $C_3$-$C_8$-cycloalkyl, wherein $R_2$ and $R_3$ are selected from a group consisting of linear substituted or unsubstituted $C_1$-$C_5$-alkyl, substituted or unsubstituted branched $C_1$-$C_5$-alkyl, or $R_2$ and $R_3$ form a part of a 5- to 10-membered fused or unfused ring, optionally a chiral 5- to 10-membered fused or unfused ring; preferably $R_1$ is unsubstituted linear or branched $C_1$-$C_5$-alkyl, and/or $R_2$ and $R_3$ form a part of a 5-membered ring; more preferably, $R_1$ is isopropyl, t-Bu, n-propyl, phenyl, 4-fluorophenyl and/or $R_2$ and $R_3$ cooperatively form a part of a 5-membered ring representing 4,4,5,5-tetramethyl-[1,3,2]dioxaborolane.

(32) A process for producing a N-terminal peptidyl boronic acid derivative of formula X

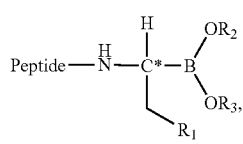

wherein $R_1$ is hydrogen, substituted or unsubstituted alkyl, substituted or unsubstituted aryl, or substituted or unsubstituted aralkyl;

$R_2$ and $R_3$ independently from each other represent substituted or unsubstituted alkyl, substituted or unsubstituted aryl, or substituted or unsubstituted aralkyl, or $R_2$ and $R_3$ cooperatively form a part of a 5- to 10-membered fused or unfused ring, optionally a chiral 5- to 10-membered fused or unfused ring;

peptide comprises 1-6 amino acids coupled to each other by peptide bonds with optionally acylated terminal amino group; and wherein the chiral center * is in its (R) or (S) configuration;

or free acid or ester or anhydride or salt thereof comprising the steps of:

(i) providing a compound of formula VI prepared by a process according to any one of items (1) to (12), (ii) converting said compound of formula VI to compound of formula VIII by a process according to any one of items (24) to (28), and (iii) converting said compound of formula VIII to N-terminal peptidyl boronic acid derivative of formula X, preferably free acid or ester or anhydride or salt thereof.

The term "free acid or ester or anhydride or salt thereof" as used herein means that the boronic acid moiety of the N-terminal peptidyl boronic acid derivative of formula X is in form of a free acid or ester or anhydride or salt.

(33) A process for producing bortezomib (N-(pyrazin-2-yl) carbonyl-L-phenylalanine-L-leucine boronic acid) or ester or anhydride or salt thereof, comprising the steps of:

(i) providing a compound of formula VI prepared by a process according to any one of items (1) to (12), (ii) converting said compound of formula VI to compound of formula VIII by a process according to any one of items (24) to (28), and (iii) converting said compound of formula VIII to bortezomib or ester or anhydride or salt thereof.

The term "ester or anhydride or salt thereof" as used herein means that the boronic acid moiety of bortezomib (N-(pyrazin-2-yl)carbonyl-L-phenylalanine-L-leucine boronic acid) is in form of an ester or anhydride or salt.

According to this preferred embodiment, an advantageous process for producing N-terminal peptidyl boronic acid derivatives of formula X, for example bortezomib is provided, wherein compound of formula VI as the starting material enables the use of inexpensive and readily available starting materials, while the use of toxic and/or hazardous reagents can be avoided.

(34) A process for producing a pharmaceutical composition, comprising the steps of:
(i) preparing N-terminal peptidyl boronic acid derivative of formula X or free acid or ester or anhydride or salt thereof according to item (32), and
(ii) mixing said compound of formula X with at least one excipient.

(35) A process for producing a pharmaceutical composition, comprising the steps of:
(i) preparing bortezomib (N-(pyrazin-2-yl)carbonyl-L-phenylalanine-L-leucine boronic acid) or anhydride or salt thereof according to item (33), and
(ii) mixing said bortezomib with at least one excipient.

(36) Use of a compound of formula V

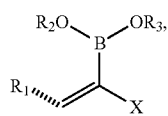

wherein
R$_1$ is hydrogen, substituted or unsubstituted alkyl substituted or unsubstituted aryl, or substituted or unsubstituted aralkyl;
R$_2$ and R$_3$ independently from each other represent substituted or unsubstituted alkyl, substituted or unsubstituted aryl, or substituted or unsubstituted aralkyl, or R$_2$ and R$_3$ cooperatively form a part of a 5- to 10-membered fused or unfused ring, optionally a chiral 5- to 10-membered fused or unfused ring; and X is selected from the group consisting of Cl, Br, I, OCOR' and OSO$_2$R' in which R' represents substituted or unsubstituted alkyl, substituted or unsubstituted aryl or substituted or unsubstituted aralkyl;
with the proviso that if X is Cl, Br, I, then R$_1$ does not denote t-Bu.
in the process for preparation of compound of formula VIII

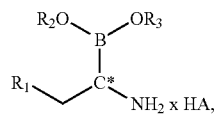

wherein R$_1$, R$_2$ and R$_3$ are defined as above; and
A is an anion selected from the group of anions consisting of Cl$^-$, Br$^-$, HSO$_4^-$, CH$_3$COO$^-$, CF$_3$COO$^-$ and R'SO$_3^-$ in which R' represents substituted or unsubstituted alkyl, substituted or unsubstituted aryl or substituted or unsubstituted aralkyl; and
* indicates a chiral center; or free amine thereof,
and/or in the process for preparation of N-terminal peptidyl boronic acid derivative of formula X or free acid or ester or anhydride or a pharmaceutically acceptable salt thereof, preferably bortezomib or ester or anhydride or a pharmaceutically acceptable salt thereof.

For the terms "alkyl", "aryl", "aralkyl" and "substituted", reference is made to the corresponding definitions under item (1).

(37) Use of a compound of formula IV

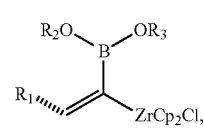

wherein
R$_1$ is hydrogen, substituted or unsubstituted alkyl, substituted or unsubstituted aryl, or substituted or unsubstituted aralkyl;
R$_2$ and R$_3$ independently from each other represent substituted or unsubstituted alkyl, substituted or unsubstituted aryl, or substituted or unsubstituted aralkyl, or R$_2$ and R$_3$ cooperatively form a part of a 5- to 10-membered fused or unfused ring, optionally a chiral 5- to 10-membered fused or unfused ring;
with the proviso that R$_1$ does not denote t-Bu or n-Bu
in the process for preparation of compound of formula VIII

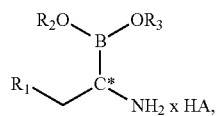

wherein R$_1$, R$_2$ and R$_3$ are defined as above; A is an anion selected from the group of anions consisting of Cl$^-$, Br$^-$, HSO$_4^-$, CH$_3$COO$^-$, CF$_3$COO$^-$ and R'SO$_3^-$ in which R' represents substituted or unsubstituted alkyl, substituted or unsubstituted aryl or substituted or unsubstituted aralkyl;
* indicates a chiral center; or free amine thereof,
and/or in the process for preparation of N-terminal peptidyl boronic acid derivative of formula X or free acid or ester or anhydride or a pharmaceutically acceptable salt thereof, preferably bortezomib or ester or anhydride or a pharmaceutically acceptable salt thereof.

For the terms "alkyl", "aryl", "aralkyl" and "substituted", reference is made to the corresponding definitions under item (1).

(38) The use according to items (36) or (37), wherein R$_1$ is selected from a group consisting of hydrogen, substituted or unsubstituted linear C$_1$-C$_5$-alkyl, substituted or unsubstituted branched C$_1$-C$_5$-alkyl and substituted or unsubstituted C$_3$-C$_8$-cycloalkyl, wherein R$_2$ and R$_3$ are selected from a group consisting of linear substituted or unsubstituted C$_1$-C$_5$-alkyl, substituted or unsubstituted branched C$_1$-C$_5$-alkyl, or R$_2$ and R$_3$ form a part of a 5- to 10-membered fused or unfused ring, optionally a chiral 5- to 10-membered fused or unfused ring; preferably R$_1$ is unsubstituted linear or branched C$_1$-C$_5$-alkyl, and/or R$_2$ and R$_3$ form a part of a 5-membered ring; more preferably, R$_1$ is isopropyl, t-Bu, n-propyl, phenyl, 4-fluorophenyl and/or R$_2$ and R$_3$ cooperatively form a part of a 5-membered ring representing 4,4,5,5-tetramethyl-[1,3,2]dioxaborolane.

(39) A process for preparing a compound of formula VI*

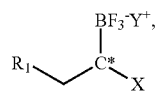
VI* wherein:
$R_1$ is hydrogen, substituted or unsubstituted alkyl, substituted or unsubstituted aryl, or substituted or unsubstituted aralkyl; and
X is selected from the group consisting of Cl, Br, I, $OCOR'$ and $OSO_2R'$ in which R' represents substituted or unsubstituted alkyl, substituted or unsubstituted aryl or substituted or unsubstituted aralkyl;
Y is a cation selected from a group consisting of $Li^+$, $Na^+$, $Cs^+$, $K^+$ and tetraalkylammonium cations, preferably $K^+$ and $(n-Bu)_4N^+$; and
* indicates a chiral center;
wherein said process comprises the steps of:
providing a compound of formula V

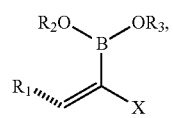
V wherein:
$R_1$ and X are defined as above;
$R_2$ and $R_3$ independently from each other represent substituted or unsubstituted alkyl, substituted or unsubstituted aryl, or substituted or unsubstituted aralkyl, or $R_2$ and $R_3$ cooperatively form a part of a 5- to 10-membered fused or unfused ring, optionally a chiral 5- to 10-membered fused or unfused ring; and
* indicates a chiral center;
(ii) converting said compound of formula V to compound of formula V*

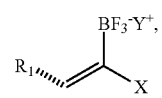
V* wherein:
$R_1$ and X are defined as above; and Y is a cation selected from a group consisting of $Li^+$, $Na^+$, $Cs^+$, $K^+$ and tetraalkylammonium cations, preferably $K^+$ and $(n-Bu)_4N^+$;
by contacting compound of formula V with an aqueous solution of alkaline metal hydrogenfluoride, preferably potassium hydrogenfluoride; optionally converting the thus obtained alkaline metal salt to the respective tetraalkylammonium derivative by contacting with a solution of $(alkyl)_4NOH$, preferably $(n-Bu)_4NOH$; and
(iii) converting said compound of formula V* to compound of formula VI* by hydrogenation.

For the terms "alkyl", "aryl", "aralkyl" and "substituted", reference is made to the corresponding definitions under item (1).

The term "tetraalkylammonium cations" as used herein includes ammonium cations wherein the alkyl components are independently from each other selected from both straight and branched hydrocarbon chains of up to 10 carbons, preferably from 1-5 carbons such as methyl, ethyl, propyl, i-propyl, butyl, t-butyl, i-butyl, pentyl.

Here, the particulars and conditions as defined above, in particular under any one of items (1) to (28) can be applied.

(40) The process according to any one of items (1) to (12), wherein compound of formula VI

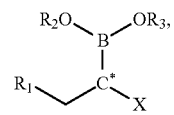
VI wherein $R_1$, $R_2$ and $R_3$ are defined as above, and X is selected from the group consisting of Cl, BrI, $OCOR'$ and $OSO_2R'$ in which R' represents substituted or unsubstituted alkyl, substituted or unsubstituted aryl or substituted or unsubstituted aralkyl, and
* indicates a chiral center;
is further converted to a compound of formula VI*

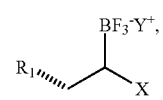
VI* wherein:
$R_1$ and X are defined as above; and Y is a cation selected from a group consisting of $Li^+$, $Na^+$, $Cs^+$, $K^+$ and tetraalkylammonium cations, preferably $K^+$ and $(n-Bu)_4N^+$;
by contacting compound VI with an aqueous solution of alkaline metal hydrogenfluoride, preferably potassium hydrogenfluoride; optionally converting the thus obtained alkaline metal salt to the respective tetraalkylammonium derivative by contacting with a solution of $(alkyl)_4NOH$, preferably $(n-Bu)_4NOH$.

(41) The process according to item (39) or (40), wherein the compound of formula VI*

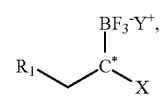
VI* wherein $R_1$, $R_2$ and $R_3$ are defined as above, and X is selected from the group consisting of Cl, Br, I, $OCOR'$ and $OSO_2R'$, and Y is a cation selected from a group consisting of $Li^+$, $Na^+$, $Cs^+$, $K^+$ and tetraalkylammonium cations, preferably $K^+$ and $(n-Bu)_4N^+$; and
* indicates a chiral center;
is further converted to a compound of formula VIII*

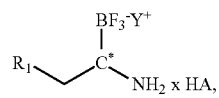
VIII* wherein $R_1$ and Y are defined as above; and
A is an anion selected from the group of anions consisting of $Cl^-$, $Br$, $HSO_4^-$, $CH_3COO^-$, $CF_3COO^-$ and $R'SO_3^-$ in which R' represents substituted or unsubstituted alkyl, substituted or unsubstituted aryl or substituted or unsubstituted aralkyl; and
* indicates a chiral center; or free amine thereof, by a process comprising the steps of:
(i) converting the compound of formula VI* to compound of formula VII*

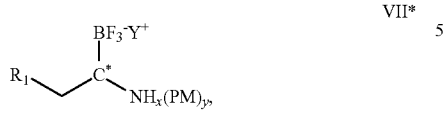

VII* wherein $R_1$ and Y are defined as above, and
PM is an amino group protecting moiety, wherein PM is selected from the group consisting of tert-butanesulfinyl (SO-t-Bu), tosyl (Ts), p-nitrobenzenesulfonyl (Ns), carbobenzyloxy (Cbz), t-butyloxycarbonyl (Boc), benzyl (Bn), p-methoxybenzyl (MPM), dimethoxybenzyl (Dmb), p-hydroxybenzyl (HBn), 9-phenylfluoren-9-yl (Pf), fluorenyl (Flu), diphenylmethyl (DPM), ferrocenylmethyl (Fcm) and 4-Methyltrityl (Mtt), and x=1 and y=1, or PM is $SiR''_3$, wherein R'' represents alkyl and x=0 and y=2; and
* indicates a chiral center;
by substituting X of the compound of formula VI* with a protected amino group, and
(ii) subjecting the compound of formula VII* to a cleavage of protecting groups to yield the compound of formula VIII*, and
(iii) optionally applying enantiomeric resolution in order to obtain enantiomerically pure compound of formula VIII*.

For the term "cleavage of protecting groups", reference is made to the corresponding definition under item (24).
(42) The process according to item (41), wherein the amino group protecting moiety PM is selected from the group consisting of SO-t-Bu, $Si(CH_3)_3$ and $Si(CH_2CH_3)_3$.
(43) The process according to item (41) or (42), wherein amino group protecting moiety PM is introduced by using salts of silyl amides as reactant, preferably $((CH_3)_3Si)_2NNa$ (NaHMDS) and $((C_2H_5)_3Si)_2NLi$ (LiHMDS).
(44) The process according to item (41) or (42), wherein A is selected from the group consisting of $C_1$ and $CF_3COO^-$, preferably A is $Cl^-$; and/or
X is Cl; and/or amino group protecting moiety PM is $Si(CH_3)_3$.
(45) The process according to items (41) to (44), wherein the compound of formula VIII* in racemic mixture can be further separated to optically pure (R)-enantiomer or (S)-enantiomer by enantiomeric resolution by crystallization with chiral acids, or by chiral chromatography.
(46) A compound of formula V*

V* wherein:
$R_1$ is hydrogen, substituted or unsubstituted alkyl, substituted or unsubstituted aryl, or substituted or unsubstituted aralkyl;
X is selected from the group consisting of Cl, Br, I, OCOR' and $OSO_2R'$ in which R' represents substituted or unsubstituted alkyl, substituted or unsubstituted aryl or substituted or unsubstituted aralkyl;
Y is a cation selected from a group consisting of $Li^+$, $Na^+$, $Cs^+$, $K^+$ and tetraalkylammonium cations, preferably $K^+$ and $(n-Bu)_4N^+$; and
* indicates a chiral center;

(47) Use of a compound of formula V*

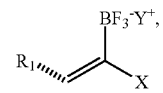

V* wherein:
$R_1$ is hydrogen, substituted or unsubstituted alkyl, substituted or unsubstituted aryl, or substituted or unsubstituted aralkyl;
X is selected from the group consisting of Cl, Br, I, OCOR' and $OSO_2R'$ in which R' represents substituted or unsubstituted alkyl, substituted or unsubstituted aryl or substituted or unsubstituted aralkyl;
Y is a cation selected from a group consisting of $Li^+$, $Na^+$, $Cs^+$, $K^+$ and tetraalkylammonium cations, preferably $K^+$ and $(n-Bu)_4N^+$; and
* indicates a chiral center;
in the process for preparation of compound of formula VIII*

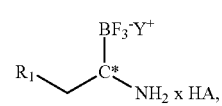

VIII* wherein $R_1$ and Y are defined as above; and
A is an anion selected from the group of anions consisting of $Cl^-$, $Br^-$, $HSO_4^-$, $CH_3COO^-$, $CF_3COO^-$ and $R'SO_3^-$ in which R' represents substituted or unsubstituted alkyl, substituted or unsubstituted aryl or substituted or unsubstituted aralkyl; and
* indicates a chiral center; or free amine thereof.
and/or in the process for preparation of a pharmaceutically active compound.

For the terms "alkyl", "aryl", "aralkyl" and "substituted", reference is made to the corresponding definitions under item (1).
(47) A process for producing a compound of formula XVII

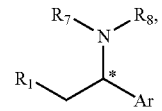

XVII wherein $R_1$ is hydrogen, substituted or unsubstituted alkyl, substituted or unsubstituted aryl, or substituted or unsubstituted aralkyl;
$R_7$ is hydrogen or alkyl;
$R_8$ is hydrogen, —R' or —CO—R' in which R' represents substituted or unsubstituted alkyl, substituted or unsubstituted aryl or substituted or unsubstituted aralkyl;
Ar is substituted or unsubstituted aryl; and
* indicates a chiral center,
wherein said process comprises the steps of:
(i) providing a compound of formula VI prepared by a process according to any one of items (1) to (12) or a compound of formula VI* prepared by a process according to item (39) or (40),
(ii) converting said compound of formula VI to a compound of formula VIII or a free base thereof by a process according to any one of items (24) to (28) or converting said compound of formula VI* to a compound of formula VIII* or a free base thereof by a process according to any one of items (41) to (45), and (iii) converting said compound of formula VIII or VIII* or a free base thereof to a compound of formula XVII by Suzuki-Miyaura cross coupling reaction with a compound of formula XVIII

  XVIII wherein Ar is defined as above, and X" is Cl, Br, I.

As to the meaning of the terms "substituted or unsubstituted", "alkyl", "aryl" and "aralkyl", reference is made to item (1) above.

According to this beneficial embodiment of the invention, α-substituted boronic esters of formula VIII or their trifluoroborate derivatives of formula VIII* are used as intermediates in the synthesis of nitrogen-containing organic molecules by the Suzuki-Miyaura coupling reaction.

DETAILED DESCRIPTION OF THE INVENTION

In the following, the present invention will be described in more detail by preferred embodiments and examples noting, however, that these embodiments, examples are presented for illustrative purposes only and shall not limit the invention in any way.

Reaction Scheme 1 illustrates a preferred embodiment of the process according to the present invention for preparing an α-substituted boronic ester (VI).

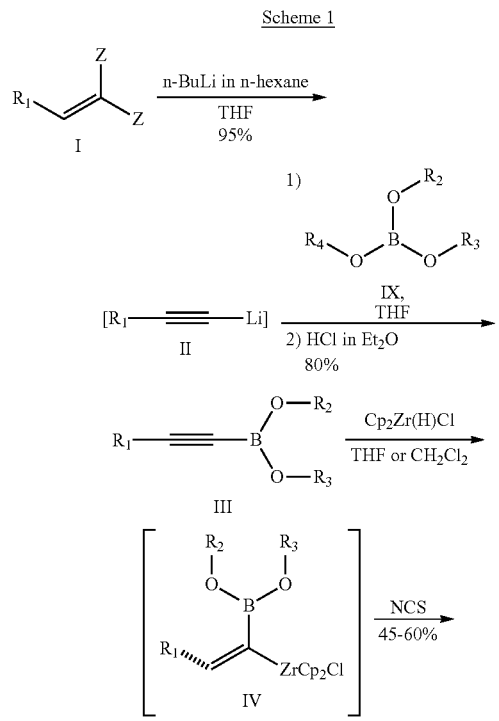

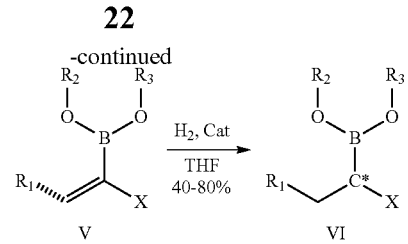

According to the preferred embodiment of Scheme 1 (wherein $R_1$, $R_2$, $R_3$, Z and X are as defined as in the items above), a compound of formula III is prepared by contacting a compound of formula I with a strong organometallic base, e.g. an organolithium reagent such as n-BuLi in n-hexane, to obtain a compound of formula II, which is an acetylide, in this case, since organolithium reagent is used, a lithium acetylide. Then, without isolation of compound of formula II and its respective acetylene derivate $R_1C\equiv CH$, the reaction proceeds in the same reaction vessel by adding a compound of formula IX to yield the compound of formula III. The last step of this reaction is carried out by addition of an acid such as anhydrous HCl. Both steps of the reaction, elimination and addition, to compound III are performed in organic solvent, preferably in THF.

The compound of formula I, a starting material of the synthesis presented in Scheme 1, is available; for example, it can be prepared by synthesis routes known to a person skilled in the art, as e.g. described in *Tetrahedron Letters* 2000, 41, 4007-4009.

Further according to the preferred embodiment illustrated by Scheme 1, a compound of formula V is prepared by subjecting a compound of formula III to hydrozirconation to obtain a compound of formula IV, which is followed by halogenation, preferably in situ halogenation. Hydrozirconation as used herein means forming organozirconocenes using $Cp_2Zr(H)Cl$ (also known as Schwartz reagent), a method well known to a person skilled in the art. Halogenation can be achieved for example by adding various halogen reagents which express positive charge on halogen, preferably N-halogenosuccinimide (e.g. N-chlorosuccinimide, NCS as illustrated in Scheme 1) in situ to a compound of formula IV to yield the compound of formula V. The reaction is carried out in organic solvent such as THF, $CH_2Cl_2$ or DCE, which is later removed under reduced pressure. The reaction mixture is extracted with n-hexane and the residue is purified by chromatography.

Alternatively, halogen introduced subsequent to hydrozirconation as described above, can be optionally further converted to a moiety selected from the group consisting of OCOR' and $OSO_2R'$, wherein R' represents substituted or unsubstituted alkyl, substituted or unsubstituted aryl or substituted or unsubstituted aralkyl, by methods well known from the state of the art. For example, following a protocol of U.S. Pat. No. 4,924,026 a halogen atom, e.g. Cl (compound of formula V with X=Cl in Scheme 1), can be converted to a moiety OCOMe (compound of formula V with X=OCOMe in Scheme 1).

The hydrohalogenation of alkyne boronates via Schwartz intermediates yields de novo formed alkenes, which theoretically exist in two geometrical isomers. Based on the literature data (*J. Am. Chem. Soc.* 1994, 116, 10302-10303) the (E) configuration is supposedly formed predominantly. In the light of the present invention, the determination of the configuration is not necessary, since the β carbon atom is not prochiral in view of the process of our invention.

Further according to the preferred embodiment illustrated by Scheme 1, a compound of formula VI is prepared by hydrogenation/reduction of the compound of formula V. If X in compound of formula V is halogen, then a reduction denotes a homogeneous reduction without dehalogenation. The reaction is performed in an organic solvent, preferably THF, $CH_2Cl_2$, DCE or toluene, in the presence of a catalyst and is carried out in the autoclave under inert atmosphere.

According to another preferred embodiment, in compounds of formulae IV and V, $R_1$ is selected from a group consisting of hydrogen, substituted or unsubstituted linear $C_1$-$C_5$-alkyl, substituted or unsubstituted branched $C_1$-$C_5$-alkyl and substituted or unsubstituted $C_3$-$C_8$-cycloalkyl, wherein $R_2$ and $R_3$ are selected from a group consisting of linear substituted or unsubstituted $C_1$-$C_5$-alkyl, substituted or unsubstituted branched $C_1$-$C_5$-alkyl, or $R_2$ and $R_3$ form a part of a 5- to 10-membered fused or unfused ring, optionally a chiral 5- to 10-membered fused or unfused ring; preferably $R_1$ is unsubstituted linear or branched $C_1$-$C_5$-alkyl, and/or $R_2$ and $R_3$ form a part of a 5-membered ring; more preferably, $R_1$ is isopropyl, t-Bu, n-propyl, phenyl, 4-fluorophenyl and/or $R_2$ and $R_3$ cooperatively form a part of a 5-membered ring representing 4,4,5,5-tetramethyl-[1,3,2]dioxaborolane. The most preferred compounds of formulae IV and V wherein $R_1$ is isopropyl, t-Bu, n-propyl, phenyl or 4-fluorophenyl and $R_2$ and $R_3$ cooperatively form a part of a 5-membered ring representing 4,4,5,5-tetramethyl-[1,3,2]dioxaborolane are depicted in Scheme 2 below, wherein X in compounds of formulae Va to Ve is selected from the group consisting of Cl, Br, I, OCOR' and $OSO_2R'$ in which R' represents substituted or unsubstituted alkyl, substituted or unsubstituted aryl or substituted or unsubstituted aralkyl.

Scheme 2

IVa
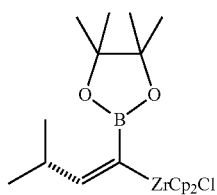

IVb
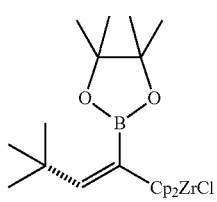

IVc
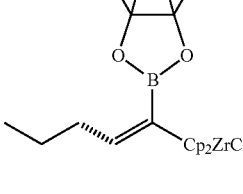

-continued

IVd
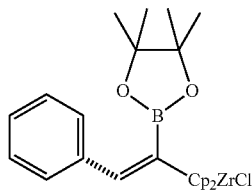

IVe
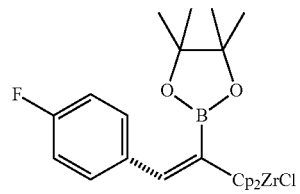

Va
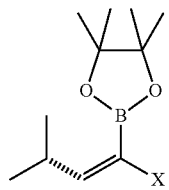

Vb
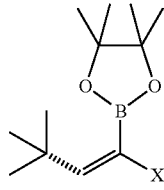

Vc
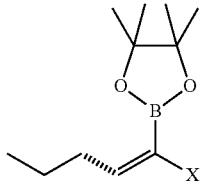

Vd
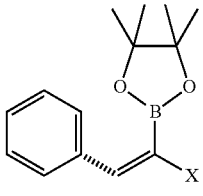

Ve
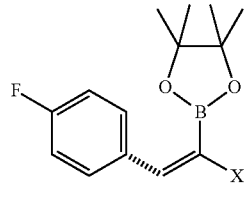

In order that the catalyst substantially contributes to a reduced tendency of dehalogenation, it is selected from transition metal(s), preferably Cu, Co, Ni, Rh, Ru, Pd, Ir. Preferably, the catalyst is metal-(phosphine)-complex, wherein metal is preferably Cu, Rh, Ru, Pd, Ir, more preferably Ir. Preferably, the transition metal is complexed with at least one organic compound containing electron-rich species such as various double bonded compounds and/or free electron pair containing O, N, S, or P species as a ligand. More preferably, the transition metal catalyst has chirality in the ligand and/or at the transition metal atom, or the transition metal complex having chirality is formed in situ by using an achiral procatalyst comprising the transition metal together with a cocatalyst having chirality, such as a chiral ligand. Even more preferably, the aforementioned components having chirality are in enantiomerically or diastereomerically pure form. In particular, at least one of said ligands has chirality, wherein said ligand(s) is/are in enantiomerically or diasteriomerically pure form. Such ligands for instance may include, but are not limited to, (S)-2-(1-(bis(2,6-dimethylphenyl)phosphino)-2-methylpropan-2-yl)-4-tert-butyl-4,5-dihydrooxazole; (S)-4-tert-butyl-2-(2-(diphenylphosphino)phenyl)-4,5-dihydrooxazole; (4S,5S)-4-(2-(dicyclohexylphosphinooxy)-1,3-diphenylpropan-2-yl)-5-methyl-2-phenyl-4,5-dihydrooxazole; (R,R)—P,N-ferrocene oxazoline; (R,R)—P,N-ferrocene imidazoline; benzoyl-(R,R)—P,N-ferrocene imidazoline; (R)-(+)-2,2',6,6'-tetramethoxy-4,4'-bis(diphenylphosphino)-3,3'-bipyridine (i.e. (R)—P-Phos); (S)-2,2',6,6'-tetramethoxy-bis[di(3,5-dimethylphenyl)phosphino]-3,3'-bipyridine (i.e. (S)-Xyl-P-Phos); (R)-4,12-bis(diphenylphosphino)-[2.2]-paracyclophane (i.e. (R)-PhanePhos); 1-(S)—N-methyl-N-(diphenylphosphino)-1-[(R)-(diphenylphosphino)-ferrocenyl]ethylamine (i.e. (S)-MeBoPhos); (R)-2-(1-naphthyl)-8-diphenylphosphino-1-(S)-3,5-dioxa-4-phosphacyclohepta[2,1-1;3,4-a']dinaphthalen-4-yl)-1,2-dihydroquinoline toluene aduct (i.e. (Sa,Rc)-(1-Nph)-quinaphos); (S)-(+)-4,12-bis[di(3,5-dimethylphenyl)phosphino][2.2]paracyclophane (S)-XylPhanePhos); (R)-2,2'-bis(diphenyl-phosphinoamino)-5,5',6,6',7,7',8,8'-octahydro-1,1'-binaphthyl (i.e. (R)—H8-Binam-P). Preferred chiral ligands are (S)-2-(1-(bis(2,6-dimethylphenyl)phosphino)-2-methylpropan-2-yl)-4-tert-butyl-4,5-dihydro-oxazole; (S)-4-tert-butyl-2-(2-(diphenylphosphino)phenyl)-4,5-dihydrooxazole; (4S,5S)-4-(2-(dicyclohexylphosphinooxy)-1,3-diphenylpropan-2-yl)-5-methyl-2-phenyl-4,5-dihydrooxazole; (R,R)—P,N-ferrocene oxazoline; (R,R)—P,N-ferrocene imidazoline and benzoyl-(R,R)—P,N-ferrocene imidazoline.

Scheme 3

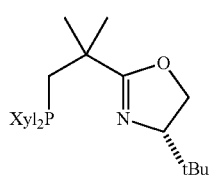

(S)-2-(1-(bis(2,6-dimethylphenyl)
phosphino)-2-methylpropan-2-yl)-
4-tert-butyl-4,5-dihydrooxazole

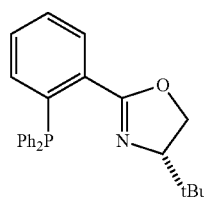

(S)-4-tert-butyl-2-(2-
(diphenylphosphino)phenyl)-
4,5-dihydrooxazole

-continued

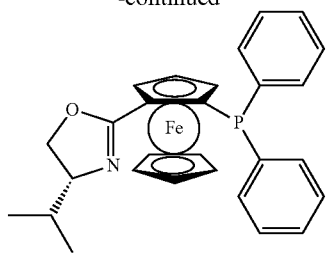

(R,R)-P,N-ferrocene oxazoline

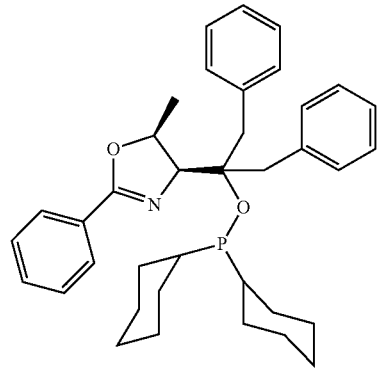

(4S,5S)-4-(2-(dicyclohexyl-phosphinooxy)-
1,3-diphenylpropan-2-yl)-5-methyl-2-phenyl-
4,5-dihydrooxazole

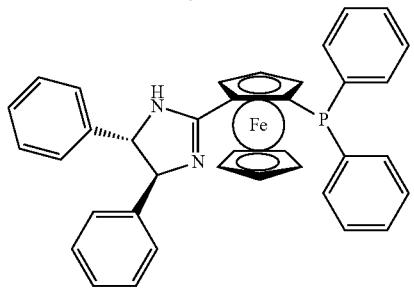

(R,R)-P,N-ferrocene imidazoline

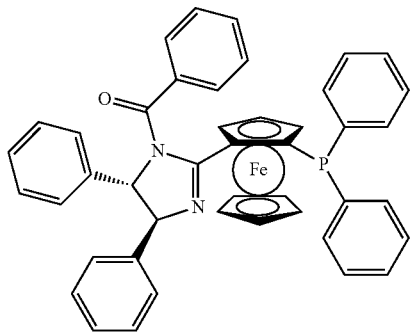

Benzoyl-(R,R)-P,N-ferrocene imidazoline

A non-limiting list of transition metal catalysts having chiral ligands includes (1,5-cyclooctadiene)iridium(I)tetrakis[3,5-bis(trifluoromethyl)phenyl]borate (S)-2-(1-(bis(2,6-dimethylphenyl)phosphino)-2-methylpropan-2-yl)-4-tert-butyl-4,5-dihydrooxazole; (1,5-cyclooctadiene)iridium(I)tetrakis[3,5-bis(trifluoromethyl)phenyl]borate (S)-4-tert-butyl-2-(2-(diphenylphosphino)phenyl)-4,5-dihydrooxazole; (1,5-cyclooctadiene)iridium(I)tetrakis[3,5-bis(trifluoromethyl)phenyl]borate (4S,5S)-4-(2-(dicyclohexylphosphinooxy)-1,3-diphenylpropan-2-yl)-5-methyl-2-phenyl-4,5-dihydro-oxazole; (1,5-cyclooctadiene)

iridium(I)tetrakis[3,5-bis(trifluoromethyl)phenyl]borate (R,R)—P,N-ferrocene oxazoline; (1,5-cyclooctadiene)iridium(I)tetrakis[3,5-bis(trifluoromethyl)phenyl]borate (R,R)—P,N-ferrocene imidazoline; (1,5-cyclooctadiene)iridium(I)tetrakis[3,5-bis(trifluoromethyl)phenyl]borate benzoyl-(R,R)—P,N-ferrocene imidazoline; bis(1,5-cyclooctadiene)diiridium(I)dichloride (R)-(+)-2,2',6,6'-tetramethoxy-4,4'-bis(diphenylphosphino)-3,3'-bipyridine; bis(1,5-cyclooctadiene)diiridium(I)dichloride (S)-2,2',6,6'-tetramethoxy-bis[di(3,5-dimethylphenyl)phosphino]-3,3'-bipyridine; bis(1,5-cyclooctadiene)dirhodium(I)dichloride (S)-2,2',6,6'-tetramethoxy-bis[di(3,5-dimethylphenyl)phosphino]-3,3'-bipyridine; bis(cycloocta-1,5-diene)rhodium(I) tetrafluoroborate (R)-4,12-bis(diphenylphosphino)[2.2]paracyclophane; benzeneruthenium(II) dichloride dimer 1-(S)—N-methyl-N-(diphenylphosphino)-1-[(R)-(diphenylphosphino)-ferrocenyl]ethylamine; bis(2-methylallyl)(1,5-cyclooctadien)ruthenium(II) (S)-(+)-4,12-bis[di(3,5-dimethylphenyl)phosphino]-[2.2]paracyclophane;

Furthermore, the complexes comprising transition metal(s) are preferably used at a molar substrate to catalyst ratio in the range of 5:1 to 100:1, more preferably at a molar substrate to catalyst ratio in the range of 5:1 to 50:1. Particularly preferred catalysts are (1,5-cyclooctadiene)(pyridine)(tricyclohexylphosphine)iridium(I)hexafluoro-phosphate; (1,5-cyclooctadiene)iridium(I)tetrakis[3,5-bis(trifluoromethyl)phenyl]borate (S)-2-(1-(bis(2,6-dimethylphenyl)phosphino)-2-methylpropan-2-yl)-4-tert-butyl-4,5-dihydrooxazole, (1,5-cyclo-octadiene)iridium(I)tetrakis[3,5-bis(trifluoromethyl)phenyl]borate (S)-4-tert-butyl-2-(2-(diphenylphosphino)phenyl)-4,5-dihydrooxazole, (1,5-cyclooctadiene)iridium(I)tetrakis[3,5-bis(trifluoromethyl)phenyl]borate (4S,5S)-4-(2-(dicyclohexylphosphinooxy)-1,3-diphenylpropan-2-yl)-5-methyl-2-phenyl-4,5-dihydrooxazole, (1,5-cyclooctadiene)iridium(I)tetrakis[3,5-bis(trifluoromethyl)phenyl]borate (R,R)—P,N-ferrocene oxazoline, (1,5-cyclooctadiene)iridium(I)tetrakis[3,5-bis(trifluoromethyl)phenyl]borate (R,R)—P,N-ferrocene imidazoline and (1,5-cyclooctadiene)iridium(I)tetrakis[3,5-bis(trifluoromethyl)phenyl]borate benzoyl-(R,R)—P,N-ferrocene imidazoline.

The compound of formula V, the Ir-catalyst and a suitable organic solvent, preferably THF, $CH_2Cl_2$, DCE or toluene are placed in the autoclave under nitrogen atmosphere. The autoclave is sealed and pressurized/depressurized several times with nitrogen, preferably 3 times with about 6 bar of nitrogen, then several times with hydrogen, preferably 3 times with about 6 bar of hydrogen. The mixture is then stirred for a suitable time period, for example 1 to 20 days, preferably for about 1 to 10 days at a temperature from 10° C. to 80° C., more preferably at about 45° C. to 55° C. under about 5 to 20 bar of hydrogen. After this time period the autoclave is cooled to room temperature such as about 20° C. to 25° C. Then, the autoclave is carefully depressurized and the solution obtained is poured into a suitable vessel, preferably a round bottomed flask. The solvent is removed under reduced pressure and the residue is passed through a short column of silica gel, with suitable eluent, preferably n-hexane, to remove the catalyst. Such preferred procedure using an iridium catalyst provides for substantially reduced dehalogenation, preferably dehalogenation occurs in less than 10 molar %, more preferably in less than 5 molar %, most preferably in less than 3 molar %, in particular in less than molar 1% relative to the molar amount of compound of formula VI.

According to another embodiment of the present invention, the racemic mixture of α-(R) and α-(S) isomers of compound VI obtained in the reaction of hydrogenation of compound V, can be further separated by enantiomeric resolution in order to yield optically pure α-(R) or α-(S)-enantiomer. Since enantiomers do not differ in their scalar characteristics, enantiomeric resolution needs a chiral environment. A chiral environment for separation may be provided for example by chiral supporters in a chromatographic column or by adding enantiopure acid/base addition salts in order to form diastereomeric salts which can be separated by crystallisation. In a special case wherein the borolane part of compound of formula VI is chiral, compound of formula VI represents a diastereomer. Since diastereomers differ in their scalar characteristics, diastereomeric compounds of formula VI can be separated without providing a chiral environment, e.g. by crystallization or chromatographic methods on achiral supporters.

Furthermore, in another embodiment, the leaving group X in the compound of formula VI can be exchanged by X' in order to suitably invert the stereochemical configuration at the α-carbon atom of the compound VI by a process wherein the compound of formula VI

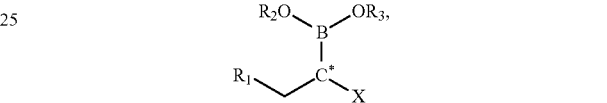

wherein $R_1$, $R_2$ and $R_3$ are defined as above, and X is selected from the group consisting of Cl, Br, I, OCOR' and $OSO_2R'$, is further converted to a compound of formula VI'

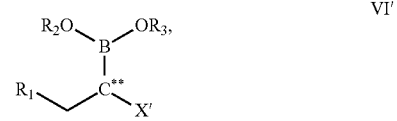

wherein $R_1$, $R_2$ and $R_3$ are defined as above; and

X' is selected from the group consisting of Cl, Br, I, OCOR' and $OSO_2R'$, and X' is not the same as X, wherein a chiral center ** has the opposite stereochemical configuration of the chiral center *.

by applying nucleophilic substitution reaction of type $S_N2$.

When the above presented $S_N2$ reaction is applied to the undesired stereoisomer obtained after chiral chromatography separation of product resulting from hydrogenation reaction which is not completely stereoselective, additional amount of desired steroisomer can be recovered.

Said nucleophilic substitution of type $S_N2$ is also known as "Walden inversion" in the art and is rendered possible since the leaving group X is located at a secondary carbon atom which provides for bimolecular $S_N$ reaction ($S_N2$) and in turn for inversion of the stereochemical configuration at the α-carbon atom of the compound VI. For example, compound VI wherein X=Cl can be transformed to compound VI' (X=I) by methodology described in EP 0 315 574, or compound VI wherein X=Cl can be converted to compound VI' wherein X=$OSO_2Me$ by methodology described in J. Org. Chem. 1987, 52, 5121-5124. X is not the same as X, however, X is selected from the same group as defined for X.

Another preferred aspect of the invention is a process for preparing α-amino boronic ester (VIII) comprising the steps of:
(i) providing a compound of formula VI following the reaction Scheme 1; and
(ii) converting the compound of formula VI to a compound of formula VIII as depicted in Scheme 3.

Scheme 4

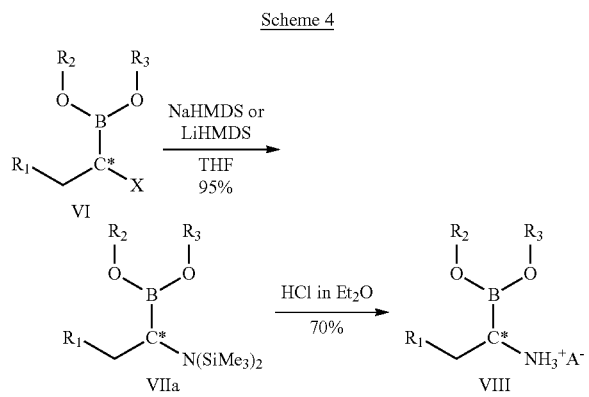

According to the preferred embodiment of Scheme 4 (wherein $R_1$, $R_2$, $R_3$, X and A are as defined as in the items above), a compound of formula VIII, for example about 3.8 mmol, in form of its (R)- or (S)-enantiomer or in form of a mixture of enantiomers, can be prepared by contacting a compound of formula VI dissolved in an organic solvent, preferably THF, with a solution comprising a reagent for substituting X with a protected amino moiety, for example sodium bis(trimethylsilyl)amide (NaHMDS) or lithium bis(trimethylsilyl)amide (LiHMDS), at suitably low temperature such as −60° C. to −10° C., more preferably −40° C. to −30° C., in an inert, preferably argon atmosphere. The solution is warmed to room temperature such as about 20° C. to 25° C., and stirred for a suitable period of time, for example 1 to 15 hours, preferably for about 5 hours. Then, the reaction mixture is evaporated to dryness and the residue is subsequently dissolved in a suitable volume of n-heptane, for example about 10 mL, washed with a suitable volume of $H_2O$, for example about 8 mL, and washed with a suitable volume of saturated aqueous solution of NaCl, for example about 4 mL. The organic phase is then dried over a suitable drying agent, most preferably $MgSO_4$, filtrated and evaporated to dryness. Compound of formula VIIa obtained in such a manner is subsequently further converted into the compound of formula VIII by dissolving the previously obtained residue in a suitable volume of n-heptane, for example 20 mL, and by adding a suitable amount of anhydrous acidic solution, for example anhydrous HCl solution in $Et_2O$, at a suitably low temperature such as −100° C. to −10° C., more preferably −70° C. to −50° C., in an inert, preferably argon atmosphere. The reaction mixture is warmed to room temperature, such as about 20° C. to 25° C., and finally the precipitating solid is isolated from reaction mixture by filtration and washed with $Et_2O$ to give α-amino boronic ester (VIII).

According to another embodiment of the present invention, the racemic mixture of the α-amino boronic ester (VIII) obtained above can be further separated to yield optically pure (R)- or (S)-enantiomer by methods known in the art, such as enantiomeric resolution by crystallization with chiral acids, e.g. malic acid, tartaric acid, mandelic acid, or by chiral chromatography. In the special case wherein the borolane part of compound of formula VIII is chiral, compound of formula VIII represents a diastereomer. Since diastereomers differ in their scalar characteristics, diastereomeric compounds of formula VIII can be separated without providing a chiral environment, e.g. by crystallization or chromatographic methods on achiral supporters.

Enantiomers obtained in such manner can then be subjected to further synthesis steps to yield compounds of general formula X or free acids or esters or anhydrides or salts thereof

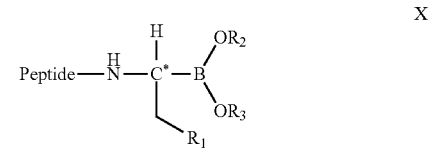

wherein $R_1$ is hydrogen, substituted or unsubstituted alkyl, substituted or unsubstituted aryl, or substituted or unsubstituted aralkyl;
$R_2$ and $R_3$ independently from each other represent substituted or unsubstituted alkyl, substituted or unsubstituted aryl, or substituted or unsubstituted aralkyl, or $R_2$ and $R_3$ cooperatively form a part of a 5- to 10-membered fused or unfused ring, optionally a chiral 5- to 10-membered fused or unfused ring; and
peptide comprises 1-6 amino acids coupled to each other by peptide bonds with optionally acylated terminal amino group, and
wherein the chiral center * is in its (R) or (S) configuration.

For example, the racemic mixture of the intermediate compound of formula VIII, for example 3-methyl-(4,4,5,5-tetramethyl-1,3,2-dioxaborolan-2-yl)butan-1-amine hydrochloride is first separated by enantiomeric resolution method known in the art to give (R)-3-methyl-1-(4,4,5,5-tetramethyl-1,3,2-dioxaborolan-2-yl)butan-1-amine hydrochloride, which can then be subjected to further synthesis steps to yield bortezomib by synthesis routes known to or readily devisable by a person skilled in the art. For example, the following synthesis routes may be applied:

Scheme 5

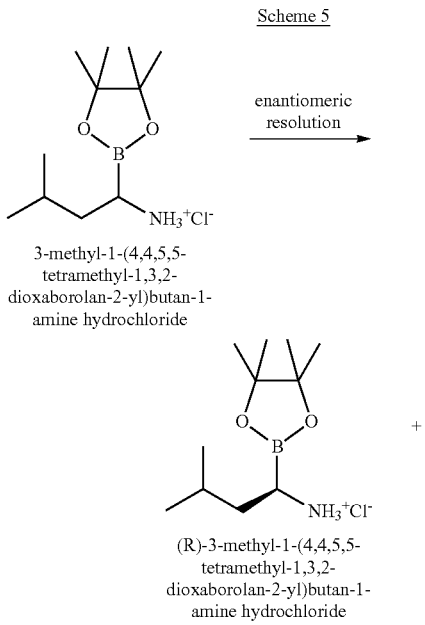

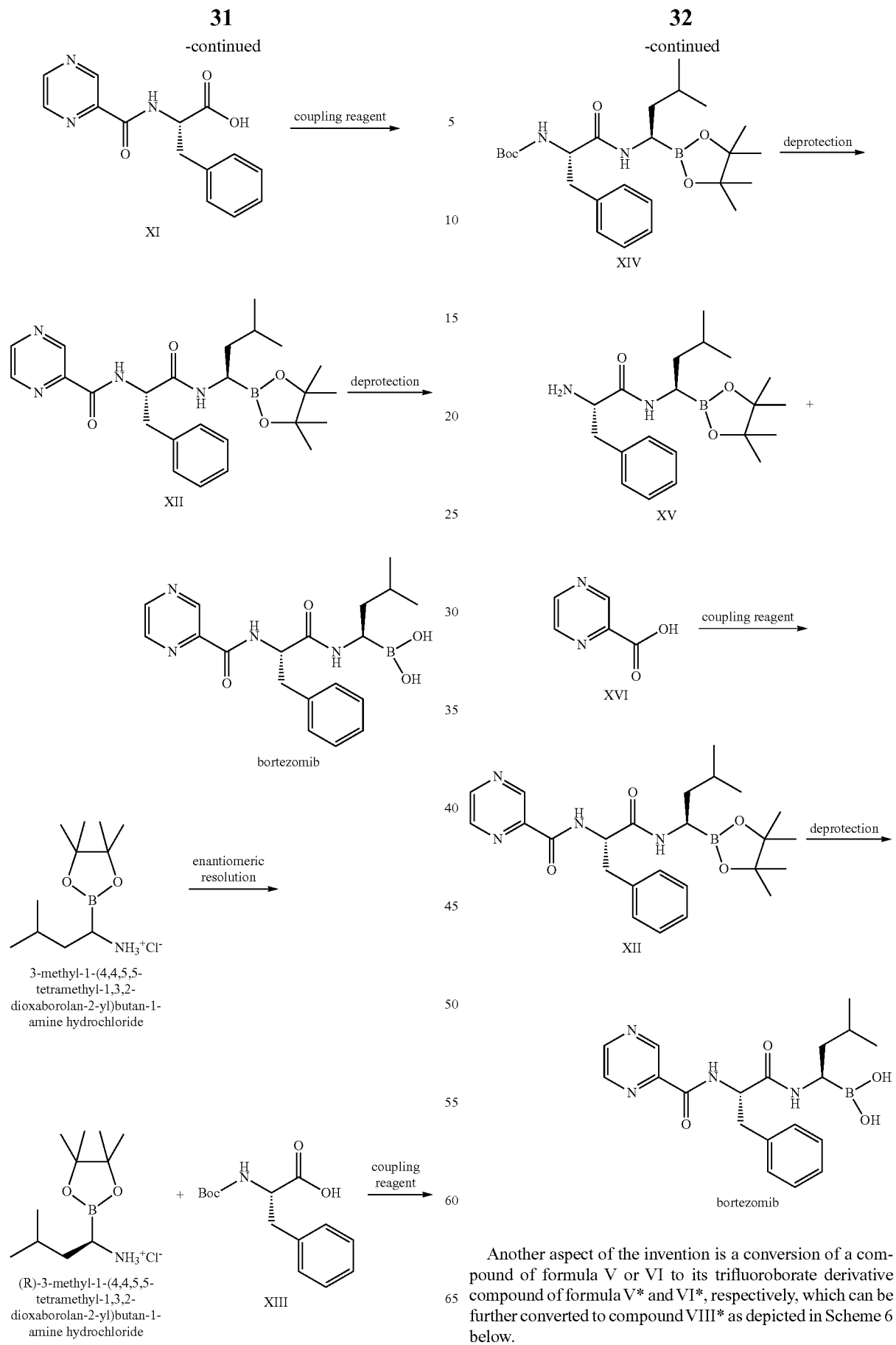
Another aspect of the invention is a conversion of a compound of formula V or VI to its trifluoroborate derivative compound of formula V* and VI*, respectively, which can be further converted to compound VIII* as depicted in Scheme 6 below.

Scheme 6

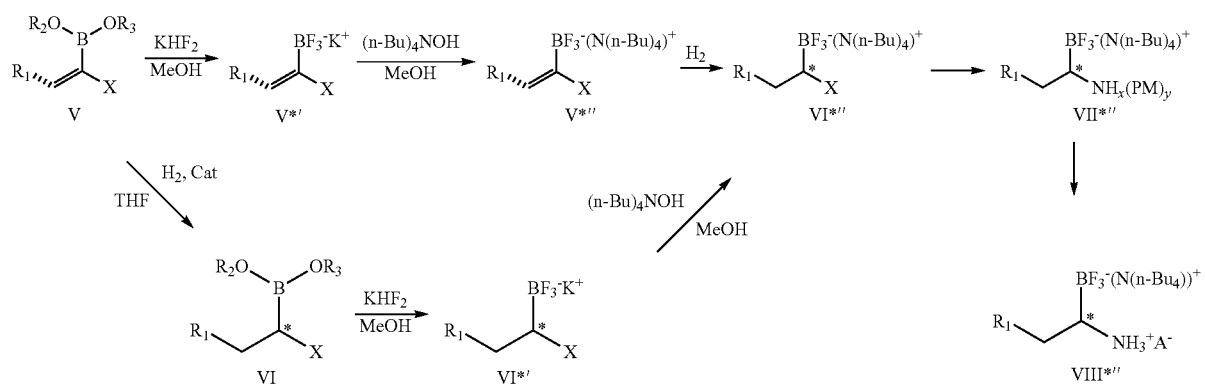

According to the preferred embodiment of Scheme 6, a compound of formula VIII*''' in form of its (R)- or (S)-enantiomer or in form of a mixture of enantiomers, can be prepared by first contacting a compound of formula V dissolved in an organic solvent, preferably MeOH, with aqueous solution of $KHF_2$ (potassium hydrogenfluoride). The obtained potassium salt, can be transformed to other salts, for example to a tetra-n-butylammonium derivative, by reacting the obtained salt with a solution of $(n-Bu)_4NOH$. Thusly obtained V*''' is further converted to VI*''' by hydrogenation. Alternatively, compound VI*''' can be analogously prepared starting from compound VI. In this case, compound VI, which is obtained as described above and depicted in Scheme 1, is taken as a starting point. The obtained compound VI*''' is then contacted with a solution comprising a reagent for substituting X with a protected amino moiety, for example sodium bis(trimethylsilyl)amide (NaHMDS) or lithium bis(trimethylsilyl)amide (LiHMDS), at suitably low temperature such as −60° C. to −10° C., more preferably −40° C. to −30° C., in an inert, preferably argon atmosphere. The solution is warmed to room temperature such as about 20° C. to 25° C., and stirred for a suitable period of time, for example 1 to 15 hours, preferably for about 5 hours. Compound of formula VII*''' can be subsequently further converted into the compound of formula VIII*''' by dissolving compound of formula VII*''' in pure form or in form of crude product derived from the aforementioned preparation method in a suitable volume of THF, and by adding a suitable amount of anhydrous acidic solution, for example anhydrous HCl solution in $Et_2O$, at a suitably low temperature such as −100° C. to −10° C., more preferably −70° C. to −50° C., in an inert, preferably argon atmosphere.

According to another embodiment of the present invention, a process for producing a compound of formula XVII

wherein $R_1$ is hydrogen, substituted or unsubstituted alkyl, substituted or unsubstituted aryl, or substituted or unsubstituted aralkyl;
$R_7$ is hydrogen or alkyl;
$R_8$ is hydrogen, —R' or —CO—R' in which R' represents substituted or unsubstituted alkyl, substituted or unsubstituted aryl or substituted or unsubstituted aralkyl;
Ar is substituted or unsubstituted aryl; and
* indicates a chiral center,
is provided, wherein said process comprises the steps of:
(i) providing a compound of formula VI or VI* prepared as described above,
(ii) converting said compound of formula VI to a compound of formula VIII or a free base thereof or converting said compound of formula VI* to a compound of formula VIII* or a free base thereof as described above, and
(iii) converting said compound of formula VIII or VIII* or a free base thereof to compound of formula XVII by Suzuki-Miyaura cross coupling reaction with a compound of formula XVIII

wherein Ar is defined as above, and X'' is Cl, Br, I.

Further information about a Suzuki-Miyaura coupling reaction is e.g. described in *Chem. Letters* 2009, 38, 664-665.

EXPERIMENTAL PROCEDURES

Example 1a

Synthesis of 4,4,5,5-tetramethyl-2-(3-methylbut-1-ynyl)-1,3,2-dioxaborolane (IIIa)

Scheme 7a

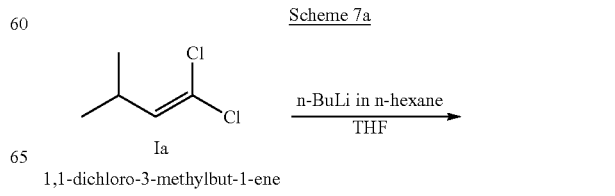

1,1-dichloro-3-methylbut-1-ene

-continued

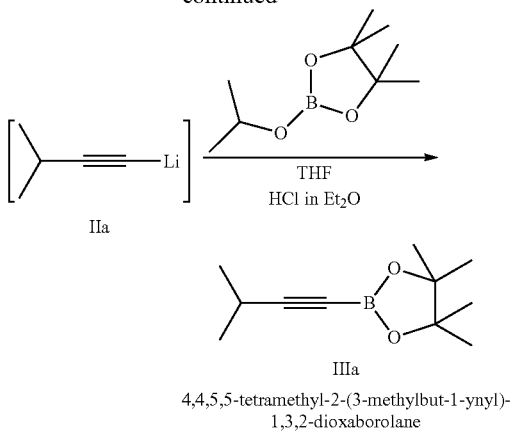

IIa

IIIa
4,4,5,5-tetramethyl-2-(3-methylbut-1-ynyl)-1,3,2-dioxaborolane

To a stirred solution of Ia (7.0 g, 50 mmol) in dry THF (25 mL) at −78° C. was added n-BuLi (1.6 M in n-hexane, 62.5 mL, 100 mmol). After being stirred for 1 hour at −78° C., the reaction mixture was warmed to room temperature and stirred for 1 hour at that temperature. Another flask was charged with 2-isopropoxy-4,4,5,5-tetramethyl-1,3,2-dioxaborolane (7.8 mL, 38 mmol) in dry THF (50 mL) under argon atmosphere, and the reaction mixture was cooled to −78° C. The lithium acetylide from the first flask, which was cooled to −78° C., was slowly added to the second by a double-ended needle. The mixture was stirred at −78° C. for 2 hours, after which anhydrous HCl (100 mmol) was added. Then, reaction mixture was warmed to room temperature. After removal of the precipitated LiCl by filtration and removal of solvents under reduced pressure, the residue was purified by distillation (113-115° C./7 mbar) to afford IIIa (5.9 g, 80%) as an oil.

$^1$H NMR (CDCl$_3$): δ (ppm)=1.15 (d, 6H), 1.25 (s, 12H), 2.45-2.6 (m, 1H).

$^{13}$C NMR (CDCl$_3$): δ (ppm)=21.0, 22.2, 24.5, 83.9.

Starting material Ia was prepared as described in *Tetrahedron Letters* 2000, 41, 4007-4009.

Example 1b

Synthesis of 2-(3,3-dimethylbut-1-ynyl)-4,4,5,5-tetramethyl-1,3,2-dioxaborolane (IIIb)

Scheme 7b

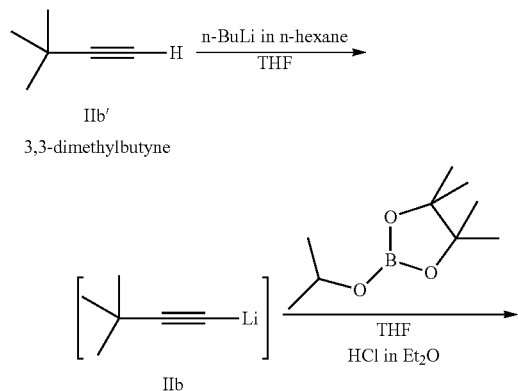

IIb'
3,3-dimethylbutyne

IIb

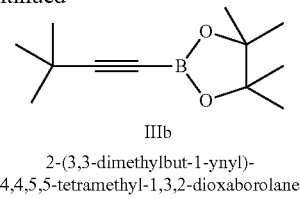

IIIb
2-(3,3-dimethylbut-1-ynyl)-4,4,5,5-tetramethyl-1,3,2-dioxaborolane

To a stirred solution of IIb' (5 mL, 40 mmol) in dry THF (25 mL) at −78° C. was added n-BuLi (2.5 M in n-hexane, 18 mL, 44 mmol). Another flask was charged with 2-isopropoxy-4,4,5,5-tetramethyl-1,3,2-dioxaborolane (8.2 mL, 40 mmol) in dry THF (50 mL) under argon atmosphere, and the reaction mixture was cooled to −78° C. The lithium acetylide from the first flask, which was cooled to −78° C., was slowly added to the second by a double-ended needle. The mixture was stirred at −78° C. for 2 hours, after which anhydrous HCl (44 mmol) was added. Then, reaction mixture was warmed to room temperature. After removal of the precipitated LiCl by filtration and removal of solvents under reduced pressure, the residue was purified by distillation (115-125° C./15 mbar) to afford IIIb (4.3 g, 52%) as a colourless, greasy solid.

$^1$H NMR (CDCl$_3$): δ (ppm)=1.20 (s, 9H), 1.25 (s, 12H).

$^{13}$C NMR (CDCl$_3$): δ (ppm)=24.6, 27.9, 30.4, 84.0.

Example 1c

Synthesis of 4,4,5,5-tetramethyl-2-(pent-1-ynyl)-1,3,2-dioxaborolane (IIIc)

Scheme 7c

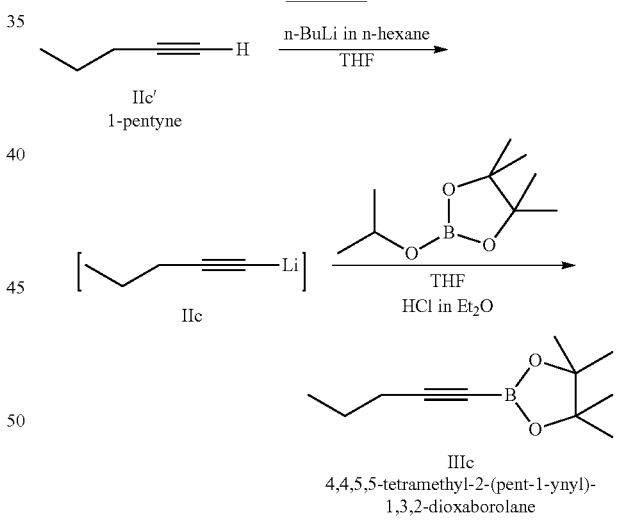

IIc'
1-pentyne

IIc

IIIc
4,4,5,5-tetramethyl-2-(pent-1-ynyl)-1,3,2-dioxaborolane

To a stirred solution of IIc' (5 mL, 51 mmol) in dry THF (25 mL) at −78° C. was added n-BuLi (2.5 M in n-hexane, 22.4 mL, 56 mmol). Another flask was charged with 2-isopropoxy-4,4,5,5-tetramethyl-1,3,2-dioxaborolane (10.4 mL, 51 mmol) in dry THF (50 mL) under argon atmosphere, and the reaction mixture was cooled to −78° C. The lithium acetylide from the first flask, which was cooled to −78° C., was slowly added to the second by a double-ended needle. The mixture was stirred at −78° C. for 2 hours, after which anhydrous HCl (56 mmol) was added. Then, reaction mixture was warmed to room temperature. After removal of the precipitated LiCl by filtration and removal of solvents under reduced pressure, the residue was purified by distillation (115-125° C./15 mbar) to afford IIIc (6.3 g, 64%) as an oil.

$^1$H NMR (CDCl$_3$): δ (ppm)=0.95 (t, 3H), 1.25 (s, 12H), 1.50-1.60 (m, 2H), 2.20 (t, 2H).

$^{13}$C NMR (CDCl$_3$): δ (ppm)=13.4, 21.3, 21.4, 24.45, 24.5, 83.9.

Example 1d

Synthesis of 4,4,5,5-tetramethyl-2-(phenylethynyl)-1,3,2-dioxaborolane (IIId)

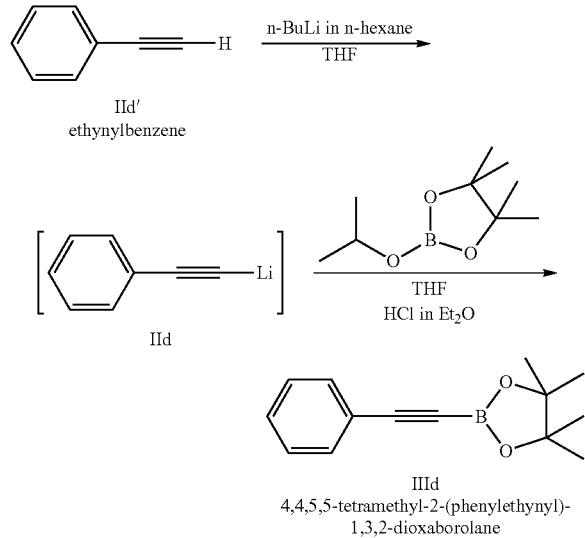

Scheme 7d

To a stirred solution of IId' (10 mL, 91 mmol) in dry THF (50 mL) at −78° C. was added n-BuLi (2.5 M in n-hexane, 40 mL, 100 mmol). Another flask was charged with 2-isopropoxy-4,4,5,5-tetramethyl-1,3,2-dioxaborolane (18.7 mL, 91 mmol) in dry THF (100 mL) under argon atmosphere, and the reaction mixture was cooled to −78° C. The lithium acetylide from the first flask, which was cooled to −78° C., was slowly added to the second by a double-ended needle. The mixture was stirred at −78° C. for 2 hours, after which anhydrous HCl (105 mmol) was added. Then, reaction mixture was warmed to room temperature. After removal of the precipitated LiCl by filtration and removal of solvents under reduced pressure, the residue was purified by distillation (185-200° C./15 mbar) to afford IIId (16.05 g, 76%) as a colourless oil.

$^1$H NMR (CDCl$_3$): δ (ppm)=1.32 (s, 12H), 7.26-7.36 (m, 3H), 7.52 (d, 2H).

$^{13}$C NMR (CDCl$_3$): δ (ppm)=24.6, 84.4, 121.8, 128.2, 129.3, 132.5.

Example 1e

Synthesis of 2-((4-fluorophenyl)ethyl)-4,4,5,5-tetramethyl-1,3,2-dioxaborolane (IIIe)

Scheme 7e

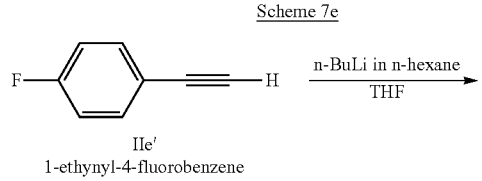

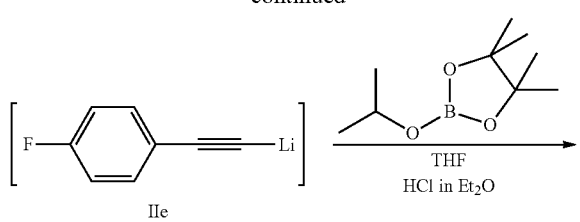

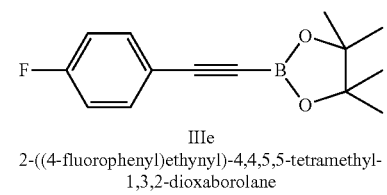

IIIe
2-((4-fluorophenyl)ethynyl)-4,4,5,5-tetramethyl-1,3,2-dioxaborolane

To a stirred solution of IIe' (4.3 mL, 37 mmol) in dry THF (20 mL) at −78° C. was added n-BuLi (2.5 M in n-hexane, 16.3 mL, 41 mmol). Another flask was charged with 2-isopropoxy-4,4,5,5-tetramethyl-1,3,2-dioxaborolane (7.5 mL, 37 mmol) in dry THF (50 mL) under argon atmosphere, and the reaction mixture was cooled to −78° C. The lithium acetylide from the first flask, which was cooled to −78° C., was slowly added to the second by a double-ended needle. The mixture was stirred at −78° C. for 2 hours, after which anhydrous HCl (43 mmol) was added. Then, reaction mixture was warmed to room temperature. After removal of the precipitated LiCl by filtration and removal of solvents under reduced pressure, the residue was purified by distillation (175-185° C./15 mbar) to afford IIIe (7.2 g, 79%) as a colourless greasy solid.

$^1$H NMR (CDCl$_3$): δ (ppm)=1.32 (s, 12H), 7.0 (t, 2H), 7.52 (t, 2H).

$^{13}$C NMR (CDCl$_3$): δ (ppm)=24.6, 84.4, 115.5, 115.8, 117.9, 134.5, 134.6, 161.8, 164.3.

Example 2

Synthesis of 2-(1-chloro-3-methylbut-1-enyl)-4,4,5,5-tetramethyl-1,3,2-dioxaboro-lane (Va)

Scheme 8a

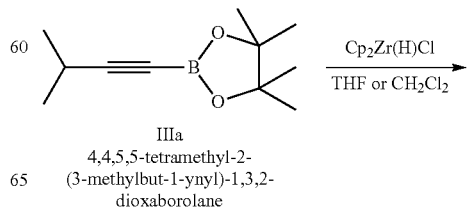

IIIa
4,4,5,5-tetramethyl-2-(3-methylbut-1-ynyl)-1,3,2-dioxaborolane

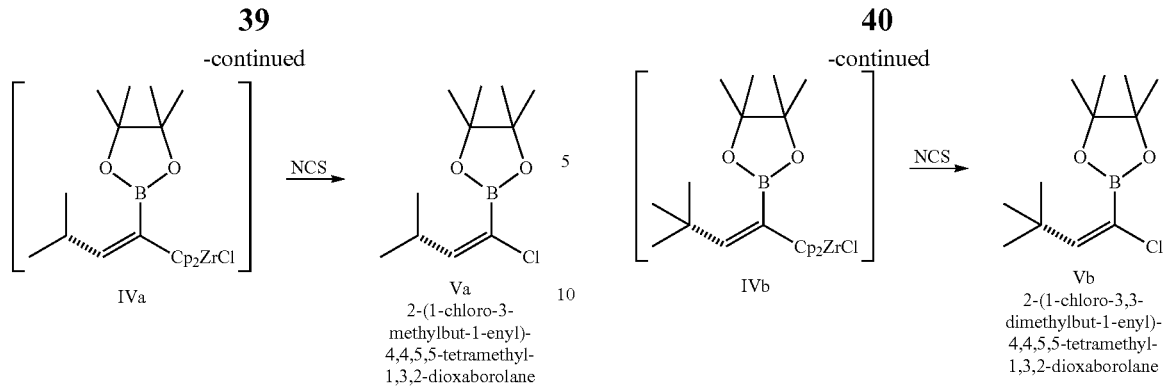

| IVa | Va<br>2-(1-chloro-3-methylbut-1-enyl)-4,4,5,5-tetramethyl-1,3,2-dioxaborolane | IVb | Vb<br>2-(1-chloro-3,3-dimethylbut-1-enyl)-4,4,5,5-tetramethyl-1,3,2-dioxaborolane | a) With THF as a Solvent

A suspension of Cp$_2$Zr(H)Cl (7.3 g, 27 mmol) in dry THF (55 mL) was stirred at room temperature under argon atmosphere. Then, a 48 mL of 0.5 M solution of IIIa (24 mmol) in dry THF was added. The reaction mixture was stirred for 1 hour, resulting in a clear orange solution. Addition of N-chlorosuccinimide (3.6 g, 27 mmol) in situ led to the discharge of the colour of the solution. The solvent was removed under reduced pressure, and n-hexane (5×20 mL) was added to extract the reaction mixture. After removal of solvent under reduced pressure, the residue was purified by chromatography (mobile phase: n-hexane/MTBE=9.5/0.5) to afford Va (2.5 g, 45%) as an oil.

b) With CH$_2$Cl$_2$ as a Solvent

A suspension of Cp$_2$Zr(H)Cl (7.3 g, 27 mmol) in dry CH$_2$Cl$_2$ (55 mL) was stirred at room temperature under argon atmosphere. Then, a 48 mL of 0.5 M solution of IIIa (24 mmol) in CH$_2$Cl$_2$ was added. The reaction mixture was stirred for 1 hour, resulting in a clear orange solution. Addition of N-chlorosuccinimide (3.6 g, 27 mmol) in situ led to the discharge of the colour of the solution. The solvent was removed under reduced pressure, and n-hexane (5×20 mL) was added to extract the reaction mixture. After removal of solvent under reduced pressure, the residue was purified by chromatography (mobile phase: n-hexane/MTBE=9.5/0.5) to afford Va (3.3 g, 60%) as an oil.

$^1$H NMR (CDCl$_3$): δ (ppm)=0.95 (d, 6H), 1.25 (s, 12H), 2.95-3.05 (m, 1H), 6.35 (d, 1H).

$^{13}$C NMR (CDCl$_3$): δ (ppm)=22.8, 24.6, 29.5, 84.2, 156.2.

Example 2c

Synthesis of 2-(1-chloro-3,3-dimethyl-1-enyl)-4,4,5,5-tetramethyl-1,3,2-dioxaborolane (Vb)

Scheme 8b

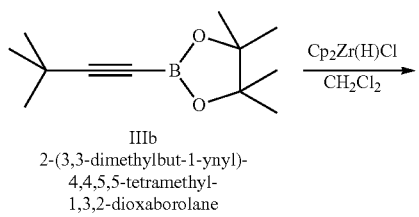

IIIb
2-(3,3-dimethylbut-1-ynyl)-4,4,5,5-tetramethyl-1,3,2-dioxaborolane

A suspension of Cp$_2$Zr(H)Cl (6.8 g, 25 mmol) in dry CH$_2$Cl$_2$ (50 mL) was stirred at room temperature under argon atmosphere. Then, a 43 mL of 0.5 M solution of IIIb (23 mmol) in CH$_2$Cl$_2$ was added. The reaction mixture was stirred for 1 hour, resulting in a clear orange solution. Addition of N-chlorosuccinimide (3.3 g, 25 mmol) in situ led to the discharge of the colour of the solution. The solvent was removed under reduced pressure, and n-hexane (5×20 mL) was added to extract the reaction mixture. After removal of solvent under reduced pressure, the residue was purified by chromatography (mobile phase: n-hexane/MTBE=9.5/0.5) to afford Vb (1.7 g, 30%) as an oil.

$^1$H NMR (CDCl$_3$): δ (ppm)=1.1 (s, 9H), 1.3 (s, 12H), 6.3 (s, 1H).

$^{13}$C NMR (CDCl$_3$): δ (ppm)=24.4, 29.7, 34.8, 84.4, 152.1.

Example 2d

Synthesis of 2-(1-chloro-pent-1-enyl)-4,4,5,5-tetramethyl-1,3,2-dioxaborolane (Vd)

Scheme 8c

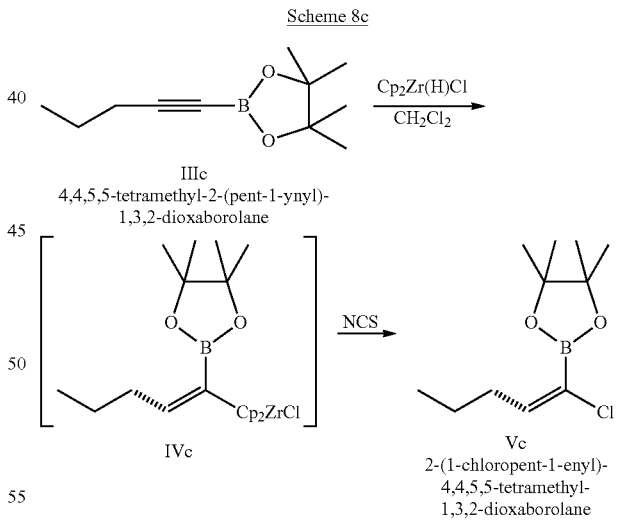

IIIc
4,4,5,5-tetramethyl-2-(pent-1-ynyl)-1,3,2-dioxaborolane

IVc

Vc
2-(1-chloropent-1-enyl)-4,4,5,5-tetramethyl-1,3,2-dioxaborolane

A suspension of Cp$_2$Zr(H)Cl (7.3 g, 27 mmol) in dry CH$_2$Cl$_2$ (54 mL) was stirred at room temperature under argon atmosphere. Then, a 47 mL of 0.5 M solution of IIIc (24.5 mmol) in CH$_2$Cl$_2$ was added. The reaction mixture was stirred for 1 hour, resulting in a clear orange solution. Addition of N-chlorosuccinimide (3.6 g, 27 mmol) in situ led to the discharge of the colour of the solution. The solvent was removed under reduced pressure, and n-hexane (5×20 mL) was added to extract the reaction mixture. After removal of solvent under reduced pressure, the residue was purified by chromatography (mobile phase: n-hexane/MTBE=9.5/0.5) to afford Vc (2.95 g, 48%) as an oil.

$^1$H NMR (CDCl$_3$): δ (ppm)=0.9 (t, 3H), 1.25 (d, 12H), 1.35-1.50 (m, 2H), 2.3 (q, 2H), 6.5 (t, 1H).

$^{13}$C NMR (CDCl$_3$): δ (ppm)=13.4, 22.4, 24.6, 31.9, 84.2, 149.4.

Example 2e

Synthesis of 2-(1-chloro-2-phenylvinyl)-4,4,5,5-tetramethyl-1,3,2-dioxaborolane (Vd)

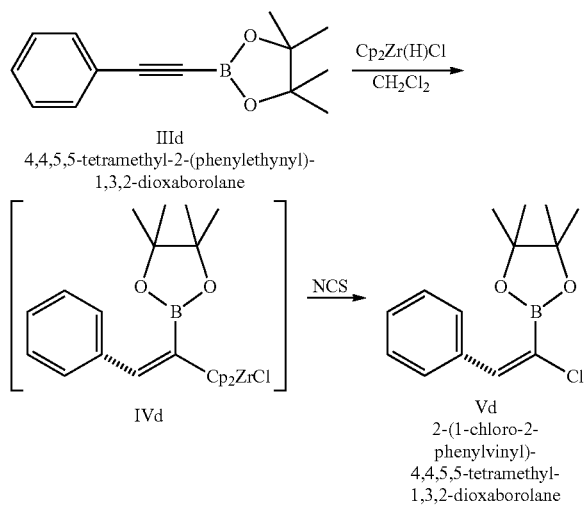

A suspension of Cp$_2$Zr(H)Cl (6.94 g, 26 mmol) in dry CH$_2$Cl$_2$ (51 mL) was stirred at room temperature under argon atmosphere. Then, a 42 mL of 0.5 M solution of IIId (21.3 mmol) in CH$_2$Cl$_2$ was added. The reaction mixture was stirred for 1 hour, resulting in a clear orange solution. Addition of N-chlorosuccinimide (3.5 g, 26 mmol) in situ led to the discharge of the colour of the solution. The solvent was removed under reduced pressure, and n-hexane (5×30 mL) was added to extract the reaction mixture. After removal of solvent under reduced pressure, the residue was purified by chromatography (mobile phase: n-hexane/MTBE=9.5/0.5) to afford Vd (2.5 g, 45%) as an oil.

$^1$H NMR (CDCl$_3$): δ (ppm)=1.33 (s, 12H), 7.24-7.39 (m, 6H).

$^{13}$C NMR (CDCl$_3$): δ (ppm)=24.5, 84.7, 128.1, 128.17, 128.2, 135.5, 143.2.

Example 2f

Synthesis of 2-(1-chloro-2-(4-fluorophenyl)vinyl)-4,4,5,5-tetramethyl-1,3,2-dioxaborolane (Ve)

Scheme 8e

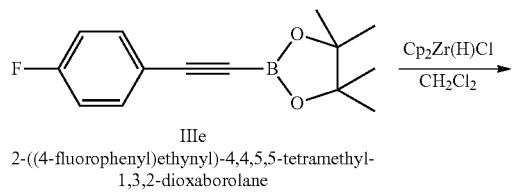

IIIe
2-((4-fluorophenyl)ethynyl)-4,4,5,5-tetramethyl-1,3,2-dioxaborolane

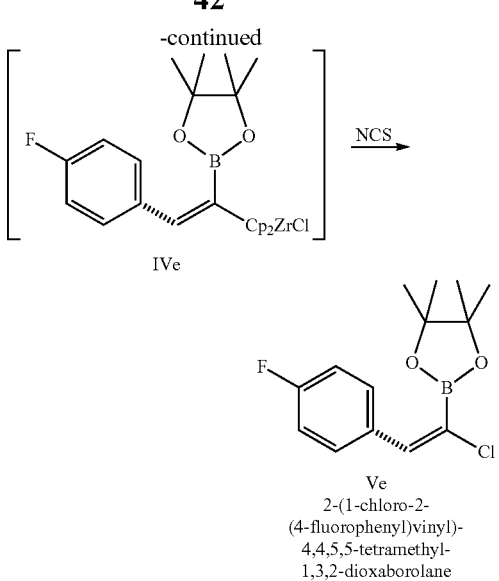

Ve
2-(1-chloro-2-(4-fluorophenyl)vinyl)-4,4,5,5-tetramethyl-1,3,2-dioxaborolane

A suspension of Cp$_2$Zr(H)Cl (4.0 g, 14.8 mmol) in dry CH$_2$Cl$_2$ (35 mL) was stirred at room temperature under argon atmosphere. Then, a 27 mL of 0.5 M solution of IIIe (13.5 mmol) in CH$_2$Cl$_2$ was added. The reaction mixture was stirred for 1 hour, resulting in a clear orange solution. Addition of N-chlorosuccinimide (1.97 g, 14.8 mmol) in situ led to the discharge of the colour of the solution. The solvent was removed under reduced pressure, and n-hexane (5×20 mL) was added to extract the reaction mixture. After removal of solvent under reduced pressure, the residue was purified by chromatography (mobile phase: n-hexane/MTBE=9.5/0.5) to afford Ve (1.1 g, 30%) as an oil.

$^1$H NMR (CDCl$_3$): δ (ppm)=1.32 (s, 12H), 7.0 (t, 2H), 7.32-7.39 (m, 3H).

$^{13}$C NMR (CDCl$_3$): δ (ppm)=24.5, 84.8, 115.0, 115.2, 130.2, 131.6, 131.7, 142.6, 161.5, 163.9.

Example 3a

Synthesis of 2-(1-chloro-3-methylbutyl)-4,4,5,5-tetramethyl-1,3,2-dioxaborolane (VIa)

Scheme 9a

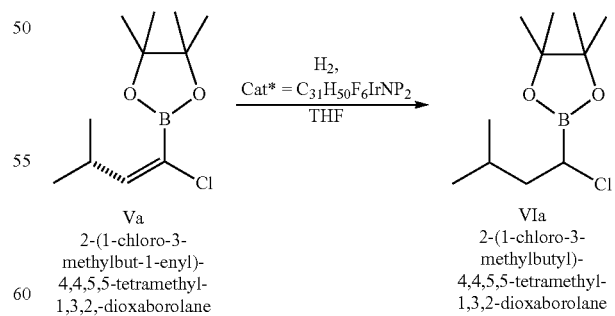

Va
2-(1-chloro-3-methylbut-1-enyl)-4,4,5,5-tetramethyl-1,3,2,-dioxaborolane

VIa
2-(1-chloro-3-methylbutyl)-4,4,5,5-tetramethyl-1,3,2-dioxaborolane

The 75 mL stainless steel autoclave was flushed with nitrogen. The substrate Va (1.15 g, 5.0 mmol), the (1,5-cyclooctadiene)(pyridine)(tricyclohexylphosphine)iridium(I) hexafluorophosphate (80.5 mg, 0.1 mmol) and dry THF (30 mL) were quickly placed in the autoclave under nitrogen atmosphere. The autoclave was sealed and pressurized/depressurized first 3 times with 6 bar of nitrogen, then 3 times with 6 bar of hydrogen. The mixture was stirred for 10 days at 50° C. under 10 bar of hydrogen. Once the autoclave had cooled to room temperature, the autoclave was carefully depressurized, the solution was poured into a round bottomed flask. The solvent was removed under reduced pressure and the residue was passed through a short column of silica gel (eluent=n-hexane) to removed catalyst. The product VIa (0.84 g, 80%) was carried over into next step without further purification.

$^1$H NMR (CDCl$_3$): δ (ppm)=0.9 (m, 6H), 1.3 (s, 1H), 1.45-1.5 (m, 1H), 1.75-1.85 (m, 1H), 1.87-1.95 (m, 1H), 3.5-3.6 (m, 1H).

$^{13}$C NMR (CDCl$_3$): δ (ppm)=22.8, 24.5, 25.5, 31.6, 42.5, 84.3.

Example 3b-d

Synthesis of (R)- or (S)-2-(1-chloro-3-methylbutyl)-4,4,5,5-tetramethyl-1,3,2-dioxaborolane (R- or S-VIa)

Scheme 9b

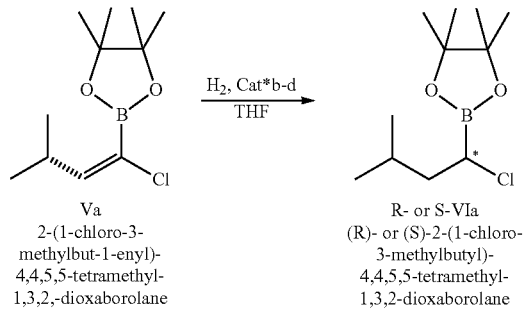

Va
2-(1-chloro-3-methylbut-1-enyl)-4,4,5,5-tetramethyl-1,3,2,-dioxaborolane

R- or S-VIa
(R)- or (S)-2-(1-chloro-3-methylbutyl)-4,4,5,5-tetramethyl-1,3,2-dioxaborolane Cat*
b) [Ir(cod)Cl]$_2$, (R)-P-Phos
c) [Rh(cod)Cl]$_2$, (S)-Xyl-P-Phos
d) [Ir(cod)Cl]$_2$, (S)-Xyl-P-Phos Meaning of the abbreviations used for Catalysts:
Cat*b = Bis(1,5-cyclooctadiene) diiridium(I)dichloride (R)-(+)-2,2',6,6'-Tetramethoxy4,4'-bis(diphenylphosphino)-3,3'-bipyridine;
Cat*c = Bis(1,5-cyclooctadiene) dirhodium(I)dichloride (S)-2,2',6,6'-Tetramethoxy-bis[di(3,5-dimethylphenyl)phosphino]-3,3'-bipyridine;
Cat*d = Bis(1,5-cyclooctadiene) diiridium(I)dichloride (S)-2,2',6,6'-Tetramethoxy-bis[di(3,5-dimethylphenyl)phosphino]-3,3'-bipyridine;

The 75 mL stainless steel autoclave is flushed with nitrogen. The substrate Va (1.15 g, 5.0 mmol), the appropriate catalyst (Cat*b-d; 80.5 mg, 0.1 mmol) and dry THF (30 mL) are quickly placed in the autoclave under nitrogen atmosphere. The autoclave is sealed and pressurized/depressurized first 3 times with 6 bar of nitrogen, then 3 times with 6 bar of hydrogen. The mixture is stirred for 10 days at 50° C. under 10 bar of hydrogen. Once the autoclave is cooled to room temperature, the autoclave is carefully depressurized, the solution is poured into a round bottomed flask. The solvent is removed under reduced pressure and the residue is passed through a short column of silica gel (eluent=n-hexane) to remove the catalyst. The product R- or S-VIa is carried over into next step without further purification. In case the catalysis does not provide for sufficient enantiomeric excess, e.g. enantiomeric excess is less than about 99%, enantiomeric resolution can be applied prior to carrying out the next reaction step.

Example 3e-h

Synthesis of (R)- or (S)-2-(1-chloro-3-methylbutyl)-4,4,5,5-tetramethyl-1,3,2-dioxaborolane (R- or S-VIa)

Scheme 9c

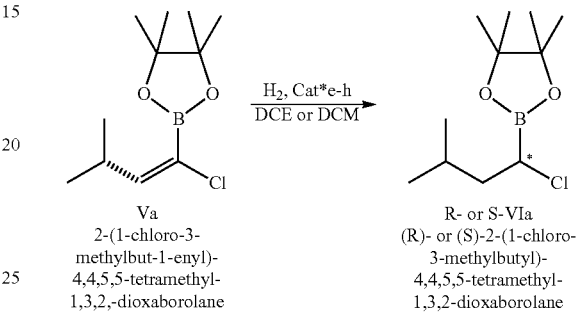

Va
2-(1-chloro-3-methylbut-1-enyl)-4,4,5,5-tetramethyl-1,3,2,-dioxaborolane

R- or S-VIa
(R)- or (S)-2-(1-chloro-3-methylbutyl)-4,4,5,5-tetramethyl-1,3,2-dioxaborolane Cat*e: [Ir(cod)Lig-1]BAr$_F$
Cat*f: [Ir(cod)Lig-2]BAr$_F$
Cat*g: [Ir(cod)Lig-3]BAr$_F$
Cat*h: [Ir(cod)Lig-4]BAr$_F$ Meaning of the abbreviations used:
Cat*e = (1,5-Cyclooctadiene)iridium(I)tetrakis[3,5-bis(trifluoromethyl)phenyl]borate (S)-2-(1-(bis(2,6-dimethylphenyl)phosphino)-2-methylpropan-2-yl-4-tert-butyl-4,5-dihydrooxazole
Cat*f = (1,5-Cyclooctadiene)iridium(I)tetrakis[3,5-bis(trifluoromethyl)phenyl]borate (S)-4-tert-butyl-2-(2-diphenylphosphino)phenyl)-4,5-dihydrooxazole
Cat*g = (1,5-Cyclooctadiene)iridium(I)tetrakis[3,5-bis(trifluoromethyl)phenyl]borate (4S,5S)-4-(2-(dicyclohexylphosphinooxy)-1,3-diphenylpropan-2-yl)-5-methyl-2-phenyl-4,5-dihydrooxazole
Cat*h = (1,5-Cyclooctadiene)iridium(I)tetrakis[3,5-bis(trifluoromethyl)phenyl]borate (R,R)-P,N-ferrocene oxazoline
cod = 1,5-cyclooctadiene
BAr$_F$ = 3,5-bis(trifluoromethyl)phenyl]borate
DCE = 1,2-dichloroethane
DCM = dichloromethane The 15 mL stainless steel autoclave was flushed with nitrogen. The substrate Va (0.5 mmol), the appropriate catalyst (Cat*e-f: 0.01 mmol; Cat*g: 0.02 mmol) and DCE (3 mL) were quickly placed in the autoclave under nitrogen atmosphere. The autoclave was sealed and pressurized/depressurized first 3 times with 6 bar of nitrogen, then 3 times with 6 bar of hydrogen. The mixture was stirred for 20 hours at 50° C. under 20 bar of hydrogen. Once the autoclave was cooled to room temperature, the autoclave was carefully depressurized, the solution was poured into a round bottomed flask. The solvent was removed under reduced pressure and the residue was passed through a short column of silica gel (eluent=n-hexane) to remove the catalyst. The product R- or S-VIa was carried over into next step without further purification.

Parameters of the enantioselective hydrogenation of Va by using catalysts Cat*e-h are presented as follows:

|   | Cat./Metal precursor | Solvent | S/C ratio | Enantiomeric excess (e.e.) [% GC] | Configuration |
|---|---|---|---|---|---|
| 1 | Cat*e | DCE | 50 | 86 | S |
| 2 | Cat*f | DCE | 50 | 58 | S |

-continued

| | Cat./Metal precursor | Solvent | S/C ratio | Enantiomeric excess (e.e.) [% GC] | Configuration |
|---|---|---|---|---|---|
| 3 | Cat*g | DCE | 25 | 71 | R |
| 4 | Cat*h | DCE | 50 | 67 | R |

DCE = 1,2-dichloroethane

Enantiomeric excess was determined by gas chromatography method using GC instrument with flame ionization detector. The column used was Supelco Astec A-TA with dimensions 30 m×0.25 mm×0.12 μm. The injector used was split/splitless, split ratio 30:1, T=250° C. GC conditions: volume of injection=1.0 μL; carrier gas=Helium, constant flow rate 1.5 mL/min; FID temperature=250° C.; Temperature gradient for analytical step=70° C. (66 min) to 130° C. (8 min) at 15° C./min; Temperature gradient for cooling step=130° C. (0 min) to 70° C. (0.1 min) at −15° C./min; Total run time=78 min (82 min with cooling). Retention times of R-VIa and S-VIa were approximately 61 and 64 min, respectively.

Example 3i

Synthesis of (S)-2-(1-chloro-3-methylbutyl)-4,4,5,5-tetramethyl-1,3,2-dioxaborolane (S-VIa)

Scheme 9d

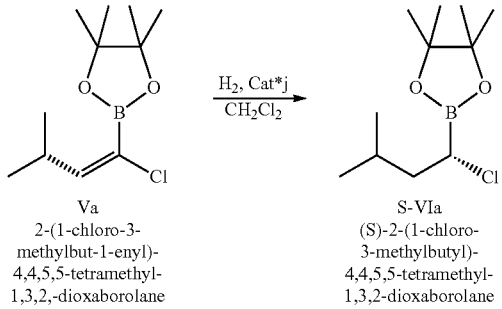

Va
2-(1-chloro-3-methylbut-1-enyl)-4,4,5,5-tetramethyl-1,3,2-dioxaborolane

S-VIa
(S)-2-(1-chloro-3-methylbutyl)-4,4,5,5-tetramethyl-1,3,2-dioxaborolane

Meaning of the abbreviations used:
Cat*j = (1,5-Cyclooctadiene)iridium(I)tetrakis[3,5-bis(trifluoromethyl)phenyl]borate benzoyl-(R,R)-P,N-ferrocene imidazoline The 75 mL stainless steel autoclave was flushed with nitrogen. The catalyst Cat*j (169 mg, 0.17 mmol) was placed in the autoclave under nitrogen atmosphere. The autoclave was sealed and pressurized/depressurized 3 times with 5 bar of nitrogen followed by addition of Va (1.0 g, 4.34 mmol). The system was purged with nitrogen five times and then dry CH₂Cl₂ (25 mL) was added. The system was purged five more times with nitrogen and ten times with hydrogen. The mixture was stirred for 2 days at 50° C. under 5 bar of hydrogen. Once the autoclave had cooled to room temperature, the autoclave was carefully depressurized, the solution was poured into a round bottomed flask. The solvent was removed under reduced pressure and the residue was passed through a short column of silica gel (eluent=n-hexane:EtOAc=9:1) to removed catalyst. The product S-VIa (0.66 g, 66%, 93% ee) was carried over into next step without further purification.

The ee was established using a chiral GC under the following conditions: Column: Chrompack Capillary Column CP-Chirasil-Dex CB, 25 m×0.25 mm×0.25 μm; Injector: split ratio 30, T=250° C.; Carrier gas: helium, constant flow rate 1.5 ml/min; Detector, T=250° C.; Temperature gradient: 60° C. for 40 min, increase 0.5° C./min until 90° C., hold 2 min, decrease 15° C./min until 60° C., hold 1 min; Total run time: 105 min. Retention times: Va: 83.4 min; R-VIa: 93.7 min; S-VIa: 94.8 min.

Example 3j

Synthesis of 2-(1-chloro-3,3-dimethylbutyl)-4,4,5,5-tetramethyl-1,3,2-dioxaborolane (VIb)

Scheme 9e

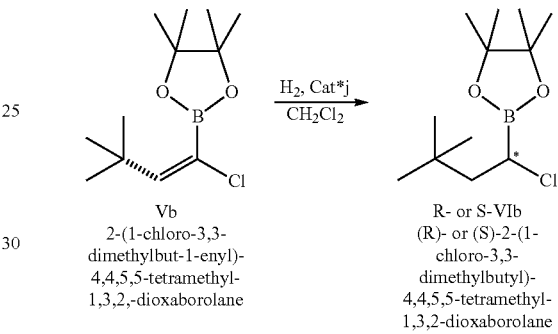

Vb
2-(1-chloro-3,3-dimethylbut-1-enyl)-4,4,5,5-tetramethyl-1,3,2-dioxaborolane

R- or S-VIb
(R)- or (S)-2-(1-chloro-3,3-dimethylbutyl)-4,4,5,5-tetramethyl-1,3,2-dioxaborolane Meaning of the abbreviations used:
Cat*j = (1,5-Cyclooctadiene)iridium(I)tetrakis[3,5-bis(trifluoromethyl)phenyl]borate benzoyl-(R,R)-P,N-ferrocene imidazoline The 75 mL stainless steel autoclave was flushed with nitrogen. The catalyst Cat*j (567 mg, 0.57 mmol) was placed in the autoclave under nitrogen atmosphere. The autoclave was sealed and pressurized/depressurized 3 times with 5 bar of nitrogen followed by addition of Vb (1.0 g, 4.1 mmol). The system was purged with nitrogen five times and then dry CH₂Cl₂ (25 mL) was added. The system was purged five more times with nitrogen and ten times with hydrogen. The mixture was stirred for 2 days at 50° C. under 10 bar of hydrogen. Once the autoclave had cooled to room temperature, the autoclave was carefully depressurized, the solution was poured into a round bottomed flask. The solvent was removed under reduced pressure and the residue was passed through a short column of silica gel (eluent=n-hexane:EtOAc=9:1) to removed catalyst. The product R- or S-VIb (0.7 g, 67%, 93 ee (e2)) was carried over into next step without further purification.

The ee was established using a chiral GC under the following conditions: Column: Chrompack Capillary Column CP-Chirasil-Dex CB, 25 m×0.25 mm×0.25 μm; Injector: split ratio 30, T=250° C.; Carrier gas: helium, constant flow rate 1.0 ml/min; Detector, T=90° C.; Total run time: 60 min. Retention times: e1-VIb: 52.9 min; e2-VIb: 53.9 min; Vb: 54.7 min.

$^1$H-NMR (CDCl₃): δ (ppm)=0.95 (s, 9H), 1.30 (s, 12H), 1.77 (dd, 1H), 1.98 (dd, 1H), 3.47 (dd, 1H).

$^{13}$C-NMR (CDCl₃): δ (ppm)=24.5, 29.6, 31.3, 48.0, 84.2.

Example 3k
Synthesis of (2-(1-chloro-pentyl)-4,4,5,5-tetramethyl-1,3,2-dioxaborolane (VIc)

Scheme 9f

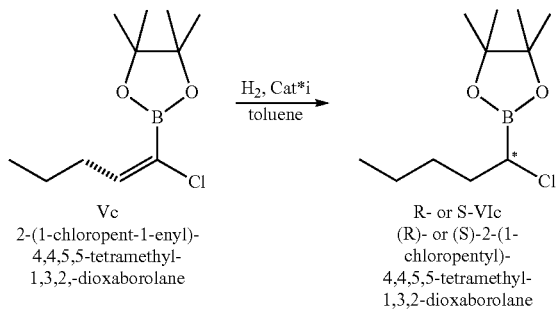

Vc
2-(1-chloropent-1-enyl)-
4,4,5,5-tetramethyl-
1,3,2,-dioxaborolane

R- or S-VIc
(R)- or (S)-2-(1-
chloropentyl)-
4,4,5,5-tetramethyl-
1,3,2-dioxaborolane Meaning of the abbreviations used:
Cat*i = (1,5-Cyclooctadiene)iridium(I)tetrakis[3,5-bis(trifluoromethyl)phenyl]borate (R,R)-P,N-ferrocene imidazoline The 75 mL stainless steel autoclave was flushed with nitrogen. The catalyst Cat*i (183 mg, 0.2 mmol) was placed in the autoclave under nitrogen atmosphere. The autoclave was sealed and pressurized/depressurized 3 times with 5 bar of nitrogen followed by addition of Vc (1.2 g, 5 mmol). The system was purged with nitrogen five times and then dry toluene (30 mL) was added. The system was purged five more times with nitrogen and ten times with hydrogen. The mixture was stirred for 2 days at 80° C. under 10 bar of hydrogen. Once the autoclave had cooled to room temperature, the autoclave was carefully depressurized, the solution was poured into a round bottomed flask. The solvent was removed under reduced pressure and the residue was passed through a short column of silica gel (eluent=n-hexane:EtOAc=9:1) to removed catalyst. The product S-VIc (0.48 g, 40%, 85% ee (e2)) was carried over into next step without further purification.

The ee was established using a chiral GC under the following conditions: Column: Chrompack Capillary Column CP-Chirasil-Dex CB, 25 m×0.25 mm×0.25 μm; Injector: split ratio 30, T=250° C.; Carrier gas: helium, constant flow rate 1.5 ml/min; Detector, T=250° C.; Temperature: 100° C. for 30 min; Total run time: 30 min. Retention times: Vc: 20.0 min; e1-VIc: 21.5 min; e2-VIc: 22.4 min.

$^1$H-NMR (CDCl$_3$): δ (ppm)=0.92 (t, 3H), 1.30 (s, 12H), 1.36 (m, 3H), 1.48 (m, 1H), 1.83 (m, 2H), 3.42 (dd, 1H).

$^{13}$C-NMR (CDCl$_3$): δ (ppm)=14.0, 22.2, 24.6, 29.5, 33.8, 84.3.

Example 3l
Synthesis of 2-(1-chloro-2-phenylethyl)-4,4,5,5-tetramethyl-1,3,2-dioxaborolane (VId)

Scheme 9g

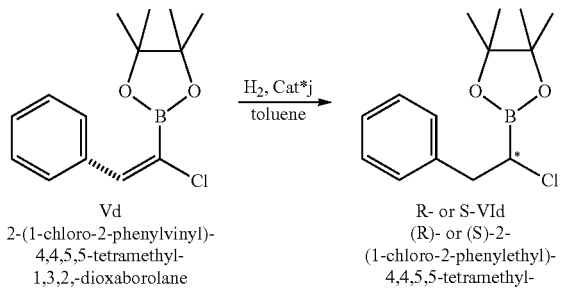

Vd
2-(1-chloro-2-phenylvinyl)-
4,4,5,5-tetramethyl-
1,3,2,-dioxaborolane

R- or S-VId
(R)- or (S)-2-
(1-chloro-2-phenylethyl)-
4,4,5,5-tetramethyl-
1,3,2-dioxaborolane Meaning of the abbreviations used:
Cat*j = (1,5-Cyclooctadiene)iridium(I)tetrakis[3,5-bis(trifluoromethyl)phenyl]borate benzoyl-(R,R)-P,N-ferrocene imidazoline The 75 mL stainless steel autoclave was flushed with nitrogen. The catalyst Cat*j (490 mg, 0.49 mmol) was placed in the autoclave under nitrogen atmosphere. The autoclave was sealed and pressurized/depressurized 3 times with 5 bar of nitrogen followed by addition of Vd (1.3 g, 4.9 mmol). The system was purged with nitrogen five times and then dry CH$_2$Cl$_2$ (30 mL) was added. The system, was purged five more times with nitrogen and ten times with hydrogen. The mixture was stirred for 2 days at 50° C. under 10 bar of hydrogen. Once the autoclave had cooled to room temperature, the autoclave was carefully depressurized, the solution was poured into a round bottomed flask. The solvent was removed under reduced pressure and the residue was passed through a short column of silica gel (eluent=n-hexane:EtOAc=9:1) to removed catalyst. The product R- or S-VId (0.65 g, 50%, 90% ee (e2)) was carried over into next step without further purification.

The ee was established using a chiral GC under the following conditions: Column: Chrompack Capillary Column CP-Chirasil-Dex CB, 25 m×0.25 mm×0.25 μm; Injector: split ratio 30, T=250° C.; Carrier gas: helium, constant flow rate 1.5 ml/min; Detector, T=250° C.; Temperature 110° C.; Total run time: 120 min. Retention times: e1-VId: 103.9 min, e2-VId: 106.7 min, Vd: 113.5 min.

$^1$H-NMR (CDCl$_3$): δ (ppm)=1.25 (s, 6H), 1.27 (s, 6H), 3.12 (dd, 1H), 3.21 (dd, 1H), 3.63 (t, 1H), 7.29 (m, 5H).

$^{13}$C-NMR (CDCl$_3$): δ (ppm)=24.5, 24.6, 40.3, 84.5, 126.8, 128.4, 129.2, 138.4 ppm.

Example 3m
Synthesis of 2-(1-chloro-2-(4-fluorophenyl)ethyl)-4,5,5-tetramethyl-1,3,2-dioxaborolane (VIe)

Scheme 9h

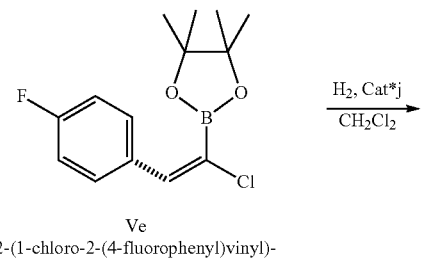

Ve
2-(1-chloro-2-(4-fluorophenyl)vinyl)-
4,4,5,5-tetramethyl-1,3,2-dioxaborolane

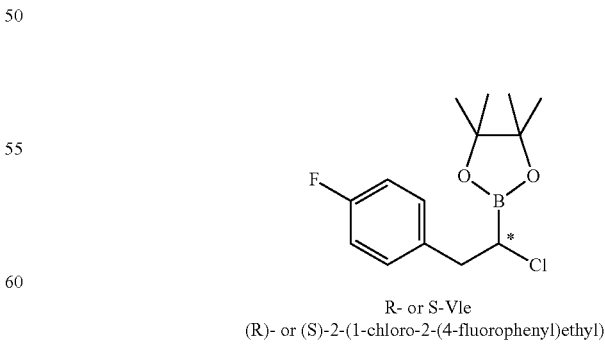

R- or S-VIe
(R)- or (S)-2-(1-chloro-2-(4-fluorophenyl)ethyl)-
4,4,5,5-tetramethyl-1,3,2-dioxaborolane Meaning of the abbreviations used:
Cat*j = (1,5-Cyclooctadiene)iridium(I)tetrakis[3,5-bis(trifluoromethyl)phenyl]borate benzoyl-(R,R)-P,N-ferrocene imidazoline The 75 mL stainless steel autoclave was flushed with nitrogen. The catalyst Cat*j (350 mg, 0.35 mmol) was placed in the autoclave under nitrogen atmosphere. The autoclave was sealed and pressurized/depressurized 3 times with 5 bar of nitrogen followed by addition of Ve (1.0 g, 3.5 mmol). The system was purged with nitrogen five times and then dry $CH_2Cl_2$ (21 mL) was added. The system was purged five more times with nitrogen and ten times with hydrogen. The mixture was stirred for 2 days at 50° C. under 5 bar of hydrogen. Once the autoclave had cooled to room temperature, the autoclave was carefully depressurized, the solution was poured into a round bottomed flask. The solvent was removed under reduced pressure and the residue was passed through a short column of silica gel (eluent=n-hexane:EtOAc=9:1) to removed catalyst. The product R- or S-VIe (0.6 g, 60%, 89% ee (e2)) was carried over into next step without further purification.

The ee was established using a chiral GC under the following conditions: Column: Chrompack Capillary Column CP-Chirasil-Dex CB, 25 m×0.25 mm×0.25 μm; Injector: split ratio 30, T=250° C.; Carrier gas: helium, constant flow rate 1.5 ml/min; Detector, T=250° C.; Temperature 110° C.; Total run time: 120 min. Retention times: Ve+e1-VIe: 109.2 min; e2-VIe: 112.0 min.

$^1$H-NMR (CDCl$_3$): δ (ppm)=1.25 (s, 6H), 1.26 (s, 6H), 3.08 (dd, 1H), 3.16 (dd, 1H), 3.58 (t, 1H), 7.00 (t, 2H), 7.24 (dd, 2H).

$^{13}$C-NMR (CDCl$_3$): δ (ppm)=24.5, 24.6, 39.4, 84.6, 115.1 130.7, 134.0, 161.9.

Example 4a

Synthesis of 3-methyl-1-(4,4,5,5-tetramethyl-1,3,2-dioxaborolan-2-yl)butan-1-amine hydrochloride (leucine boronate hydrochloride, VIIIa)

Scheme 10a

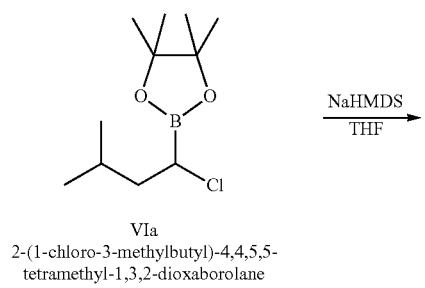

VIa
2-(1-chloro-3-methylbutyl)-4,4,5,5-tetramethyl-1,3,2-dioxaborolane

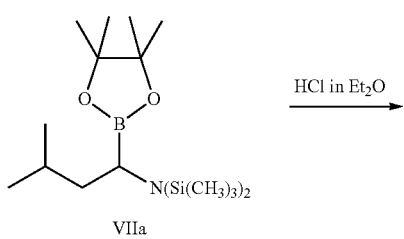

VIIa

-continued

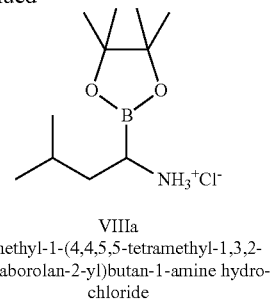

VIIIa
3-methyl-1-(4,4,5,5-tetramethyl-1,3,2-dioxaborolan-2-yl)butan-1-amine hydrochloride To a solution of NaHMDS (1M in THF, 3.8 mL, 3.8 mmol) in dry THF (8 mL) at −35° C. under argon atmosphere was added VIa (0.88 g, 3.8 mmol) dissolved in 8 mL dry THF. The solution was warmed to room temperature and stirred for 5 hours. The reaction mixture was evaporated to dryness. The residue was dissolved in 10 mL of n-heptane, washed with 8 mL H$_2$O and 4 mL saturated aqueous solution of NaCl. The organic phases was dried over MgSO$_4$, filtrated and evaporated to dryness. To a solution of the resulting residue taken up in n-heptane (20 mL), anhydrous HCl (4 eq, solution in Et$_2$O) was added at −60° C. under argon atmosphere. Then, reaction mixture was warmed to room temperature. The precipitating solid was isolated from reaction mixture by filtration and washed with Et$_2$O to afford VIIIa (0.63 g, 70%) as a white solid.

$^1$H NMR (CDCl$_3$): δ (ppm)=0.9 (d, 6H), 1.25 (s, 12H), 1.55-1.65 (m, 1H), 1.7-1.8 (m, 1H), 1.82-1.9 (m, 1H), 2.85-2.95 (m, 1H), 8.2 (s, 3H).

$^{13}$C NMR (CDCl$_3$): δ (ppm)=22.4, 22.4, 24.6, 24.9, 25.0, 38.5, 84.9.

Example 4b

Synthesis of (R)-3-methyl-1-(4,4,5,5-tetramethyl-1,3,2-dioxaborolan-2-yl)butan-1-amine hydrochloride (R-VIIIa)

Scheme 10b

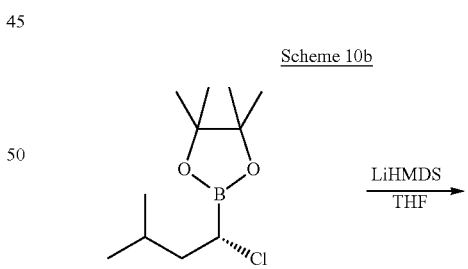

S-VIa
(S)-2-(1-chloro-3-methylbutyl)-4,4,5,5-tetramethyl-1,3,2-dioxaborolane

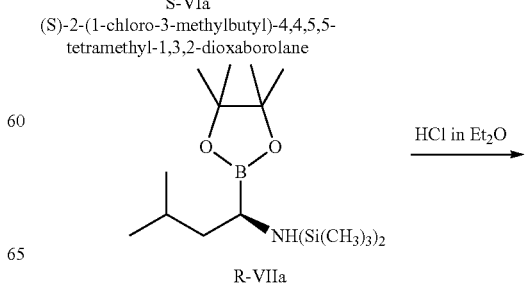

R-VIIa

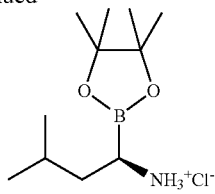

R-VIIIa
(R)-3-methyl-1-(4,4,5,5-tetramethyl-1,3,2-dioxaborolan-2-yl)butan-1-amine hydrochloride

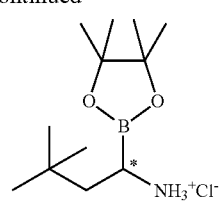

S- or R-VIIIb
(S)- or (R)-3,3-dimethyl-1-(4,4,5,5-tetramethyl-1,3,2-dioxaborolan-2-yl)butan-1-amine hydrochloride Under argon atmosphere a solution of LiHMDS (1M in THF, 2.5 mL, 2.5 mmol) was placed in a flask and cooled at −20° C. S-VIa (0.58 g, 2.5 mmol, example 3e) was dissolved in 5 mL dry THF and added to the LiHMDS solution at −20° C. The mixture was stirred for 1 hour at −20° C. The reaction mixture was warmed to the room temperature and evaporated to dryness. The residue was dissolved in 5 mL of n-heptane, washed with 5 mL H$_2$O and 2 mL saturated aqueous solution of NaCl. The organic phases was dried over MgSO$_4$, filtrated and evaporated to dryness. To a solution of the resulting residue taken up in n-heptane (7 mL), anhydrous HCl (4 eq, solution in Et$_2$O) was added at −60° C. under argon atmosphere. Then, reaction mixture was warmed to room temperature. The precipitating solid was isolated from reaction mixture by filtration and washed with Et$_2$O to afford R-VIIIa (0.33 g, 56%, 92.5% ee) as a white solid.

Under argon atmosphere a solution of LiHMDS (1M in THF, 1.9 mL, 1.9 mmol) was placed in a flask and cooled at −20° C. R- or S-VIb (0.47 g, 1.9 mmol) was dissolved in 4 mL dry THF and added to the LiHMDS solution at −20° C. The mixture was stirred for 1 hour at −20° C. The reaction mixture was warmed to the room temperature and evaporated to dryness. The residue was dissolved in 5 mL of n-heptane, washed with 5 mL H$_2$O and 2 mL saturated aqueous solution of NaCl. The organic phases was dried over MgSO$_4$, filtrated and evaporated to dryness. To a solution of the resulting residue taken up in n-heptane (5 mL), anhydrous HCl (4 eq, solution in Et$_2$O) was added at −60° C. under argon atmosphere. Then, reaction mixture was warmed to room temperature. The precipitating solid was isolated from reaction mixture by filtration and washed with Et$_2$O to afford S- or R-VIIIb (0.25 g, 50%) as a white solid.

$^1$H NMR (CDCl$_3$): δ (ppm)=0.98 (s, 9H), 1.32 (s, 12H), 1.73-1.88 (m, 2H), 2.88 (m, 1H), 8.18 (s, 3H).

$^{13}$C NMR (CDCl$_3$): δ (ppm)=24.8, 25.0, 29.7, 30.5, 43.8, 85.0.

Example 4c

Synthesis of 3,3-dimethyl-1-(4,4,5,5-tetramethyl-1,3,2-dioxaborolan-2-yl)butan-1-amine hydrochloride (VIIIb)

Example 4d

Synthesis of 1-(4,4,5,5-tetramethyl-1,3,2-dioxaborolan-2-yl)pentan-1-amine hydrochloride (VIIIc)

Scheme 10c

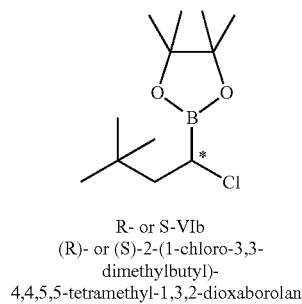

R- or S-VIb
(R)- or (S)-2-(1-chloro-3,3-dimethylbutyl)-4,4,5,5-tetramethyl-1,3,2-dioxaborolane

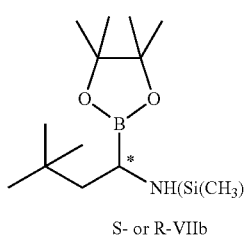

S- or R-VIIb

Scheme 10d

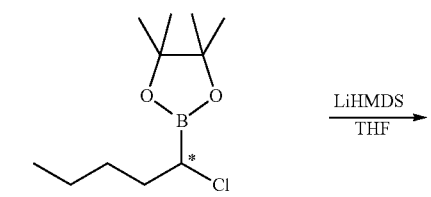

R- or S-VIc
(R)- or (S)-2-(1-chloropentyl)-4,4,5,5-tetramethyl-1,3,2-dioxaborolane

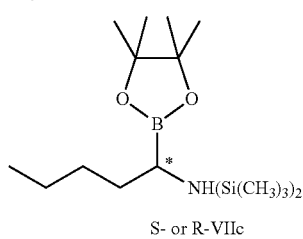

S- or R-VIIc

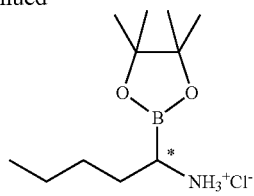

S- or R-VIIIc
(S)- or (R)-1-(4,4,5,5-tetramethyl-1,3,2-
dioxaborolan-2-yl)
pentan-1-amine hydrochloride Under argon atmosphere a solution of LiHMDS (1M in THF, 1.9 mL, 1.9 mmol) was placed in a flask and cooled at −20° C. R- or S-VIc (0.47 g, 1.9 mmol) was dissolved in 4 mL dry THF and added to the LiHMDS solution at −20° C. The mixture was stirred for 1 hour at −20° C. The reaction mixture was warmed to the room temperature and evaporated to dryness. The residue was dissolved in 5 mL of n-heptane, washed with 5 mL H$_2$O and 2 mL saturated aqueous solution of NaCl. The organic phases was dried over MgSO$_4$, filtrated and evaporated to dryness. To a solution of the resulting residue taken up in n-heptane (5 mL), anhydrous HCl (4 eq, solution in Et$_2$O) was added at −60° C. under argon atmosphere. Then, reaction mixture was warmed to room temperature. The precipitating solid was isolated from reaction mixture by filtration and washed with Et$_2$O to afford S- or R-VIIIc (0.25 g, 50%) as a white solid.

$^1$H NMR (CDCl$_3$): δ (ppm)=0.88 (t, 3H), 1.29 (s, 12H), 1.31-1.55 (m, 4H), 1.77-1.90 (m, 2H), 2.84-2.94 (m, 1H), 8.16 (s, 3H).

$^{13}$C NMR (CDCl$_3$): δ (ppm)=13.8, 22.3, 24.6, 24.9, 28.5, 29.2, 37.5, 85.0.

Example 4e

Synthesis of 2-phenyl-1-(4,4,5,5-tetramethyl-1,3,2-dioxaborolan-2-yl)ethanamine hydrochloride (VIIId

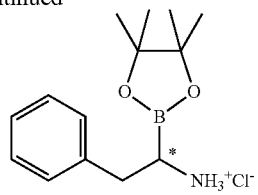

S- or R-VIIId
(S)- or (R)-2-phenyl-1-(4,4,5,5-tetramethyl-
1,3,2-dioxaborolan-2-yl)
ethanamine hydrochloride Under argon atmosphere a solution of LiHMDS (1M in THF, 2.36 mL, 2.36 mmol) was placed in a flask and cooled at −20° C. R- or S-VId (0.6 g, 2.36 mmol) was dissolved in 5 mL dry THF and added to the LiHMDS solution at −20° C. The mixture was stirred for 1 hour at −20° C. The reaction mixture was warmed to the room temperature and evaporated to dryness. The residue was dissolved in 5 mL of n-heptane, washed with 5 mL H$_2$O and 2 mL saturated aqueous solution of NaCl. The organic phases was dried over MgSO$_4$, filtrated and evaporated to dryness. To a solution of the resulting residue taken up in n-heptane (5 mL), anhydrous HCl (4 eq, solution in Et$_2$O) was added at −60° C. under argon atmosphere. Then, reaction mixture was warmed to room temperature. The precipitating solid was isolated from reaction mixture by filtration and washed with Et$_2$O to afford S- or R-VIIId (0.33 g, 50%) as a white solid.

$^1$H NMR (CDCl$_3$): δ (ppm)=1.24 (s, 12H), 3.24 (s, 3H), 7.21-7.41 (m, 5H), 8.22 (s, 3H).

$^{13}$C NMR (CDCl$_3$): δ (ppm)=24.7, 24.9, 35.4, 85.2, 105.0, 127.2, 128.7, 129.6, 136.4.

Example 4f

Synthesis of 2-(4-fluorophenyl)-1-(4,4,5,5-tetramethyl-1,3,2-dioxaborolan-2-yl)ethanamine hydrochloride (VIIIe)

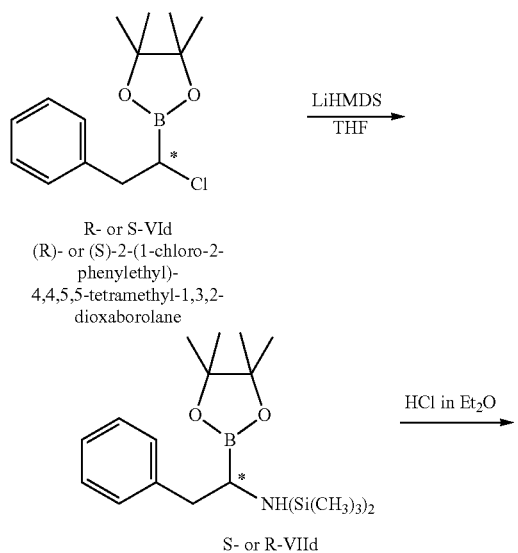

Scheme 10e

R- or S-VId
(R)- or (S)-2-(1-chloro-2-
phenylethyl)-
4,4,5,5-tetramethyl-1,3,2-
dioxaborolane S- or R-VIId

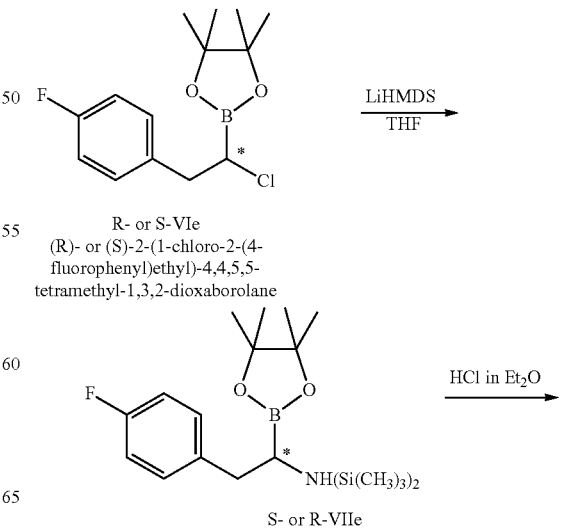

Scheme 10f

R- or S-VIe
(R)- or (S)-2-(1-chloro-2-(4-
fluorophenyl)ethyl)-4,4,5,5-
tetramethyl-1,3,2-dioxaborolane S- or R-VIIe

55
-continued

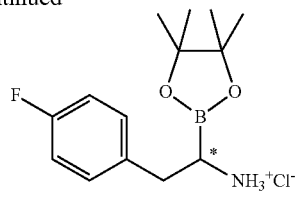

S- or R-VIIIe
(S)- or (R)-2-(4-fluorophenyl)-1-
(4,4,5,5-tetramethyl-1,3,2-
dioxaborolan-2-yl)ethanamine
hydrochloride Under argon atmosphere a solution of LiHMDS (1M in THF, 2.36 mL, 2.36 mmol) was placed in a flask and cooled at −20° C. R- or S-VIe (0.6 g, 2.36 mmol) was dissolved in 5 mL dry THF and added to the LiHMDS solution at −20° C. The mixture was stirred for 1 hour at −20° C. The reaction mixture was warmed to the room temperature and evaporated to dryness. The residue was dissolved in 5 mL of n-heptane, washed with 5 mL H$_2$O and 2 mL saturated aqueous solution of NaCl. The organic phases was dried over MgSO$_4$, filtrated and evaporated to dryness. To a solution of the resulting residue taken up in n-heptane (5 mL), anhydrous HCl (4 eq, solution in Et$_2$O) was added at −60° C. under argon atmosphere. Then, reaction mixture was warmed to room temperature. The precipitating solid was isolated from reaction mixture by filtration and washed with Et$_2$O to afford S- or R-VIIIe (0.33 g, 50%) as a white solid.

$^1$H NMR (CDCl$_3$): δ (ppm)=1.29 (s, 12H), 3.15-3.28 (m, 3H), 7.0 (t, 2H), 7.37 (t, 2H), 8.19 (s, 3H).

$^{13}$C NMR (CDCl$_3$): δ (ppm)=24.7, 24.9, 85.33, 115.4, 115.7, 131.2, 131.3, 132.2, 160.9, 163.3.

Example 5a

Preparation of catalysts Car-b-d: The appropriate phosphine ligand (1.1 eq) and the metal precursor (1.0 eq) are stirred in dry THF under nitrogen atmosphere for 30 min at room temperature. The solvent is removed by evaporation and the solid is purified by flash column chromatography using hexane/CH$_2$Cl$_2$ 1/1 to afford Cat*b-d

Example 5b

Catalysts Car-e-g can be prepared as described in *Adv. Synth. Catal.*, 2001, 343, 450-454: To a two-necked flask fitted with condenser is added chiral P,N-ligand (Lig-1-Lig-3; 2 eq), [Ir(cod)Cl]$_2$ (1 eq) and CH$_2$Cl$_2$. The mixture is heated under nitrogen atmosphere to reflux for 1 hour. After the mixture is cooled to room temperature, Na[BAr$_F$] (3 eq) is added followed by H$_2$O, and the resulting two-phase mixture is stirred vigorously for 10 min. The layers are separated, and the aqueous layer extracted with further portions of CH$_2$Cl$_2$ (2×). The combined organic extracts are washed with H$_2$O and evaporated. The residue is taken up in EtOH and crystallized by slow addition of H$_2$O to give appropriate catalyst.

56
Example 5c

Catalyst Cat*i Having the Structural Formula

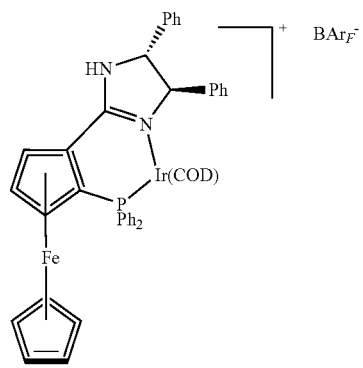

Cat*i was prepared following the synthetic sequence detailed in Scheme 11a. Starting from commercially available ferrocenyl carboxylic acid, the oxazoline ring was installed in two steps (a, b) following the protocol described in *Tetrahedron Asymmetry* 1996, 7, 1419-1430 and *J. Org. Chem.* 1995, 61, 4937-4943. The addition of the diphenyl phosphine (step c) was also carried out following above mention procedures. In order to build the imidazoline ring from the corresponding oxazoline (PL-4), the procedure described in the patent application US 2007/0244319 A1 was followed. The Ir complex was then prepared according to the general protocol described by Pfaltz for the synthesis of P,N—Ir catalysts, *Adv. Synth. Catal.* 2001, 343, 450-454.

Scheme 11a

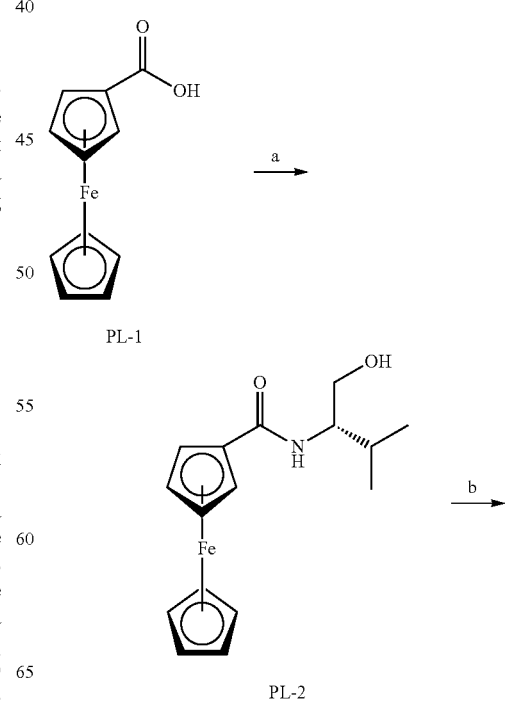

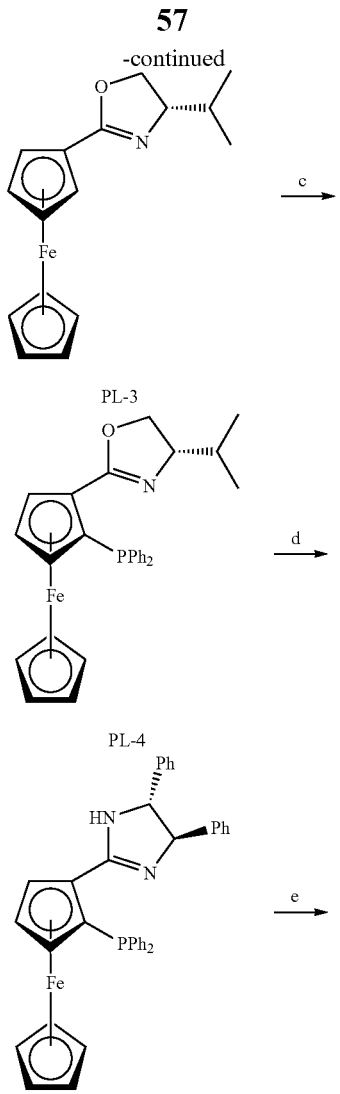

a) (COCl)₂, CH₂Cl₂, room temperature, 2 h; then (L)-(+)-vilinol, Et₃N, CH₂Cl₂, room temperature, 16 h, 77% yield; b) TsCl, Et₃N, DMAP, CH₂Cl₂, 0° C. for 1.5 h and then room temperature for 16 h, 98% yield; c) TMEDA, BuLi, hexane, -78° C., 2 h; then Ph₂PCl, room temperature, 15 min, 70% yield; d) (R,R)-DPEN, CH₃SO₃H, IPA, 85° C., 40 h, 94% yield; e) [Ir(COD)Cl]₂, CH₂Cl₂, 50° C., 1 h; then NaBArF, H₂O, rt, 15 min, 87% yield.

Lig-5: In a previously dried Schlenk tube, PL-4 (1.0 g, 2.08 mmol) and (R,R)-DPEN (2.2 g, 10.24 mmol, 5.0 eq) were dissolved in dry IPA (25 mL) under nitrogen. Methanesulfonic acid (202 μL, 3.12 mmol, 1.5 eq) was added and seven cycles of vacuum and nitrogen purge were performed. The resulting solution was stirred at 85° C. for 40 h. After cooling to room temperature, the solvent was removed under vacuum. The crude obtained was purified by column chromatography using a mixture of EtOAc/hexane 1/1. Lig-5 was isolated (1.15 g, 1.96 mmol, 94% yield) as an orange solid.

$^1$H-NMR (CDCl₃, 400 MHz) δ=3.83 (s, 1H), 4.28 (s, 5H), 4.56 (m, 1H), 4.78 (s, 2H), 5.38 (s, 1H), 7.36 (m, 18H), 7.59 (m, 2H) ppm.

$^{13}$C-NMR (CDCl₃, 100 MHz) δ=60.42, 70.79, 71.57, 72.69, 73.92, 76.46 (d, $J_{C,P}$=10.1 Hz), 127.14, 128.39 (d, $J_{C,P}$=3.0 Hz), 128.49 (d, $J_{C,P}$=6.0 Hz), 128.62, 129.61, 132.51 (d, $J_{C,P}$=18.1 Hz), 135.09 (d, $J_{C,P}$=20.1 Hz), 136.07 (d, $J_{C,P}$=8.0 Hz), 138.18 (d, $J_{C,P}$=8.0 Hz), 164.46 ppm.

$^{31}$P-NMR (CDCl₃, 162 MHz) δ=−20.17 ppm.

Cat*i: In a previously dried Schlenk tube, Lig-5 (250 mg, 0.427 mmol) and [Ir(COD)Cl]₂ (149 mg, 0.222 mmol, 0.52 eq) were dissolved in dry CH₂Cl₂ (6 mL) under nitrogen and the resulting solution was stirred at 50° C. for 1 h. After cooling to room temperature, sodium tetrakis[3,5-bis(trifluoromethyl)phenyl]borate (567 mg, 0.640 mmol, 1.5 eq) was added, followed by 6 mL of water and the resulting two-phase mixture was stirred vigorously for 15 min. The layers were separated, the aqueous phase extracted with CH₂Cl₂ and the combined organic extracts evaporated under vacuum. The crude obtained was purified by flash column chromatography using hexane/CH₂Cl₂ 1/1 to afford Cat*i (650 mg, 0.371, 87% yield) as an orange solid.

$^1$H-NMR (CDCl₃, 400 MHz) δ=1.28 (m, 2H), 1.55 (m, 1H), 2.02 (m, 3H), 2.29 (m, 1H), 2.41 (m, 1H), 2.73 (m, 1H), 3.14 (m, 1H), 4.43 (d, J=4.0 Hz, 1H), 4.60 (s, 1H), 4.63 (s, 5H), 4.70 (m, 2H), 4.81 (d, J=5.2 Hz, 1H), 4.86 (t, J=2.4 Hz, 1H), 4.98 (s, 1H), 5.95 (s, 1H), 6.54 (d, J=7.2 Hz, 2H), 7.07 (t, J=7.2 Hz, 2H), 7.20 (m, 4H), 7.39 (m, 15H), 7.51 (m, 1H), 7.63 (s, 9H) ppm.

$^{31}$P-NMR (CDCl₃, 162 MHz) δ=9.42 ppm.

HRMS (+ESI) calcd for C₄₅H₄₃FeIrN₂P: 891.2107. found: 891.2137.

Example 5d

Catalyst Cat*j Having the Structural Formula

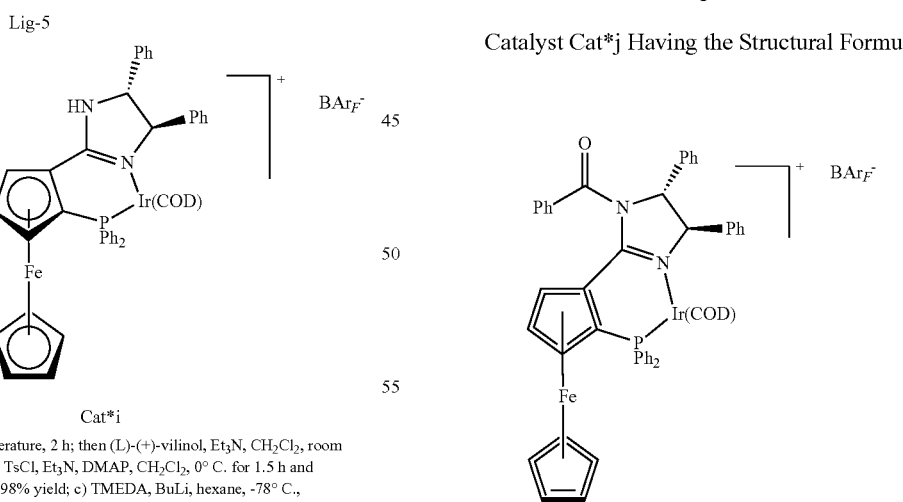

was prepared from the common precursor Lig-5 used for the synthesis of catalyst Cat*i (as described in Example 5c) by protecting initially the NH group in the imidazoline ring with a benzoyl group and forming next the corresponding Ir complex (Scheme 11b).

Scheme 11b

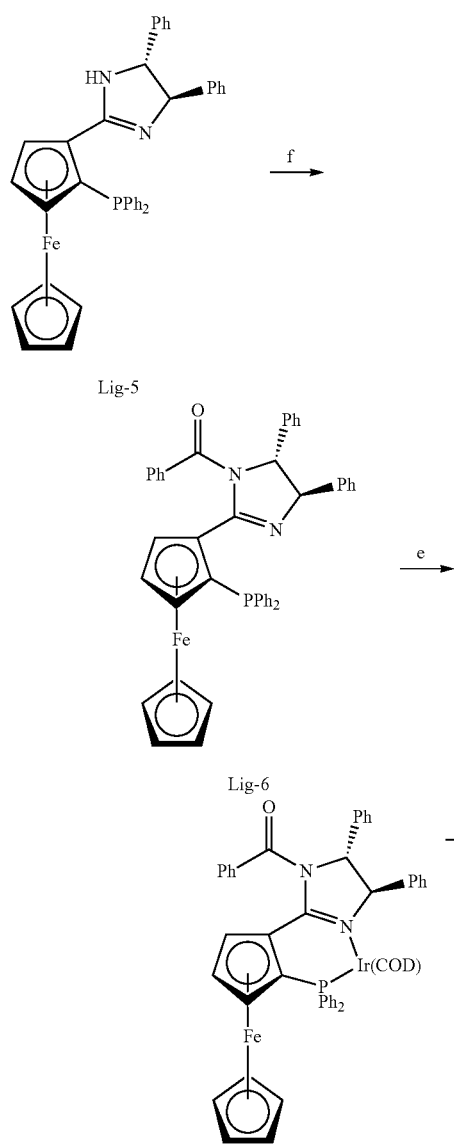

f) PhCOCl, Et₃N, CH₂Cl₂, 0° C., 1 h, 96% yield; e) [Ir(COD)Cl]₂, CH₂Cl₂, 50° C., 1 h; then NaBAr$_F$, H₂O, rt, 15 min, 84% yield.

Lig-6: In a previously dried Schlenk tube, Lig-5 (350 mg, 0.597 mmol) was dissolved in dry CH₂Cl₂ (7 mL) under nitrogen and then cooled to 0° C. Triethylamine (125 μL, 0.896 mmol, 1.5 eq.) and benzoyl chloride (76 μL, 0.657 mmol, 1.1 eq.) were added and the reaction mixture was stirred at 0° C. for 1 h. The reaction was worked up by removing the solvent under vacuum. The resulting crude was purified by flash column chromatography using a mixture EtOAc/hexane 1/4. The protected ligand Lig-6 was isolated as an orange solid (400 mg, 0.576, 96% yield).

$^1$H-NMR (CDCl₃, 400 MHz) δ=3.80 (s, 1H), 4.26 (s, 5H), 4.29 (s, 1H), 4.78 (s, 1H), 4.85 (s, 1H), 5.22 (s, 1H), 6.66 (d, J=8.4 Hz, 2H), 6.96 (t, J=7.6 Hz, 2H), 7.09 (t, J=7.6 Hz, 1H), 7.20 (t, J=7.2 Hz, 2H), 7.30 (t, J=7.6 Hz, 2H), 7.41 (m, 7H), 7.54 (m, 9H) ppm.

$^{31}$P-NMR (CDCl₃, 162 MHz) δ=−19.90 ppm.

Cat*j: In a previously dried Schlenk tube, Lig-6 (400 mg, 0.576 mmol) and [Ir(COD)Cl]₂ (201 mg, 0.299 mmol, 0.52 eq) were dissolved in dry CH₂Cl₂ (7 mL) under nitrogen and the resulting solution was stirred at 50° C. for 1 h. After cooling to room temperature, sodium tetrakis[3,5-bis(trifluoromethyl)phenyl]borate (766 mg, 0.864 mmol, 1.5 eq) was added, followed by 7 mL of water and the resulting two-phase mixture was stirred vigorously for 15 min. The layers were separated, the aqueous phase extracted with CH₂Cl₂ and the combined organic extracts evaporated under vacuum. The crude obtained was purified by flash column chromatography using hexane/CH₂Cl₂ 1/1 to afford Cat*j (896 mg, 0.482, 84% yield) as a dark red solid.

$^1$H-NMR (CDCl₃, 400 MHz) δ=1.40 (m, 2H), 1.76 (m, 1H), 2.07 (m, 1H), 2.31 (m, 4H), 3.08 (m, 1H), 3.43 (m, 1H), 4.38 (m, 1H), 4.67 (s, 5H), 4.70 (m, 1H), 4.85 (m, 2H), 4.89 (s, 1H), 4.92 (t, J=3.2 Hz, 1H), 5.10 (s, 1H), 6.64 (d, J=6.8 Hz, 2H), 7.14 (m, 4H), 7.27 (m, 2H), 7.32 (m, 1H), 7.43 (m, 1H), 7.53 (m, 15H), 7.67 (m, 2H), 7.75 (s, 10H) ppm.

$^{31}$P-NMR (CDCl₃, 162 MHz) δ=9.71 ppm.

HRMS (+ESI) calcd for C₅₂H₄₇FeIrN₂PO: 995.2438. found: 995.2399.

Example 6

Synthesis of potassium 2-(1-chloro-3-methylbut-1-enyl)trifluoroborate (Va*')

Scheme 12

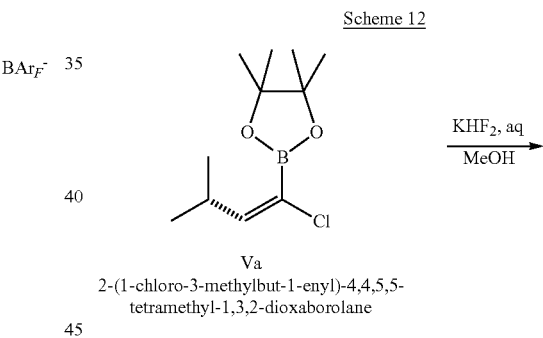

Va
2-(1-chloro-3-methylbut-1-enyl)-4,4,5,5-tetramethyl-1,3,2-dioxaborolane

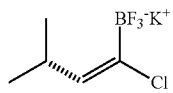

Va*'
potassium 2-(1-chloro-3-methylbut-1-enyl) trifluoroborate

To a solution of Va (2.3 g, 10 mmol) in MeOH (50 mL) was added aqueous solution of KHF₂ (20 mL, 2.8 M). The solution was stirred for 1.5 hours and concentrated in vacuum to leave a residue, which was dissolved in hot acetone (70 mL). The resulting mixture was filtered off and the filtrate was concentrated in vacuum to give a crude product, which was digested with Et₂O to afford Va*' (1.2 g, 57%) as a white powder.

$^1$H NMR (CD₃OD): δ (ppm)=0.82 (d, 6H), 2.83-2.95 (m, 1H), 4.37 (d, 1H).

$^{13}$C NMR (CD₃OD): δ (ppm)=23.6, 27.6, 139.9.

Example 7

Synthesis of potassium 2-(1-chloro-3-methylbutyl)trifluoroborate (VIa*')

Scheme 13

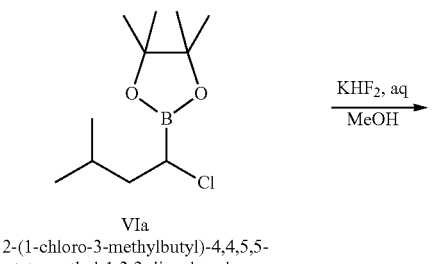

VIa
2-(1-chloro-3-methylbutyl)-4,4,5,5-tetramethyl-1,3,2-dioxaborolane

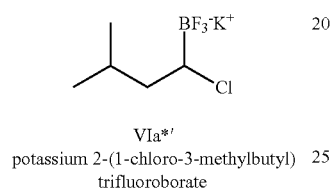

VIa*'
potassium 2-(1-chloro-3-methylbutyl) trifluoroborate

To a solution of VIa (1.5 g, 6.5 mmol) in MeOH (35 mL) was added aqueous solution of $KHF_2$ (13 mL, 2.8 M). The solution was stirred for 1.5 hours and concentrated in vacuum to leave a residue, which was dissolved in hot acetone (50 mL). The resulting mixture was filtered off and the filtrate was concentrated in vacuum to give a crude product, which was digested with $Et_2O$ to afford VIa*' (0.8 g, 60%) as a white powder.

$^1$H NMR ($CD_3OD$): δ (ppm)=1.0 (dd, 6H), 1.47 (dt, 1H), 1.76 (dt, 1H), 1.93-2.08 (m, 1H), 3.29 (d, 1H).
$^{13}$C NMR ($CD_3OD$): δ (ppm)=21.1, 24.2, 26.3, 44.1.

Example 8

Synthesis of tetra-n-butylammonium 2-(1-chloro-3-methylbut-1-enyl)trifluoroborate (Va*''')

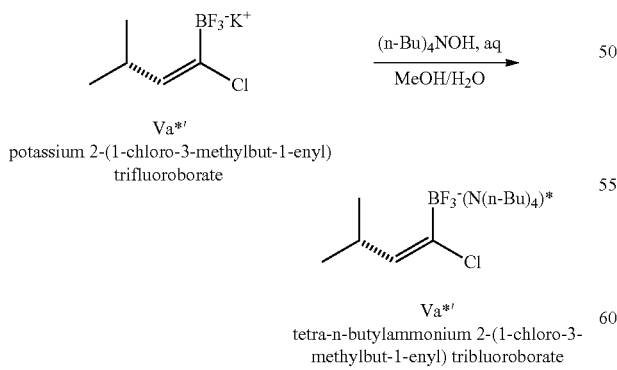

A solution of Va*' (0.63 g, 3 mmol) in MeOH (9 mL) and water (9 mL) was cooled to 0° C. and a solution of (n-Bu)$_4$NOH (2.2 mL, 3.3. mmol) was slowly added over 5 min. The reaction was warmed to room temperature and stirred for 30 min. The reaction mixture was diluted with $CH_2Cl_2$ (20 mL) and the layers were separated. The aqueous phase was washed with $CH_2Cl_2$ (3×20 mL) The combine organic phases were dried over $MgSO_4$, filtered and concentrated in vacuum to give Va*''' (1.2 g).

$^1$H NMR ($CDCl_3$): δ (ppm)=0.88 (d, 6H), 0.96 (t, 12H), 1.30-1.40 (m, 8H), 1.47-1.58 (m, 8H), 2.95-3.05 (m, 1H), 3.10-3.20 (m, 8H), 5.52 (d, 1H).
$^{13}$C NMR ($CDCl_3$): δ (ppm)=13.5, 19.5, 23.67, 23.7, 28.14, 28.16, 58.2, 58.3, 141.3.

Example 9

Synthesis of tetra-n-butylammonium 2-(1-chloro-3-methylbutyl)trifluoroborate (VIa*''')

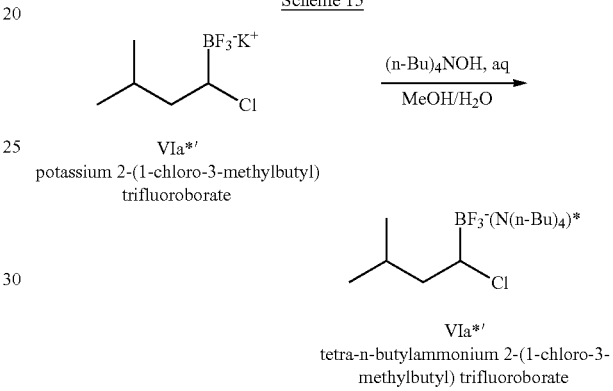

A solution of VIa*' (0.73 g, 3.4 mmol) in MeOH (10 mL) and water (10 mL) was cooled to 0° C. and a solution of (n-Bu)$_4$NOH (2.9 mL, 3.74 mmol) was slowly added over 5 min. The reaction was warmed to room temperature and stirred for 30 min. The reaction mixture was diluted with $CH_2Cl_2$ (20 mL) and the layers were separated. The aqueous phase was washed with $CH_2Cl_2$ (3×20 mL) The combine organic phases were dried over $MgSO_4$, filtered and concentrated in vacuum to give VIa*''' (1.2 g)

$^1$H NMR ($CDCl_3$): δ (ppm)=0.85 (dd, 6H), 0.96 (t, 12H), 1.37-1.49 (m, 9H), 1.55-1.64 (m, 8H), 1.70 (dt, 1H), 2.95-3.05 (m, 1H), 3.10-3.20 (m, 9H).
$^{13}$C NMR ($CDCl_3$): δ (ppm)=13.5, 19.5, 20.6, 23.7, 25.2, 43.2, 58.4.

Example 10

Synthesis of potassium 2-(1-chloro-3-methylbutyl)trifluoroborate (VIa*')

Scheme 16

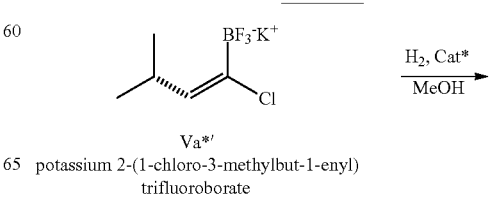

Va*'
potassium 2-(1-chloro-3-methylbut-1-enyl) trifluoroborate

-continued

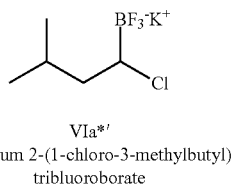

VIa*'
potassium 2-(1-chloro-3-methylbutyl)
trifluoroborate

The 75 mL stainless steel autoclave is flushed with nitrogen. The product Va*' (5.0 mmol), the (1,5-cyclooctadiene)(pyridine)(tricyclohexylphosphine)iridium(1) hexafluorophosphate (0.1 mmol) and dry MeOH (30 mL) are quickly placed in the autoclave under nitrogen atmosphere. The autoclave is sealed and pressurized/depressurized first 3 times with 6 bar of nitrogen, then 3 times with 6 bar of hydrogen. The mixture is stirred for 10 days at 50° C. under 10 bar of hydrogen. Once the autoclave has cooled to room temperature, the autoclave is carefully depressurized, the solution is poured into a round bottomed flask. The solvent is removed under reduced pressure. The product VIa*' is carried over into next step without further purification.

Example 11

Synthesis of tetra-n-ammonium 3-methyl-1-(trifluoroborate)butan-1-amine hydrochloride (VIIIa*''')

Scheme 17

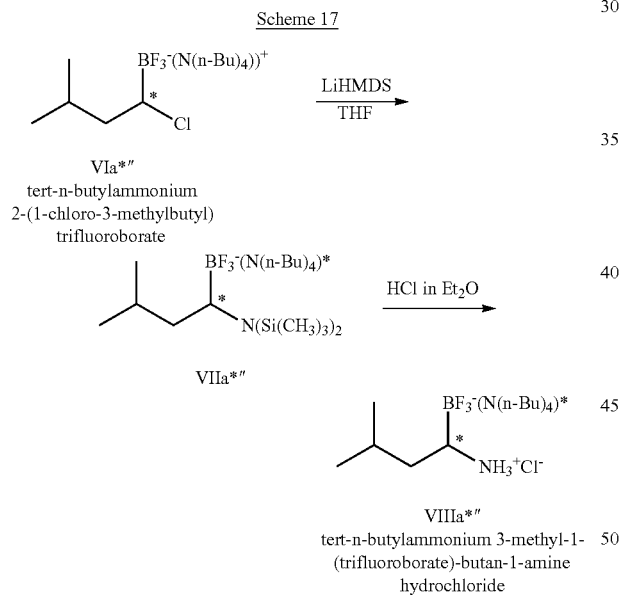

VIa*''
tert-n-butylammonium
2-(1-chloro-3-methylbutyl)
trifluoroborate

VIIa*''

VIIIa*'''
tert-n-butylammonium 3-methyl-1-
(trifluoroborate)-butan-1-amine
hydrochloride To a solution of LiHMDS (1M in THF, 3.8 mmol) in dry THF (8 mL) at −35° C. under argon atmosphere is added VIa** (3.8 mmol) dissolved in 8 mL dry THF. The solution is warmed to room temperature and stirred for 5 hours. The reaction mixture is evaporated to dryness. The residue is dissolved in 10 mL of THF, washed with 8 mL H$_2$O and 4 mL saturated aqueous solution of NaCl. The organic phase is dried over MgSO$_4$, filtrated and evaporated to dryness. To a solution of the resulting residue taken up in THF (20 mL), anhydrous HCl (4 eq, solution in Et$_2$O) is added at −60° C. under argon atmosphere. Then, reaction mixture is warmed to room temperature. The precipitating solid is isolated from reaction mixture by filtration and washed with Et$_2$O to afford VIIIa*'''.

The invention claimed is:

1. A process for producing bortezomib N-(pyrazin-2-yl) carbonyl-L-phenylalanine-L-leucine boronic acid), comprising the steps of:
   a) providing a compound of formula VI

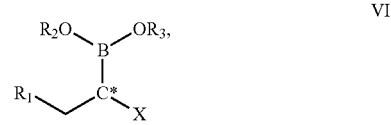

wherein:
   $R_1$ is isopropyl;
   $R_2$ and $R_3$ cooperatively form a part of a 5-membered ring representing 4,4,5,5-tetramethyl-[1,3,2]dioxaborolane;
   X is a halogen selected from the group consisting of Cl, Br and I; and
   * indicates a chiral center;
   wherein said process of providing said compound of formula VI comprises the steps of:
   (i) providing a compound of formula V

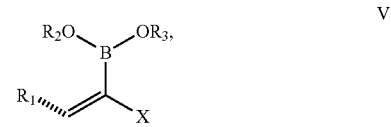

wherein $R_1$, $R_2$, $R_3$ and X are defined as above;
   (ii) converting said compound of formula V to compound of formula VI by hydrogenation, and
   (iii) optionally applying enantiomeric resolution in order to obtain enantiomerically pure compound of formula VI;
   b) converting said compound of formula VI to compound of formula VIII

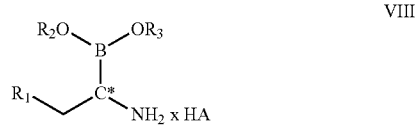

wherein $R_1$, $R_2$ and $R_3$ and R' are defined as above;
   A is an anion selected from the group of anions consisting of Cl$^-$, Br$^-$, HSO$_4^-$, CH$_3$COO$^-$, CF$_3$COO$^-$ and R'SO$_3^-$, wherein R' represents alkyl or aryl; and
   * indicates a chiral center; or free amine thereof,
   by a process comprising the steps of:
   (i) converting the compound of formula VI to compound of formula VII

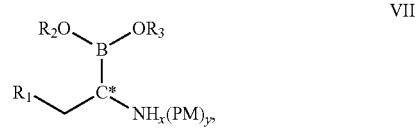

wherein $R_1$, $R_2$ and $R_3$ are defined as above, and
PM is an amino group protecting moiety, wherein PM is selected from the group consisting of tert-butanesulfinyl, tosyl, p-nitrobenzenesulfonyl, carbobenzyloxy, t-butyloxycarbonyl, benzyl, p-methoxybenzyl, dimethoxybenzyl, p-hydroxybenzyl, 9-phenylfluoren-9-yl, fluorenyl, diphenylmethyl, ferrocenylmethyl and 4-methyltrityl, and x=1 and y=1, or PM is $SiR''_3$, wherein R" represents alkyl and x=0 and y=2; and
* indicates a chiral center;
by substituting X of the compound of formula VI with a protected amino group, and
(ii) subjecting the compound of formula VII to cleavage of protection groups to yield the compound of formula VIII;
c) obtaining an enantiomerically pure compound of formula VIII by enantiomeric resolution,
d) converting the enantiomerically pure compound of formula VIII to a compound of formula XII:

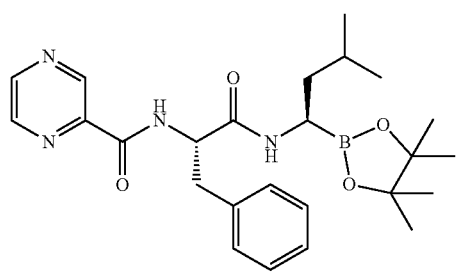

XII by a process comprising the steps of either:
(i) coupling the enantiomerically pure compound of formula VIII with the compound of formula XI

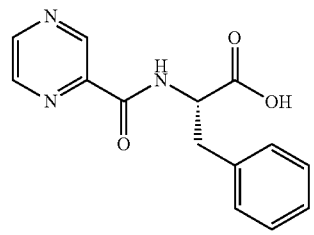

XI to give the compound of formula XII;
or (i)' coupling the enantiomerically pure compound of formula VIII with the compound of formula XIII

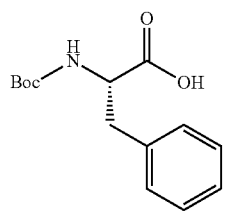

XIII to give the compound of formula XIV

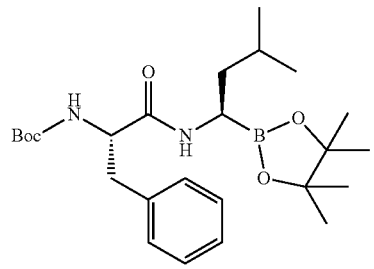

XIV (ii)' deprotecting the amino group moiety to yield the compound of formula XV

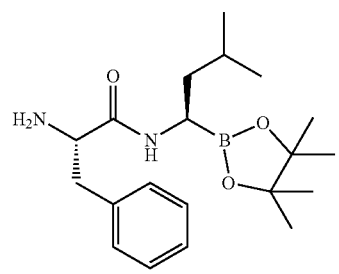

XV and,
(iii)' coupling the compound of formula XV with a compound of formula XVI

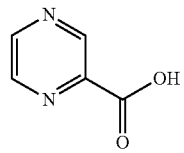

XVI to give the compound of formula XII; and
e) deprotecting the compound of formula XII to yield bortezomib.

2. The process according to claim 1, wherein said hydrogenation is conducted in the presence of a catalyst, wherein said catalyst is a catalyst for homogeneous catalysis; and/or wherein the catalyst is a complex comprising at least one transition metal.

3. The process according to claim 2, wherein the ligands of said complex are at least one ligand containing electron-rich species with various double bonded compounds and/or free electron pair containing O, N, S, or P species, wherein transition metal catalyst has chirality in the ligand and/or at the transition metal atom, or the transition metal complex having chirality is formed in situ by using an achiral procatalyst comprising the transition metal together with a cocatalyst having chirality.

4. The process according to claim 2, wherein the catalyst is/are ligand(s) selected from the group consisting of (S)-2-(1-(bis(2,6-dimethylphenyl)phosphino)-2-methylpropan-2-yl)-4-tert-butyl-4,5-dihydrooxazole; (S)-4-tert-butyl-2-(2-(diphenylphosphino)phenyl)-4,5-dihydrooxazole; (4S,5S)-

4-(2-(dicyclohexylphosphinooxy)-1,3-diphenylpropan-2-yl)-5-methyl-2-phenyl-4,5-dihydrooxazole; (R,R)—P,N-ferrocene oxazoline; (R,R)—P,N-ferrocene imidazoline; benzoyl-(R,R)—P,N-ferrocene imidazoline; (R)-(+)-2,2',6,6'-tetramethoxy4,4'-bis(diphenylphosphino)-3,3'-bipyridine; (S)-2,2',6,6'-tetramethoxy-bis[di(3,5-dimethylphenyl)phosphino]-3,3'-bipyridine; (R)-4,12-bis(diphenylphosphino)-[2.2]-paracyclophane; 1-(S)—N-methyl-N-(diphenyl-phosphino)-1-[(R)-(diphenylphosphino)-ferrocenyl]ethylamine; (R)-2-(1-naphthyl)-8-diphenylphosphino-1-(S)-3,5-dioxa-4-phosphacyclohepta[2,1-1;3,4-a']di-naphthalen-4-yl)-1,2-dihydroquinoline toluene adduct; (S)-(+)-4,12-bis[di(3,5-dimethylphenyl)phosphino]-[2.2]paracyclophane; (R)-2,2'-bis(diphenyl-phosphinoamino)-5,5',6,6',7,7',8,8'-octahydro-1,1'-binaphthyl.

5. The process according to claim 2, wherein the transition metal is selected from the group consisting of Cu, Co, Ni, Rh, Ru, Pd and Ir.

6. The process according to claim 2, wherein the catalyst is selected from the group consisting of (1,5-cyclooctadiene)(pyridine)(tricyclohexyl-phosphine)iridium(I)hexafluorophosphate; (1,5-cyclooctadiene)iridium(I)tetrakis[3,5-bis(trifluoromethyl)phenyl]borate (S)-2-(1-(bis(2,6-dimethylphenyl)phosphino)-2-methylpropan-2-yl)-4-tert-butyl-4,5-dihydrooxazole; (1,5-cyclooctadiene)iridium(I)tetrakis[3,5-bis(trifluoromethyl)phenyl]borate (S)-4-tert-butyl-2-(2-(diphenylphosphino)phenyl)-4,5-dihydro-oxazole; (1,5-cyclooctadiene)iridium(I)tetrakis[3,5-bis(trifluoromethyl)phenyl]borate (4S,5S)-4-(2-(dicyclohexylphosphinooxy)-1,3-diphenylpropan-2-yl)-5-methyl-2-phenyl-4,5-dihydrooxazole; (1,5-cyclooctadiene)iridium(I)tetrakis[3,5-bis(trifluoromethyl)phenyl]borate (R,R)—P, N-ferrocene oxazoline; (1,5-cyclooctadiene)iridium(I)tetrakis[3,5-bis(trifluoromethyl)phenyl]borate (R,R)—P,N-ferrocene imidazoline and (1,5-cyclooctadiene)iridium(I)tetrakis[3,5-bis(trifluoromethyl)phenyl]borate benzoyl-(R,R)—P,N-ferrocene imidazoline, bis(1,5-cyclooctadiene)diiridium(I) dichloride (R)-(+)-2,2',6,6'-tetramethoxy-4,4'-bis(diphenylphosphino)-3,3'-bipyridine; bis(1,5-cyclooctadiene)diiridium(I)dichloride (S)-2,2',6,6'-tetramethoxy-bis[di(3,5-dimethylphenyl)phosphino]-3,3'-bipyridine; bis(1,5-cyclooctadiene)dirhodium(I)dichloride (S)-2,2',6,6'-tetramethoxy-bis[di(3,5-dimethylphenyl)phosphino]-3,3'-bipyridine; bis(cycloocta-1,5-diene)rhodium(I) tetrafluoroborate (R)-4,12-bis(diphenylphosphino)-[2.2]-paracyclophane; benzeneruthenium(II) dichloride dimer 1-(S)—N-methyl-N-(diphenylphosphino)-1-[(R)-(diphenylphosphino)-ferrocenyl]ethylamine; and bis(2-methylallyl)(1,5-cyclooctadien)ruthenium(II) (S)-(+)-4,12-bis[di(3,5-dimethylphenyl)phosphino]-[2.2]paracyclophane.

7. The process according to claim 2, wherein dehalogenation is essentially avoided during hydrogenation, wherein dehalogenation occurs in less than 10 molar %, relative to the molar amount of compound of formula VI.

8. A process for producing a pharmaceutical composition comprising the steps of:
(i) preparing bortezomib N-(pyrazin-2-yl)carbonyl-L-phenylalanine-L-leucine-boronic acid) or ester or anhydride or salt thereof according to claim 7, and
(ii) mixing said bortezomib with at least one excipient.

* * * * *